US006881825B1

(12) United States Patent
Robbins et al.

(10) Patent No.: US 6,881,825 B1
(45) Date of Patent: Apr. 19, 2005

(54) IDENTICATION OF PEPTIDES THAT FACILITATE UPTAKE AND CYTOPLASMIC AND/OR NUCLEAR TRANSPORT OF PROTEINS, DNA AND VIRUES

(75) Inventors: Paul D. Robbins, Mt. Lebanon, PA (US); Zhibao Mi, Pittsburgh, PA (US); Raymond Frizzell, Pittsburgh, PA (US); Joseph C. Glorioso, Cheswick, PA (US); Andrea Gambotto, Pittsburgh, PA (US)

(73) Assignee: University of Pittsburgh of The Commonwealth System of Higher Education, Pittsburgh, PA (US)

(*) Notice: Subject to any disclaimer, the term of this patent is extended or adjusted under 35 U.S.C. 154(b) by 244 days.

(21) Appl. No.: 09/653,182

(22) Filed: Aug. 31, 2000

Related U.S. Application Data
(60) Provisional application No. 60/151,980, filed on Sep. 1, 1999, and provisional application No. 60/188,944, filed on Mar. 13, 2000.

(51) Int. Cl.$^7$ .......................... A61K 38/04; C12P 21/08
(52) U.S. Cl. ...................... 530/327; 530/300; 530/326; 435/69.1; 435/69.7; 514/2; 514/14
(58) Field of Search ................................ 530/300, 327, 530/326, 324, 350; 514/2, 14, 1, 12, 21; 435/69.1, 69.7, 375, 91.1, 172.1, 252.3

(56) References Cited

U.S. PATENT DOCUMENTS

| | | | |
|---|---|---|---|
| 5,338,665 | A | 8/1994 | Schatz et al. |
| 5,804,604 | A | 9/1998 | Frankel et al. |
| 6,017,735 | A | 1/2000 | O'Hare et al. |
| 6,184,038 | B1 | 2/2001 | O'Hare et al. |
| 6,221,355 | B1 | 4/2001 | Dowdy |

FOREIGN PATENT DOCUMENTS

| | | |
|---|---|---|
| EP | 0903408 | 3/1999 |
| WO | 9851325 | 11/1998 |
| WO | 9851825 | 11/1998 |
| WO | 9906542 | 2/1999 |
| WO | 9910485 | 3/1999 |
| WO | 99/55899 A1 | 11/1999 |
| WO | 00/62067 A1 | 10/2000 |
| WO | 01/13957 A2 | 6/2001 |

OTHER PUBLICATIONS

Skolnick, J. and Fetrow, J.S., "From genes to protein structure and function: novel applications of computational approaches in the genomic era," TIBTECH, Jan. 2000, vol. 18, pp. 34–39.*
Schwarze and Dowdy, 2000, TIPS 21: 45–48.
Elliot and O'Hare, 2000, J. Virol. 74: 2131–2141.
Branden et al., 1999, Nat. Biotechnol. 17: 784–787.
Brown & Wauters, 1999, Cancer Res. 59: 1391–1399.
Ellerby et al., 1999, Nat. Med. 5: 1032.
Derer et al., 1999, J. Mol. Med. 77: 609–613.
Gambotto et al., 1999. Cancer Gene Ther. 6: 45.
Hiroshi et al., 1999, Gene Ther. 6: 1988.
Ivanenkov and Menon, 1999, Biochem et. Biophys. Acta. 1448: 463–472.
Ivanenkov and Menon, 1999, Biochem. et Biophys. Acta 1448: 450–462.
Kim et al., 1999, Cancer Immunol. Immunother . 47: 527.
Osaki et al., 1999, Gene Ther. 6: 808.
Pittenger et al., 1999, Science 284: 143.
Nishioka et al., 1999, Cancer Res. 59: 4035.
Shwarze et al., 1999, Science 285: 1569–1572.
Vocero–Akbani et al. 1999, Nat. Med. 5: 29–33.
Yamabe et al., 1999, Gene Ther 6: 1952–1959.
Derossi et al., 1998, Trends in Cell Biol. 8: 84–87.
Ghivizzani et al., 1998. Proc. Natl. Acad. Sci. USA 95: 4613.
Mangency and Heidmann, 1988, Proc. Natl. Acad. Sci. USA 95: 14920.
Nagahara et al., 1998, Nat. Med. 4: 1449–1452.
Noffz et al., 1988, J. Immunol. 160: 345.
Osaki et al., 1998, J. Immunol. 160: 1742.
Sakai et al., 1998, Arthritis Rheum. 41: 1251–1257.
Villaverde et al., 1998, Biotechnol. and Bioeng. 59: 294–301.
Wakisaka et al., 1998, Clin. Exp. Immunol. 114: 119–128.
Cayeux et al., 1997, J. Immunol. 158: 2834.
Elliot and O'Hare, 1997, Cell 188: 223–233.
Felgner, 1997, Sci. Am. 276: 102–106.
Ghivizzani et al., 1997, Gene Ther. 4: 977.
Ghivizzani et al., 1997, J. immunol. 159: 3604.
Kato and Sugiyams. 1997. Crit. Rev. Ther. Drug Carrier Syst. 14: 287–331.
Kirpotin et al., 1997. Biochemistry 36: 66–75.
Knudsen and Nielsen, 1997, Anticancer Drugs 8: 113–118.
Spragg et al., 1997, Proc. Natl. Acad. Sci. USA 94: 8795–8800.
Szardenings et al., 1997, J. Biol. Chem. 272: 27943–27948.
Vives, et al., 1997, J. Biol. Che., 272: 16010–16017.
Barry and Johnson, 1996, Nat. Med. 2: 299–305.
Berlose et al., 1996, Eur. J. Biochem. 242: 372.
Derossi et al., 1996. J. Biochem. 217: 18188–18193.
Fitzgerald, 1996, Semin. Cancer Biol. 7: 87–95.
Moy et al., 1996, Mol. Biotechnol. 6: 105–113.
Nita et al., 1996, Arthritis Rheum. 39: 820.
Ohno et al., 1996, J. Immunol. 156: 3875.
Sato et al., 1996, Adv. Drug. Deliv. Rev. 19: 445–467.
Zeigler et al., 1996, Transplantation 61: 812–817.
Wickham et al., 1995, Gene Ther. 2: 750–756.

(Continued)

Primary Examiner—Padmashri Ponnaluri
(74) Attorney, Agent, or Firm—Baker Botts LLP

(57) ABSTRACT

The present invention relates to internalizing peptides which facilitate the uptake and transport of cargo into the cytoplasm and nuclei of cells as well as methods for the identification of the peptides, and methods of use for the peptides. The internalizing peptides of the present invention are selected for their ability to efficiently internalize cargo into a wide variety of cell types both in vivo and in vitro.

14 Claims, 40 Drawing Sheets

OTHER PUBLICATIONS

Berns and Giraud, 1995. *Ann. N. Y. Acad. Sci. 772*: 95–104.
Haneberg et al., 1995. *Adv. Exp. Med. Biol. 371*: 107–109.
Smith, 1995, *Ann. Rev. Microbiol. 49*: 807–838.
Yang et al., 1995, *J. Virol. 69*: 2004–2015.
Fawell et al., 1994, *Proc. Natl. Acad. Sci. USA 91*: 664–668.
Kuzel and Rosen, 1994, *Curr. Opin. Oncol. 6*: 622–626.
Sreerama and Woody, 1994, *Biochemistry 33*: 10022–10025.
Weitzman et al., 1994, *Proc. Natl. Acad. Sci. USA 91*: 5808–5812.
Kozarsky and Wilson, 1993, *Curr. Opin. Genet. Dev. 3*: 49–50.
Miller et al., 1993, *Lab Invest. 68*: 129–145.
Mulligan. 1993, *Science 260*:926–932.
Vitetta et al., 1993, *Immunol. Today 14*: 252–259.
Zatloukal et al., 1993. *Gene 135*: 199–207.
Wagner et al., 1992, *Proc. Natl. Acad. Sci. 89*: 6099–6103.
Wagner et al., 1992, *Proc. Natl. Acad. Sci. 89*: 7934–7938.
Evans, 1991, *Agents Actious Suppl. 32*: 135–152.
Curiel et al., 1991, *Proc. Natl. Acad. Sci. 88*: 8850–8854.
Basu, 1990, *Biochem. Pharmacol. 40*: 1941–1946.
Wu and Wu, 1989, *J. Biol. Chem. 264*: 16985–16987.
Frankel and Pabo, 1988, *Cell 55*: 1189–1193.
Green and Lowenstein, 1988, *Cell 55*: 1179–1188.
Wu and Wu. 1988, *J. Biol. Chem. 263*: 14621–16424.
Wu and Wu, 1987, *J. Biol. Chem. 262*: 4429–4432.
Bayer et al., 1976, *Histichem. Cytochem. 24*: 933–939.

* cited by examiner

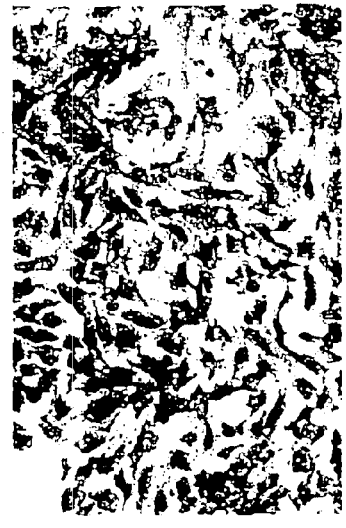

KLA

DP1

KLA

DP1

CD34⁺/LIN⁻ Stem Cells Are Transduced by a
CTP-5-Biotin/Avidin-β-Galactosidase
Complex

SEQUENCE LISTING

<160> NUMBER OF SEQ ID NOS: 75

<210> SEQ ID NO 1
<211> LENGTH: 12
<212> TYPE: PRT
<213> ORGANISM: Artificial Sequence
<220> FEATURE:
<223> OTHER INFORMATION: random peptide library

<400> SEQUENCE: 1

Lys Arg Ile Ile Gln Arg Ile Leu Ser Arg Asn Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: random peptide library

<400> SEQUENCE: 2

Lys Arg Ile His Pro Arg Leu Thr Arg Ser Ile Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: random peptide library

<400> SEQUENCE: 3

Pro Pro Arg Leu Arg Lys Arg Gln Leu Asn Met
1               5                   10

<210> SEQ ID NO 4
<211> LENGTH: 12
<212> TYPE: PRT
<213> ORGANISM: Artificial Sequence
<220> FEATURE:
<223> OTHER INFORMATION: random peptide library

<400> SEQUENCE: 4

Pro Ile Arg Arg Arg Lys Lys Leu Arg Arg Leu Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: random peptide library

<400> SEQUENCE: 5

Arg Arg Gln Arg Arg Thr Ser Lys Leu Met Lys Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: random peptide library

<400> SEQUENCE: 6

Met His Lys Arg Pro Thr Thr Pro Ser Arg Lys Met
1               5                   10

<210> SEQ ID NO 7
<211> LENGTH: 12
<212> TYPE: PRT
<213> ORGANISM: Artificial Sequence
<220> FEATURE:
<223> OTHER INFORMATION: random peptide library

```
<400> SEQUENCE: 7

Arg Gln Arg Ser Arg Arg Pro Leu Asn Ile Arg
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: random peptide library

<400> SEQUENCE: 8

Arg Ile Arg Met Ile Gln Asn Leu Ile Lys Lys Thr
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: random peptide library

<400> SEQUENCE: 9

Ser Arg Arg Lys Arg Gln Arg Ser Asn Met Arg Ile
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: random peptide library

<400> SEQUENCE: 10

Gln Arg Ile Arg Lys Ser Lys Ile Ser Arg Thr Leu
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: random peptide library

<400> SEQUENCE: 11

Pro Ser Lys Arg Leu Leu His Asn Asn Leu Arg Arg
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: random peptide library

<400> SEQUENCE: 12

His Arg His Ile Arg Arg Gln Ser Leu Ile Met Leu
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: random peptide library

<400> SEQUENCE: 13
```

```
Pro Gln Asn Arg Leu Gln Ile Arg Arg His Ser Lys
  1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: random peptide library

<400> SEQUENCE: 14

```
Pro Pro His Asn Arg Ile Gln Arg Arg Leu Asn Met
  1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: random peptide library

<400> SEQUENCE: 15

```
Ser Met Leu Lys Arg Asn His Ser Thr Ser Asn Arg
  1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: random peptide library

<400> SEQUENCE: 16

```
Gly Ser Arg His Pro Ser Leu Ile Ile Pro Arg Gln
  1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: random peptide library

<400> SEQUENCE: 17

```
Ser Pro Met Gln Lys Thr Met Asn Leu Pro Pro Met
  1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: random peptide library

<400> SEQUENCE: 18

```
Asn Lys Arg Ile Leu Ile Arg Ile Met Thr Arg Pro
  1               5                   10
```

<210> SEQ ID NO 19
<211> LENGTH: 16
<212> TYPE: PRT
<213> ORGANISM: antennepedia

<400> SEQUENCE: 19

```
Arg Gln Ile Lys Ile Trp Phe Gln Asn Arg Arg Met Lys Trp Lys Lys
  1               5                   10                  15
```

```
<210> SEQ ID NO 20
<211> LENGTH: 12
<212> TYPE: PRT
<213> ORGANISM: Artificial Sequence
<220> FEATURE:
<223> OTHER INFORMATION: random peptide library

<400> SEQUENCE: 20

Ala Arg Pro Leu Glu His Gly Ser Asp Lys Ala Thr
 1               5                  10

<210> SEQ ID NO 21
<211> LENGTH: 11
<212> TYPE: PRT
<213> ORGANISM: human

<400> SEQUENCE: 21

Tyr Gly Arg Lys Lys Arg Arg Gln Arg Arg
 1               5                  10

<210> SEQ ID NO 22
<211> LENGTH: 7
<212> TYPE: PRT
<213> ORGANISM: Artificial Sequence
<220> FEATURE:
<223> OTHER INFORMATION: random peptide library

<400> SEQUENCE: 22

Lys Leu Ala Lys Leu Ala Lys
 1               5

<210> SEQ ID NO 23
<211> LENGTH: 14
<212> TYPE: PRT
<213> ORGANISM: Artificial Sequence
<220> FEATURE:
<223> OTHER INFORMATION: random peptide library

<400> SEQUENCE: 23

Lys Leu Ala Lys Leu Ala Lys Lys Leu Ala Lys Leu Ala Lys
 1               5                  10

<210> SEQ ID NO 24
<211> LENGTH: 28
<212> TYPE: PRT
<213> ORGANISM: Artificial Sequence
<220> FEATURE:
<223> OTHER INFORMATION: random peptide library

<400> SEQUENCE: 24

Arg Arg Gln Arg Arg Thr Ser Lys Leu Met Lys Arg Gly Gly Lys Leu
 1               5                  10                  15

Ala Lys Leu Ala Lys Lys Leu Ala Lys Leu Ala Lys
             20                  25

<210> SEQ ID NO 25
<211> LENGTH: 12
<212> TYPE: PRT
<213> ORGANISM: Artificial Sequence
<220> FEATURE:
<223> OTHER INFORMATION: random peptide library

<400> SEQUENCE: 25

His Gly Trp Glx Ile His Gly Leu Leu His Arg Ala
 1               5                  10
```

<210> SEQ ID NO 26
<211> LENGTH: 11
<212> TYPE: PRT
<213> ORGANISM: Artificial Sequence
<220> FEATURE:
<223> OTHER INFORMATION: random peptide library

<400> SEQUENCE: 26

Ala Val Pro Ala Lys Lys Arg Glx Lys Ser Val
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: random peptide library

<400> SEQUENCE: 27

Pro Asn Thr Arg Val Arg Pro Asp Val Ser Phe
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: random peptide library

<400> SEQUENCE: 28

Leu Thr Arg Asn Tyr Glu Ala Trp Val Pro Thr Pro
 1               5                  10

<210> SEQ ID NO 29
<211> LENGTH: 13
<212> TYPE: PRT
<213> ORGANISM: Artificial Sequence
<220> FEATURE:
<223> OTHER INFORMATION: random peptide library

<400> SEQUENCE: 29

Ser Ala Glu Thr Val Glu Ser Cys Leu Ala Lys Ser His
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: random peptide library

<400> SEQUENCE: 30

Tyr Ser His Ile Ala Thr Leu Pro Phe Thr Pro Thr
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: random peptide library

<400> SEQUENCE: 31

Ser Tyr Ile Gln Arg Thr Pro Ser Thr Thr Leu Pro
 1               5                  10

```
<210> SEQ ID NO 32
<211> LENGTH: 12
<212> TYPE: PRT
<213> ORGANISM: Artificial Sequence
<220> FEATURE:
<223> OTHER INFORMATION: random peptide library

<400> SEQUENCE: 32

Ala Val Pro Ala Glu Asn Ala Leu Asn Asn Pro Phe
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: random peptide library

<400> SEQUENCE: 33

Ser Phe His Gln Phe Ala Arg Ala Thr Leu Ala Ser
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: random peptide library

<400> SEQUENCE: 34

Gln Ser Pro Thr Asp Phe Thr Phe Pro Asn Pro Leu
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: random peptide library

<400> SEQUENCE: 35

His Phe Ala Ala Trp Gly Gly Trp Ser Leu Val His
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: random peptide library

<400> SEQUENCE: 36

His Ile Gln Leu Ser Pro Phe Ser Gln Ser Trp Arg
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: random peptide library

<400> SEQUENCE: 37

Leu Thr Met Pro Ser Asp Leu Gln Pro Val Leu Trp
 1               5                  10
```

```
<210> SEQ ID NO 38
<211> LENGTH: 12
<212> TYPE: PRT
<213> ORGANISM: Artificial Sequence
<220> FEATURE:
<223> OTHER INFORMATION: random peptide library

<400> SEQUENCE: 38

Phe Gln Pro Tyr Asp His Pro Ala Glu Val Ser Tyr
 1               5                  10

<210> SEQ ID NO 39
<211> LENGTH: 12
<212> TYPE: PRT
<213> ORGANISM: Artificial Sequence
<220> FEATURE:
<223> OTHER INFORMATION: random peptide library

<400> SEQUENCE: 39

Phe Asp Pro Phe Phe Trp Lys Tyr Ser Pro Arg Asp
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: random peptide library

<400> SEQUENCE: 40

Phe Ala Pro Trp Asp Thr Ala Ser Phe Met Leu Gly
 1               5                  10

<210> SEQ ID NO 41
<211> LENGTH: 12
<212> TYPE: PRT
<213> ORGANISM: Artificial Sequence
<220> FEATURE:
<223> OTHER INFORMATION: random peptide library

<400> SEQUENCE: 41

Phe Thr Tyr Lys Asn Phe Phe Trp Leu Pro Glu Leu
 1               5                  10

<210> SEQ ID NO 42
<211> LENGTH: 12
<212> TYPE: PRT
<213> ORGANISM: Artificial Sequence
<220> FEATURE:
<223> OTHER INFORMATION: random peptide library

<400> SEQUENCE: 42

Ser Ala Thr Gly Ala Pro Trp Lys Met Trp Val Arg
 1               5                  10

<210> SEQ ID NO 43
<211> LENGTH: 12
<212> TYPE: PRT
<213> ORGANISM: Artificial Sequence
<220> FEATURE:
<223> OTHER INFORMATION: random peptide library

<400> SEQUENCE: 43

Ser Leu Gly Trp Met Leu Pro Phe Ser Pro Pro Phe
 1               5                  10

<210> SEQ ID NO 44
```

```
<211> LENGTH: 12
<212> TYPE: PRT
<213> ORGANISM: Artificial Sequence
<220> FEATURE:
<223> OTHER INFORMATION: random peptide library

<400> SEQUENCE: 44

Ser His Ala Phe Thr Trp Pro Thr Tyr Leu Gln Leu
 1               5                  10

<210> SEQ ID NO 45
<211> LENGTH: 12
<212> TYPE: PRT
<213> ORGANISM: Artificial Sequence
<220> FEATURE:
<223> OTHER INFORMATION: random peptide library

<400> SEQUENCE: 45

Ser His Asn Trp Leu Pro Leu Trp Pro Leu Arg Pro
 1               5                  10

<210> SEQ ID NO 46
<211> LENGTH: 12
<212> TYPE: PRT
<213> ORGANISM: Artificial Sequence
<220> FEATURE:
<223> OTHER INFORMATION: random peptide library

<400> SEQUENCE: 46

Ser Trp Leu Pro Tyr Pro Trp His Val Pro Ser Ser
 1               5                  10

<210> SEQ ID NO 47
<211> LENGTH: 12
<212> TYPE: PRT
<213> ORGANISM: Artificial Sequence
<220> FEATURE:
<223> OTHER INFORMATION: random peptide library

<400> SEQUENCE: 47

Ser Trp Trp Thr Pro Trp His Val His Ser Glu Ser
 1               5                  10

<210> SEQ ID NO 48
<211> LENGTH: 12
<212> TYPE: PRT
<213> ORGANISM: Artificial Sequence
<220> FEATURE:
<223> OTHER INFORMATION: random peptide library

<400> SEQUENCE: 48

Ser Trp Ala Gln His Leu Ser Leu Pro Pro Val Leu
 1               5                  10

<210> SEQ ID NO 49
<211> LENGTH: 12
<212> TYPE: PRT
<213> ORGANISM: Artificial Sequence
<220> FEATURE:
<223> OTHER INFORMATION: random peptide library

<400> SEQUENCE: 49

Ser Ser Ser Ile Phe Pro Pro Trp Leu Ser Phe Phe
 1               5                  10

<210> SEQ ID NO 50
<211> LENGTH: 12
```

```
<212> TYPE: PRT
<213> ORGANISM: Artificial Sequence
<220> FEATURE:
<223> OTHER INFORMATION: random peptide library

<400> SEQUENCE: 50

Leu Asn Val Pro Pro Ser Trp Phe Leu Ser Gln Arg
 1               5                  10

<210> SEQ ID NO 51
<211> LENGTH: 12
<212> TYPE: PRT
<213> ORGANISM: Artificial Sequence
<220> FEATURE:
<223> OTHER INFORMATION: random peptide library

<400> SEQUENCE: 51

Leu Asp Ile Thr Pro Phe Leu Ser Leu Thr Leu Pro
 1               5                  10

<210> SEQ ID NO 52
<211> LENGTH: 12
<212> TYPE: PRT
<213> ORGANISM: Artificial Sequence
<220> FEATURE:
<223> OTHER INFORMATION: random peptide library

<400> SEQUENCE: 52

Leu Pro His Pro Val Leu His Met Gly Pro Leu Arg
 1               5                  10

<210> SEQ ID NO 53
<211> LENGTH: 12
<212> TYPE: PRT
<213> ORGANISM: Artificial Sequence
<220> FEATURE:
<223> OTHER INFORMATION: random peptide library

<400> SEQUENCE: 53

Val Ser Lys Gln Pro Tyr Tyr Met Trp Asn Gly Asn
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: random peptide library

<400> SEQUENCE: 54

Asn Tyr Thr Thr Tyr Lys Ser His Phe Gln Asp Arg
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: random peptide library

<400> SEQUENCE: 55

Ala Ile Pro Asn Asn Gln Leu Gly Phe Pro Phe Lys
 1               5                  10

<210> SEQ ID NO 56
<211> LENGTH: 12
<212> TYPE: PRT
```

```
<213> ORGANISM: Artificial Sequence
<220> FEATURE:
<223> OTHER INFORMATION: random peptide library

<400> SEQUENCE: 56

Asn Ile Glu Asn Ser Thr Leu Ala Thr Pro Leu Ser
 1               5                  10

<210> SEQ ID NO 57
<211> LENGTH: 12
<212> TYPE: PRT
<213> ORGANISM: Artificial Sequence
<220> FEATURE:
<223> OTHER INFORMATION: random peptide library

<400> SEQUENCE: 57

Tyr Pro Tyr Asp Ala Asn His Thr Arg Ser Pro Thr
 1               5                  10

<210> SEQ ID NO 58
<211> LENGTH: 12
<212> TYPE: PRT
<213> ORGANISM: Artificial Sequence
<220> FEATURE:
<223> OTHER INFORMATION: random peptide library

<400> SEQUENCE: 58

Asp Pro Ala Thr Asn Pro Gly Pro His Phe Pro Arg
 1               5                  10

<210> SEQ ID NO 59
<211> LENGTH: 12
<212> TYPE: PRT
<213> ORGANISM: Artificial Sequence
<220> FEATURE:
<223> OTHER INFORMATION: random peptide library

<400> SEQUENCE: 59

Thr Leu Pro Ser Pro Leu Ala Leu Leu Thr Val His
 1               5                  10

<210> SEQ ID NO 60
<211> LENGTH: 12
<212> TYPE: PRT
<213> ORGANISM: Artificial Sequence
<220> FEATURE:
<223> OTHER INFORMATION: random peptide library

<400> SEQUENCE: 60

His Pro Gly Ser Pro Phe Pro Pro Glu His Arg Pro
 1               5                  10

<210> SEQ ID NO 61
<211> LENGTH: 12
<212> TYPE: PRT
<213> ORGANISM: Artificial Sequence
<220> FEATURE:
<223> OTHER INFORMATION: random peptide library

<400> SEQUENCE: 61

Thr Ser His Thr Asp Ala Pro Pro Ala Arg Ser Pro
 1               5                  10

<210> SEQ ID NO 62
<211> LENGTH: 12
<212> TYPE: PRT
<213> ORGANISM: Artificial Sequence
```

```
<220> FEATURE:
<223> OTHER INFORMATION: random peptide library

<400> SEQUENCE: 62

Met Thr Pro Ser Ser Leu Ser Thr Leu Pro Trp Pro
 1               5                  10

<210> SEQ ID NO 63
<211> LENGTH: 12
<212> TYPE: PRT
<213> ORGANISM: Artificial Sequence
<220> FEATURE:
<223> OTHER INFORMATION: random peptide library

<400> SEQUENCE: 63

Val Leu Gly Gln Ser Gly Tyr Leu Met Pro Met Arg
 1               5                  10

<210> SEQ ID NO 64
<211> LENGTH: 12
<212> TYPE: PRT
<213> ORGANISM: Artificial Sequence
<220> FEATURE:
<223> OTHER INFORMATION: random peptide library

<400> SEQUENCE: 64

Gln Pro Ile Ile Ile Thr Ser Pro Tyr Leu Pro Ser
 1               5                  10

<210> SEQ ID NO 65
<211> LENGTH: 12
<212> TYPE: PRT
<213> ORGANISM: Artificial Sequence
<220> FEATURE:
<223> OTHER INFORMATION: random peptide library

<400> SEQUENCE: 65

Thr Pro Lys Thr Met Thr Gln Thr Tyr Asp Phe Ser
 1               5                  10

<210> SEQ ID NO 66
<211> LENGTH: 12
<212> TYPE: PRT
<213> ORGANISM: Artificial Sequence
<220> FEATURE:
<223> OTHER INFORMATION: random peptide library

<400> SEQUENCE: 66

Asn Ser Gly Thr Met Gln Ser Ala Ser Arg Ala Thr
 1               5                  10

<210> SEQ ID NO 67
<211> LENGTH: 12
<212> TYPE: PRT
<213> ORGANISM: Artificial Sequence
<220> FEATURE:
<223> OTHER INFORMATION: random peptide library

<400> SEQUENCE: 67

Gln Ala Ala Ser Arg Val Glu Asn Tyr Met His Arg
 1               5                  10

<210> SEQ ID NO 68
<211> LENGTH: 12
<212> TYPE: PRT
<213> ORGANISM: Artificial Sequence
<220> FEATURE:
```

<223> OTHER INFORMATION: random peptide library

<400> SEQUENCE: 68

His Gln His Lys Pro Pro Pro Leu Thr Asn Asn Trp
 1               5                  10

<210> SEQ ID NO 69
<211> LENGTH: 12
<212> TYPE: PRT
<213> ORGANISM: Artificial Sequence
<220> FEATURE:
<223> OTHER INFORMATION: random peptide library

<400> SEQUENCE: 69

Ser Asn Pro Trp Asp Ser Leu Leu Ser Val Ser Thr
 1               5                  10

<210> SEQ ID NO 70
<211> LENGTH: 12
<212> TYPE: PRT
<213> ORGANISM: Artificial Sequence
<220> FEATURE:
<223> OTHER INFORMATION: random peptide library

<400> SEQUENCE: 70

Lys Thr Ile Glu Ala His Pro Pro Tyr Tyr Ala Ser
 1               5                  10

<210> SEQ ID NO 71
<211> LENGTH: 12
<212> TYPE: PRT
<213> ORGANISM: Artificial Sequence
<220> FEATURE:
<223> OTHER INFORMATION: random peptide library

<400> SEQUENCE: 71

Glu Pro Asp Asn Trp Ser Leu Asp Phe Pro Arg Arg
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: random peptide library

<400> SEQUENCE: 72

His Gln His Lys Pro Pro Pro Leu Thr Asn Asn Trp
 1               5                  10

<210> SEQ ID NO 73
<211> LENGTH: 19
<212> TYPE: PRT
<213> ORGANISM: Artificial Sequence
<220> FEATURE:
<223> OTHER INFORMATION: random peptide library

<400> SEQUENCE: 73

Gly Val Val Gly Lys Leu Gly Gln Arg Arg Thr Lys Lys Gln Arg Arg
 1               5                  10                  15

Gln Lys Lys

<210> SEQ ID NO 74
<211> LENGTH: 31
<212> TYPE: PRT
<213> ORGANISM: Artificial Sequence -continued

```
<220> FEATURE:
<223> OTHER INFORMATION: random peptide library

<400> SEQUENCE: 74

Gly Arg Arg Thr Lys Lys Gln Arg Arg Gln Lys Lys Pro Pro Arg Tyr
1               5                   10                  15

Met Ile Leu Gly Leu Leu Ala Leu Ala Ala Val Cys Ser Ala Ala
            20                  25                  30

<210> SEQ ID NO 75
<211> LENGTH: 14
<212> TYPE: PRT
<213> ORGANISM: Artificial Sequence
<220> FEATURE:
<223> OTHER INFORMATION: random peptide library

<400> SEQUENCE: 75

Gly Arg Arg Thr Lys Lys Gln Arg Arg Gln Lys Lys Pro Pro
1               5                   10
```

US 6,881,825 B1

IDENTICATION OF PEPTIDES THAT FACILITATE UPTAKE AND CYTOPLASMIC AND/OR NUCLEAR TRANSPORT OF PROTEINS, DNA AND VIRUES

This application claims the benefit of Provisional Ser. Nos. 60/151,980 filed Sep. 1, 1999; and 60/188,944 filed Mar. 13, 2000.

FIELD OF THE INVENTION

The present invention relates to peptides which facilitate the delivery, uptake and transport of proteins, DNA and viruses into the cytoplasm and/or nuclei of cells as well as methods for the identification of Such peptides.

BACKGROUND OF INVENTION

The ability to deliver nucleic acids, amino acids, small molecules, viruses, etc. (hereafter referred to collectively as "cargo") to specific cell types is useful for various applications in oncology, developmental biology, gene therapy and in the general understanding of the mode of operation of particular proteins, nucleic acids and small molecules in a model system. There are a number of viral and nonviral delivery systems which have been developed, including vectors derived from human adenoviruses, herpes simplex viruses, adeno-associated viruses, retroviruses (Mulligan, 1993, Science 260:926–932; Berns and Giraud, 1995, Ann. N.Y. Acad. Sci. 772:95–104; Smith, 1995, Ann. Rev. Microbiol. 49:807–838) and others. Nonviral delivery systems include liposomes and conjugates of plasmid and/or DNA with agents designed to facilitate recognition of specific cell surface receptors and protect the newly introduced intracellular DNA from degradation (Wu and Wu, 1987, J. Biol. Chem. 262:4429–4432; Curiel et al., 1991, Proc. Natl. Acad. Sci. 88:8850–8854; Wagner et al., 1992, Proc. Natl. Acad. Sci. 89:6099–6103; Zatloukal et al. 1993, Gene 135:199–207; Douglas et al., 1996, Bio/Technology 14:1574–1578; Zeigler et al., 1996, Transplantation 61:812–817; Felgner, 1997, Sci. Am. 276:102–106).

The cell recognition specificity of viruses and viral vectors is generally very high, and their ability to transfer genetic material into a target cell makes them particularly attractive candidates for the delivery of cargo to a target cell. However, there are potential risks and limitations associated with the use of viral vectors for the delivery of cargo, such as the possibility of integration into a host genome by retroviral vectors, and adverse host reactions (e.g. immunological reactions) against other viral vectors, such as adenovirus. See, e.g. Yang et al., 1995, J. Virol. 69:2004–2015.

Receptor-mediated endocytosis is widely exploited in experimental systems as a natural pathway for the targeted delivery of cargo. Endocytic pathways have been used for selective delivery of therapeutic and other biologically active agents to specific cells and to particular intracellular compartments. See generally, Shen et al., 1992, Adv. Drug. Deliv. Rev., 8:93–113; Kato and Sugiyama, 1997, Crit. Rev. Ther. Drug. Carrier Syst. 14:287–331. In theses systems, ligands to cell-specific receptors are either conjugated to cargo, for example, macromolecules (Vitetta et al., 1993, Immunol. Today 14:252–259; Kuzel and Rosen, 1994, Curr. Opin. Oncol. 6:622–626), liposomes (Kirpotin et al., 1997, Biochemistry 36:66–75; Spragg et al., 1997, Proc. Natl. Acad. Sci. USA 04:8795–8800), radioisotopes or toxins (Fitzgerald, 1996, Semin. Cancer Biol. 7:87–95) and synthetic gene complexes (Wu and Wu, 1993, Adv. Drug Deliv. Rev. 12:159–167), or expressed on the surface of viral transfection vehicles (Kozarsky and Wilson, 1993, Curr. Opin. Genet. Dev. 3:49–503; Wickham et al., Gene Ther. 2:750–756).

Early in the development of receptor-mediated delivery strategies, a ligand was used, together with a polycation (such as polylysine) for the targeting of a condensed DNA to a cell where the ligand was specific for a particular cell surface receptor. See Wu and Wu, 1987, J. Biol. Chem. 262:4429–4432; Wu and Wu, 1988, J. Biol. Chem. 263:14621–14624; Wu and Wu, 1989, J. Biol. Chem. 264:16985–16987. These strategies suffered from the inability of the DNA to be efficiently released into the cytoplasm, although internalization was successful. The addition of endosomolytic agents, such as adenovirus, improved upon the problems associated with ligand/polycation conjugates, however simplified systems were desired. See generally, Cotton and Wagner in The Development of Human Gene Therapy 265 (Cold Spring Harbor Press, Cold Spring Harbor, N.Y. 1999).

The identity of cellular receptors and the mode of their interaction with a ligand-presenting vehicle determine the cell specificity of the delivery system and the intracellular localization of the transported molecules. See Shen et al., 1992, Adv. Drug. Deliv. Rev. 8:93–113 and Basu, 1990, Biochem Pharmacol. 40:1941–1946. This information is useful in the development of simplified methods for delivery. However, these methods are limited by the ability to transfer sufficient quantities of the molecules to specific cells in vivo, although they have proven effective in vitro. Sato et al., 1996, Adv. Drug. Deliv. Rev. 19:445–467. The application of these methods in vivo are limited by several factors, principally the low targeting efficiency of receptor-mediated delivery systems.

Another simplified synthetic system utilized short synthetic peptides based on the sequence thought to be important for membrane fusion by influenza hemagglutinin (Wagner et al., 1992. Proc. Natl. Acad. Sci. 89:7934–7938). The inclusion of these peptides into condensed-DNA complexes allowed for improved simplified delivery of the DNA to a cell. However, the limitation of this method was the affinity of the peptide for numerous cell types which also may translate into an inability to transfer sufficient quantities to a specific target cell.

One approach to improving the ability to transfer sufficient quantities of cargo to specific cells is to identify novel cell-targeting ligands, which increase the rate and specificity for the transport of molecules. The first protein discovered having such transduction properties was the HIV transactivator protein, TAT. See Green & Lowenstein, Cell, 55:1179–1188 (1988); Frankel & Paho, (Cell 55:1189–1193 (1988). Subsequently, an 11 amino acid transduction domain in TAT (TAT-PTD) responsible for the observed transduction properties was identified, based on its high basic residue content. See Fawell et al., Proc. Natl. Acad. Sci. USA 91:664–668 (1994). It has been shown that fusion protein constructs containing TAT-PTD are capable of delivering proteins to a wide spectrum of cell types both in vitro and in vivo. See Nagahara et al., Nat. Med. 4:1449–52 (1998); Vives et al., J. Biol. Chem. 272:16010–17 (1997) Shwarze et al., Science 285:1569–72 (1999); Vocero-Akbani et al., Nat. Med. 5:29–33 (1999); Moy et al., Mol. Biotechnol. 6:105–13 (1996). It is not known however if TAT-PTD will be effective in all cells and with all fusion constructs. It is possible that TAT-PTD will elicit an immune response in subjects to which it is administered. See Schwarze & Dowdy, TiPS 21:45–48. Furthermore, the half-life of TAT-PTD may vary in different cells and subjects which could also aderselyeffect its transduction efficiency. See Schwarze & Dowdy, *TiPS* 21:45–48.

In addition, a class of peptides, called penetratins, which have translocating properties and are capable of carrying hydrophilic compounds across the plasma membrane have recently been identified. For example, Derossi et al., 1998, *Trends in Cell Biology* 8:84–87, have isolated a 16 residue peptide (called penetratin-1, Ant PTD, or AntP) possessing translocation properties, corresponding to amino acids 43–58 of the homeodomain of ANTENNAPEDIA, a *Drosophila* transcription factor which is internalized by cells in culture. The 16 residue peptide has translocation properties equivalent to those of the full length homeodomain. Derossi et al. have shown the ability of the 16 residue peptide to intracellularly deliver oligonucleotides and oligopeptides attached thereto. However, this method is limited in that oligonucleotides greater than 55 bases long and oligopeptides greater than 100 amino acids long were not shown to be efficiently delivered. Additionally, the peptide-oligonucleotide and peptide-oligopeptide hybrids may be insoluble. Furthermore, delivery was inhibited by the release by cells (particularly dying cells) of DNA into the extracellular matrix which binds to the peptide and inhibits internalization. These peptides are also susceptible to the problems of specificity and affinity for particular cell types.

Similarly, Villaverde et al. have isolated a short peptide which contains the cell attachment motif of foot and mouth disease virus (FMDV). Villaverde et al., 1998, *Biotechnology and Bioengineering* 59:294–301. This peptide targets a specific receptor and the mechanism of import is also receptor mediated. Villaverde et al. demonstrated that the attachment of the FMDV peptide to β-galactosidase (βgal) facilitated the uptake of βgal into cells in vitro. The attachment of the peptide was either at the n-terminus of βgal or at an internal loop of βgal. Internal attachment provided superior internalization of βgal, and attachment of multiple copies further increased the amount of internalization. This peptide demonstrated varying affinity for different cell lines and therefore is likely to work efficiently with only particular target cells.

Elliot & O'Hare (*Cell* 188:223–233 (1997)) have shown that VP-22, a 38 kDa tegument protein from herpes simplex virus type 1 (HSV-1) also possesses the ability to transduce attached molecules across cell membranes and that residues 267–300 of VP-22 are required, but may not be sufficient, for transduction. Since the region responsible for transduction has not yet been identified, current approaches using VP-22 have been directed to fusing the entire VP-22 protein to a molecule to facilitate the transduction of that molecule. This has several disadvantages including a greater likelihood that the fusion protein (1) will be more readily degraded in cells, (2) will be harder to produce due to solubility problems, and (3) will elicit an immune response in a subject. In addition, there is little data about the efficiency of transduction using VP-22 linked to another molecule. See Schwarze & Dowdy, *TiPS* 21:45–48.

Therefore, there is a need for a simplified, improved delivery means for delivering cargo, such as polypeptides, polynucleotides, small molecules, plasmids and viruses to cells which demonstrates high efficiency transfer of the cargo to a wide variety of cell types. There is also a need for a method for isolating such improved means (e.g. peptides) for the delivery of cargo into a wide variety of cell types at high efficiency.

SUMMARY OF THE INVENTION

The present invention relates to internalizing peptides which are capable of facilitating the delivery, uptake and, where desired, nuclear and/or cytoplasmic transport of cargo (e.g. polynucleotides, polypeptides, small molecules, virus, modified virus, plasmid, etc.) into a target cell. The internalizing peptides of the invention are isolated according to their ability to efficiently internalize and deliver cargo into a wide variety of cell types. The peptides of the invention can facilitate transport from the extracellular milieu to the cytoplasm and/or nucleus in a cell both in vivo and in vitro.

The peptides of the present invention are useful, inter alia, for (1) facilitating the uptake of cargo in a target cell; (2) inducing apoptosis in cells (e.g., arthritic cells, tumor cells, etc); (3) expanding a population of stem cells; (4) expanding a population of differentiated cells; (5) stimulating the differentiation of a population of stem cells; (6) facilitating the integration of AAV DNA into the genome of a cell; (7) facilitating the uptake into a cell, secretion from said cell and subsequent reuptake into a neighboring cell of a protein; (8) facilitating the growth of defective viruses in culture; (9) stimulating the immune response in a subject; (10) facilitating uptake of any GST fusion protein into a cell; (11) eliciting an immune response in a subject; and (12) facilitating the delivery of immunogens (e.g. vaccines), whether protein based, DNA based, vector based or viral based.

The present invention also relates to a method for identifying internalizing peptides which are capable of facilitating the uptake and cytoplasmic and/or nuclear transport of cargo into a target cell. The method comprises (a) incubating a target cell with a peptide display library; (b) isolating internalized peptides presented by said peptide display library from the cells and identifying said internalized peptides; (c) linking said peptides to cargo: (d) incubating said peptide-cargo complex with a target cell; and (c) determining the ability of said peptide to facilitate the uptake and, where desired, cytoplasmic and/or nuclear localization of said cargo into said target cell.

In addition, the present invention provides for immunogens comprising an internalizing peptide of the present invention linked to cargo and for a method of eliciting an immune response in a subject comprising delivering the peptide/cargo complex (i.e. the immunogen) of the present invention to target cells of the subject. In one preferred embodiment of the invention, the immunogen is a vaccine.

BRIEF DESCRIPTION OF THE DRAWINGS

FIGS. 2A and 2C (low and high magnification respectively) shows the ability of peptide 1 (SEQ ID NO:1) to facilitate the uptake of β-gal into rabbit synovial cells and FIGS. 2B and 2D (low and high magnification respectively) shows the ability of peptide 3 (SEQ ID NO:3) to facilitate the uptake of β-gal into rabbit synovial cells.

FIGS. 3A and 3B (high and low magnification respectively) shows the ability of peptide 5 (SEQ ID NO:5) to facilitate the uptake of β-gal in human synovial cells and FIGS. 3C and 3D (high and low magnification respectively) shows the ability of peptide 1 (SEQ ID NO:1) to facilitate the uptake of β-gal in human synovial cells.

FIGS. 6A-I: shows the ability of peptide 5 (SEQ ID NO:5) to facilitate the uptake of β-gal in (A) HIG-82 cells; (B) rabbit primary synovial cells; (C) human primary synovial cells; (D) primary human airway epithelial cells HBE 144; (E) polarized canine kidney cells MDCK; (F) human islet primary cells; (G) murine myoblast cells C2C12; (H) murine fibrosarcoma tumor cells MCA205; and (I) NIH3T3 cells.

DETAILED DESCRIPTION OF THE INVENTION

Figure 1A:
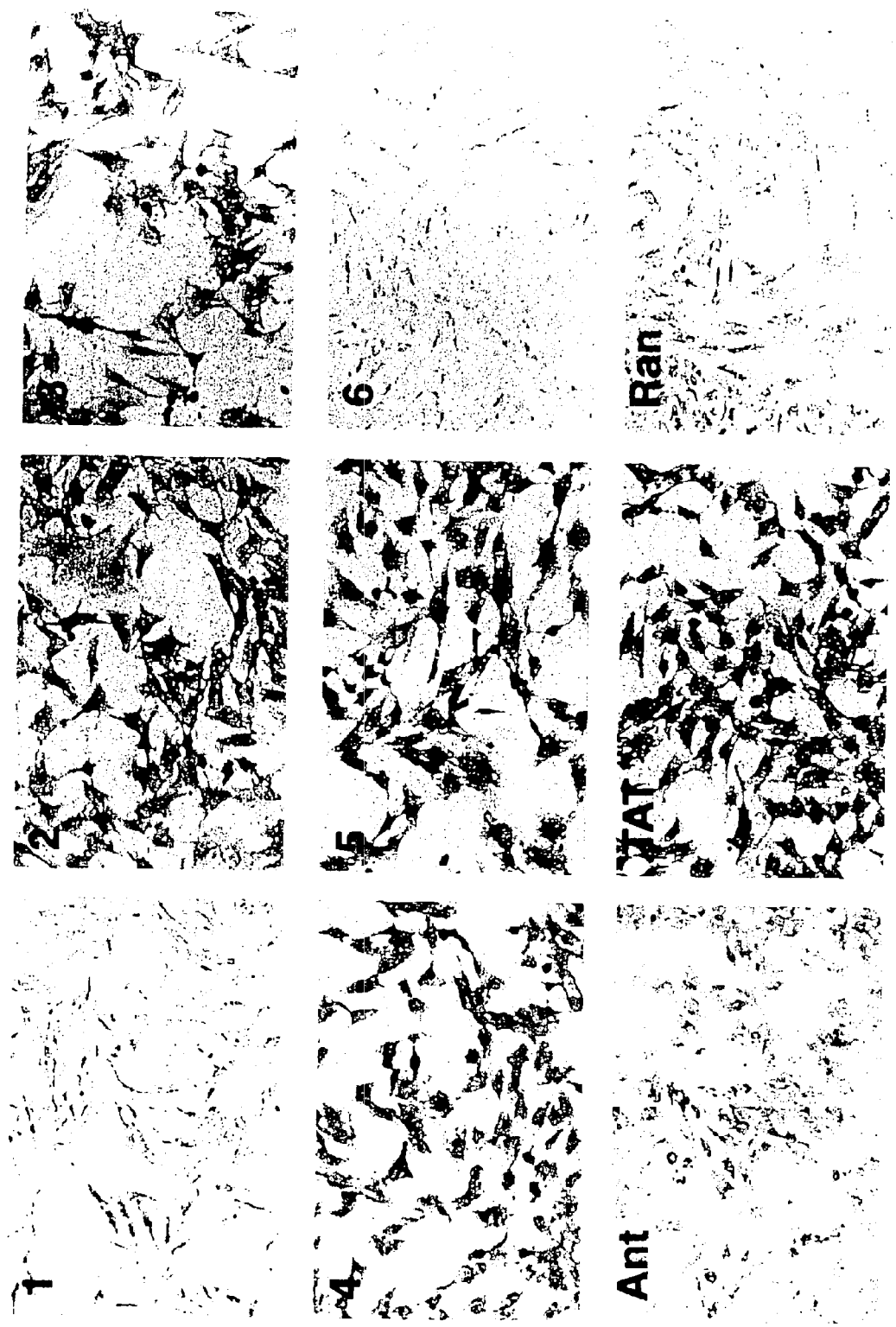
FIGS. 1A&B: (A) shows the ability of peptides 1, 2, 3, 4, 5, 6 of the invention, antennapedia peptide (Ant-PTD), TAT-PTD and a random peptide (SEQ ID NO:1, SEQ ID NO:2, SEQ ID NO:3, SEQ ID NO:4, SEQ ID NO:5, SEQ ID NO:6, SEQ ID NO:19, SEQ ID NO:21 and SEQ ID NO:20 respectively) to facilitate the uptake of βgal, when linked trough a biotin-streptavidin bridge, into HIG-82 cells. (B) Shows the ability of peptides 2, 3, 4, 5, antennapedia peptide, TAT-PTD, a random peptide (SEQ ID NO:2, SEQ ID NO:3, SEQ ID NO:4, SEQ ID NO:5, SEQ ID NO:19, SEQ ID NO:21 and SEQ ID NO:20 respectively) and β-gal alone to facilitate the uptake of βgal into HIG-82 cells at differing concentrations (1:1=150 nM of βgal).

The peptides of the present invention facilitate the delivery, internalization and also, where desired, the cytoplasmic and/or nuclear transport of cargo into a wide variety of cell types. The delivery of cargo to a target cell is useful for various applications in gene therapy, oncology, developmental biology, the treatment of disease, immunogens, vaccines (i.e. eliciting an immune response) as well as for the general study of the mode of operation and the function of proteins, nucleic acids and small molecules in a model system. For example, a small molecule drug may be delivered to a cell via the peptides of the present invention, either in vitro or in vivo to study the effect of the drug on the cell (e.g. to see whether the drug induces apoptosis). Such delivery of small molecule drugs are useful for treating a wide variety of diseases, including arthritis and cancer. Additionally, a macromolecule or macromolecule complex, such as a protein, DNA, RNA, antisense RNA, virus, viral or non-viral vector etc., may be delivered to a cell via the peptides of the present invention, either in vitro or in vivo for the purpose of studying the effects of said macromolecule or macromolecular complex on the cell or to treat or otherwise affect a disease in a recipient requiring said macromolecule or macromolecular complex. For example, a macromolecule representing an apoptotic protein (e.g. the apoptotic protein itself or a DNA encoding the apoptotic protein or a peptide with apoptotic properties) may be delivered to synovial cells in arthritic joints or tumor cells to induce apoptosis therein.

Model systems may include in vitro systems such as eukaryotic and prokaryolic cell cultures, which can allow for the identification of the various components involved in a particular biological pathway, the understanding of how a particular gene may be expressed or how expression of a particular gene may be amplified and/or made persistent, the determination of the function of a protein and how it may be inhibited, the determination of the function, activity and mode of action of certain small molecules, as well as the feasibility of transfer into a cell of particular cargo.

Model systems may also include animal model systems, which may aid in the development of drugs for particular diseases, the determination of the efficacy of the up or down-regulation of particular gene products in vivo and the resultant advantages or disadvantages of such regulation and the determination of the efficacy of the delivery of proteins in vivo and whether such delivery is efficient and effective for gene therapy or as a vaccine, etc. Such information may give insight in the application of such methods in oncology, developmental biology, gene therapy and vaccine development and may lead to new developments and a greater understanding of disease and the treatment of disease, such as, but not limited to, the treatment of arthritis and cancer.

The peptides of the present invention are useful, inter alia, for (1) facilitating the uptake of cargo in a target cell; (2) inducing apoptosis in cells (e.g., arthritic cells, tumor cells, etc); (3) expanding a population of stem cells; (4) expanding a population of differentiated cells; (5) stimulating the differentiation of a population of stem cells; (6) facilitating the integration of AAV DNA into the genome of a cell; (7) facilitating the uptake into a cell, secretion from said cell and subsequent reuptake into a neighboring cell of a protein; (8) facilitating the growth of defective viruses in culture; (9) stimulating the immune response in a subject; (10) facilitating uptake of any GST fusion protein, (11) eliciting an immune response in a subject; and (12) facilitating the delivery of immunogens (e.g. vaccines), whether protein based, DNA based, vector based or viral based.

In one embodiment, the present invention includes a complex comprising (a) an internalizing peptide and (b) cargo. As used herein, a complex can be defined as two or more molecules linked together by any physical means. The complex may be tightly or weakly linked together in a highly specific or totally non-specific way. The internalizing peptides of the present invention when linked to cargo facilitate the cellular uptake of cargo. As used herein, the term "link" refers to any covalent cross-linkage or non-covalent linkage (e.g. a fusion protein comprising the peptide and another protein) wherein said linkage is between the peptide of the present invention and a cargo.

As used herein, "internalizing peptide" is a peptide that has been selected for its ability to locate and enter a wide variety of cell types. Additionally, the internalizing peptides of the invention may translocate into the nucleus if the cell. Furthermore the internalizing peptides of the invention are capable of translocating and delivering cargo into a cell when linked to said cargo. The peptides of the present invention are positively charged and amphipathic and may interact with negative charges on the surface of the cellular bilayer membrane.

The internalizing peptides of the present invention may be complexed with cargo. The term "cargo", as used herein, refers to any small molecule, macromolecule, or macromolecular complex which may be useful to transfer to a cell. Cargo includes, but is not limited to, small molecules, polynucleotides, DNA, oligonucleotide decoys, antisense RNA, polypeptides, proteins, viruses, modified viruses, viral and non-viral vectors and plasmids. Small molecules may be therapeutically useful and may include drugs or other agents which act to ensure proper functioning of a cell or molecules which may induce apoptosis or cell lysis, where death of a cell, such as a cancerous cell, is desired. Nucleic acids may code for, inter alia, a protein, RNA, ribozyme, or antisense RNA. The protein, RNA or ribozyme encoded by the encoded acid may be under-represented, defunct or non-existent in the cell and the antisense RNA encoded by the nucleic acid may allow for the elimination of an undesired function of a molecule. Decoy oligonucleotides may contain specific binding sites for transcription factors and may block the function of the transcription factors in vitro and in vivo. Where the cargo is a polypeptide, the polypeptide may be a peptide or protein which, when delivered to the cell, provides a desired function to the cell or induces a particular phenotypic alteration or the protein or peptide may be an antigen capable of eliciting an immune response in the cell.

Amino acid residues in peptides are herein abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

The internalizing peptides of the present invention have been selected for their ability to be internalized into a wide variety of target cells. The internalizing peptides of the present invention obtained by M13 phage library screening with HIG-82 cells are listed below in Table 1. The internalizing peptides of the present invention obtained by M13 phage library screening with human primary T cells are listed below in Table 2. The internalizing peptides of the present invention obtained by M13 phage library screening with Calu 3 cells (human epithelial cell line) are listed below in Table 3. The internalizing peptides of the present invention obtained by M13 phage library screening with surgically resected cervical mucosa tissue from human patients are listed below in Table 4. In addition, the internalizing peptides of the present invention may be identified by fusion of an internalizing peptide of the present invention with another peptide with a desired function such as, for example, but not by way of limitation, fusion of an internalizing peptide to a previously identified ubiquitin targeting peptide which may have the amino acid sequence GVVGKLGQRRTKKQRRQKK (the "UBI" peptide) as set forth by SEQ ID NO:73 or fusion of an internalizing peptide with an endoplasmaticum reticulus (ER) localization signal such as adenovirus E19 sequence which may have the amino acid sequence GRRTKKQRRQKKPPRYMILGLLALAAVCSAA as set forth by SEQ ID NO:74. In addition, the internalizing peptide of the present invention may have the amino acid sequence GRRTKKQRRQKKPP (SEQ ID NO:75).

Any technique known to those in the art may be employed to identify peptides with high efficiency of internalization for a target cell. In one preferred embodiment of the invention, phage biopanning has employed to select for peptides (Table 1, 2, 3 and 4) which are internalized into such cell lines as Hig-82 cells, human synovial cells, rabbit synovial cells, human primary airway HBE144 cells, primary human islet cells, murine myoblast C2C12 cells, dog kidney epithelial MDCK cells, murine tumor MCA 205 cells, murine tumor MC38 cells (all shown in FIG. 6) and rabbit synovial lining (FIG. 4). In addition, the internalizing peptides are internalized into mucosa, such as cervical mucosa (see FIG. 22, and Example 2 and 9 below). In another preferred embodiment, the internalizing peptides of the present invention can be fused to another peptide with a desired function (e.g. ubiquitin targeting or ER localization functions) such as the internalizing peptides set forth by SEQ ID NOs:73 and 74 which are also internalizing into a wide variety of cells including, but not limited to Hig-82 cells, human synovial cells, rabbit synovial cells, human primary airway HBE144 cells, primary human islet cells, murine myoblast C2C12 cells, dog kidney epithelial MDCK cells, murine tumor MCA 205 cells, murine tumor MC38 cells, rabbit synovial lining, and mucosa, such as cervical mucosa (see FIG. 22, and Example 2 and 9 below)

TABLE 1

| | | | |
|---|---|---|---|
| 1) | peptide 1 (pep1) | KRIIQRILSRNS | (SEQ ID NO:1) |
| 2) | peptide 2 (pep2) | KRIHPRLTRSIR | (SEQ ID NO:2) |
| 3) | peptide 3 (pep3) | PPRLRKRRQLNM | (SEQ ID NO:3) |
| 4) | peptide 4 (pep4) | PIRRRKKLRRLK | (SEQ ID NO:4) |
| 5) | peptide 5 (pep5) | RRQRRTSKLMKR | (SEQ ID NO:5) |
| 6) | peptide 6 (pep6) | MHKRPTTPSRKM | (SEQ ID NO:6) |
| 7) | peptide 7 (pep7) | RQRSRRRPLNIR | (SEQ ID NO:7) |
| 8) | peptide 8 (pep8) | RIRMIQNLIKKT | (SEQ ID NO:8) |
| 9) | peptide 9 (pep9) | SRRKRQRSNMRI | (SEQ ID NO:9) |
| 10) | peptide 10 (pep10) | QRIRKSKISRTL | (SEQ ID NO:10) |
| 11) | peptide 11 (pep11) | PSKRLLHNNLRR | (SEQ ID NO:11) |
| 12) | peptide 12 (pep12) | HRHIRRQSLIML | (SEQ ID NO:12) |
| 13) | peptide 13 (pep13) | PQNRLQIRRHSK | (SEQ ID NO:13) |
| 14) | peptide 14 (pep14) | PPHNRIQRRLNM | (SEQ ID NO:14) |
| 15) | peptide 15 (pep15) | SMLKRNHSTSNR | (SEQ ID NO:15) |
| 16) | peptide 16 (pep16) | GSRHPSLIIPRQ | (SEQ ID NO:16) |
| 17) | peptide 17 (pep17) | SPMQKTMNLPPM | (SEQ ID NO:17) |

TABLE 1-continued

| | | | |
|---|---|---|---|
| 18) | peptide 18 (pep18) | NKRILIRIMTRP | (SEQ ID NO:18) |
| 19) | peptide 19 (pep19) | HGWZIHGLLHRA | (SEQ ID NO:25) |
| 20) | peptide 20 (pep20) | AVPAKKRZKSV | (SEQ ID NO:26) |
| 21) | peptide 21 (pep21) | PNTRVRPDVSF | (SEQ ID NO:27) |
| 22) | peptide 22 (pep22) | LTRNYEAWVPTP | (SEQ ID NO:28) |
| 23) | peptide 23 (pep23) | SAETVESCLAKSH | (SEQ ID NO:29) |
| 24) | peptide 24 (pep24) | YSHIATLPFTPT | (SEQ ID NO:30) |
| 25) | peptide 25 (pep25) | SYIQRTPSTTLP | (SEQ ID NO:31) |
| 26) | peptide 26 (pep26) | AVPAENALNNPF | (SEQ ID NO:32) |
| 27) | peptide 27 (pep27) | SFHQFARATLAS | (SEQ ID NO:33) |
| 28) | peptide 28 (pep28) | QSPTDFTFPNPL | (SEQ ID NO:34) |
| 29) | peptide 29 (pep29) | HFAAWGGWSLVH | (SEQ ID NO:35) |
| 30) | peptide 30 (pep30) | HIQLSPFSQSWR | (SEQ ID NO:36) |
| 31) | peptide 31 (pep31) | LTMPSDLQPVLW | (SEQ ID NO:37) |

TABLE 2

| | | | |
|---|---|---|---|
| 1) | peptide 32 (pep32) | FQPYDHPAEVSY | (SEQ ID NO:38) |
| 2) | peptide 33 (pep33) | FDPFFWKYSPRD | (SEQ ID NO:39) |
| 3) | peptide 34 (pep34) | FAPWDTASFMLG | (SEQ ID NO:40) |
| 4) | peptide 35 (pep35) | FTYKNFFWLPEL | (SEQ ID NO:41) |
| 5) | peptide 36 (pep36) | SATGAPWKMWVR | (SEQ ID NO:42) |
| 6) | peptide 37 (pep37) | SLGWMLPFSPPF | (SEQ ID NO:43) |
| 7) | peptide 38 (pep38) | SHAFTWPTYLQL | (SEQ ID NO:44) |
| 8) | peptide 39 (pep39) | SHNWLPLWPLRP | (SEQ ID NO:45) |
| 9) | peptide 40 (pep40) | SWLPYPWHVPSS | (SEQ ID NO:46) |
| 10) | peptide 41 (pep41) | SWWTPWHVHSES | (SEQ ID NO:47) |
| 11) | peptide 42 (pep42) | SWAQHLSLPPVL | (SEQ ID NO:48) |
| 12) | peptide 43 (pep43) | SSSIFPPWLSFF | (SEQ ID NO:49) |
| 13) | peptide 44 (pep44) | LNVPPSWFLSQR | (SEQ ID NO:50) |
| 14) | peptide 45 (pep45) | LDITPFLSLTLP | (SEQ ID NO:51) |
| 15) | peptide 46 (pep46) | LPHPVLHMGPLR | (SEQ ID NO:52) |
| 16) | peptide 47 (pep47) | VSKQPYYMWNGN | (SEQ ID NO:53) |

TABLE 3

| | | | |
|---|---|---|---|
| 1) | peptide 48 (pep48) | NYTTYKSHFQDR | (SEQ ID NO:54) |
| 2) | peptide 49 (pep49) | AIPNNQLGFPFK | (SEQ ID NO:55) |
| 3) | peptide 50 (pep50) | NIENSTLATPLS | (SEQ ID NO:56) |
| 4) | peptide 51 (pep51) | YPYDANHTRSPT | (SEQ ID NO:57) |
| 5) | peptide 52 (pep52) | DPATNPGPHFPR | (SEQ ID NO:58) |
| 6) | peptide 53 (pep53) | TLPSPLALLTVH | (SEQ ID NO:59) |
| 7) | peptide 54 (pep54) | HPGSPFPPEHRP | (SEQ ID NO:60) |
| 8) | peptide 55 (pep55) | TSHTDAPPARSP | (SEQ ID NO:61) |
| 9) | peptide 56 (pep56) | MTPSSLSTLPWP | (SEQ ID NO:62) |
| 10) | peptide 57 (pep57) | VLGQSGYLMPMR | (SEQ ID NO:63) |

TABLE 4

| | | | |
|---|---|---|---|
| 1) | peptide 58 (pep58) | QPIIITSPYLPS | (SEQ ID NO:64) |
| 2) | peptide 59 (pep59) | TPKTMTQTYDFS | (SEQ ID NO:65) |
| 3) | peptide 60 (pep60) | NSGTMQSASRAT | (SEQ ID NO:66) |
| 4) | peptide 61 (pep61) | QAASRVENYMHR | (SEQ ID NO:67) |
| 5) | peptide 62 (pep62) | HQHKPPPLTNNW | (SEQ ID NO:68) |
| 6) | peptide 63 (pep63) | SNPWDSLLSVST | (SEQ ID NO:69) |
| 7) | peptide 64 (pep64) | KTIEAHPPYYAS | (SEQ ID NO:70) |
| 8) | peptide 65 (pep65) | EPDNWSLDFPRR | (SEQ ID NO:71) |
| 9) | peptide 66 (pep66) | HQHKPPPLTNNW | (SEQ ID NO:72) |

Of the peptides of Table 4, three have homology to known proteins. Pep63 (SEQ ID NO:69) is homologous to a bacterial protein methenyl tetrahydromethanopterin cyclohydrolase of xanthobacter autotrophicus (Genbank Accession Number AF139593). Pep65 (SEQ ID NO:71) is homologous to a yeast hypothetical protein in the MPP10-SAG1 intergenic region of *Saccharomyces cerevisiae* (Genbank Accession Number NP012536.1). Additionally, pep66 (SEQ ID NO:72) is homologous to herpesvirus 1 nuclear antigen protein (Genbank Accession Number P33485).

Additionally, any nucleotide sequences which encode the peptides represented by SEQ ID NOs:1–18 and 25–72 of the present invention are also contemplated by the present invention.

The internalizing peptides of the present invention are cationic (positively charged) as are TAT-PTD and antennapedia peptide (Ant-PTD). Table 5 below indicates the positive nature of pep 1–6 (SEQ ID NO:1–6), TAT-PTD (SEQ ID NO:21), Ant-PTD (SEQ ID (NO:19) and a random control peptide (SEQ ID NO:20). Peptides 1–6 are all positively charged and enriched for lysine and arginine residues (Table 5 below).

TABLE 5

| Peptide | SEQ ID NO. | Length | MW | Lys + Arg/L |
|---------|------------|--------|---------|-------------|
| Pep 1   | SEQ ID NO:1  | 12 | 1482.81 | 0.333 |
| Pep 2   | SEQ ID NO:2  | 12 | 1531.88 | 0.417 |
| Pep 3   | SEQ ID NO:3  | 12 | 1563.94 | 0.417 |
| Pep 4   | SEQ ID NO:4  | 12 | 1619.81 | 0.667 |
| Pep 5   | SEQ ID NO:5  | 12 | 1614.98 | 0.583 |
| Pep 6   | SEQ ID NO:6  | 12 | 1468.80 | 0.333 |
| Random  | SEQ ID NO:20 | 12 | 1280.40 | 0.167 |
| TAT-PTD | SEQ ID NO:21 | 11 | 1558.63 | 0.727 |
| Ant-PTD | SEQ ID NO:19 | 16 | 2245.78 | 0.438 |

Where desired, the internalizing peptides of the present invention may also facilitate the nuclear translocation of cargo.

The usefulness of the present invention may be demonstrated, for example, by incubating a complex comprising an internalizing peptide linked to cargo with target cells and measuring the efficiency of transfer of the peptide-cargo complex to the target cell. In one embodiment, the selected internalizing peptide was biotinylated and coupled to streptavidin-labeled β-galactosidase (the "cargo"). The ability of the internalizing, peptide to internalize β-gal into a cell was established by adding X-gal to cells, which when in the presence of β-gal is cleaved and gives a blue color. Cells which stained blue indicated that β-gal had successfully been transferred to the cells via the peptides of the present invention (FIG. 1-6 and 12) (see Example 4 below). In addition, a polynucleotide encoding one of the peptides (peptide 5; SEQ ID NO:5) was subcloned with nucleic acid encoding eGFP (green flourescent protein) to produce a peptide-eGFP fusion, expressed and purified from bacteria. Peptide 5, when fused to eGFP, facilitated the internalization of eGFP into cells (see FIG. 9), which was directly monitored by fluorescence microscopy.

In a preferred embodiment of the invention, the internalizing peptides which allow for the co-entry of peptide-linked cargo, and the translocation of the cargo to the nuclei are pep 2 (SEQ ID NO:2), pep 3 (SEQ ID NO:3), pep 4 (SEQ ID NO:4), pep5 (SEQ ID NO:5) shown in Table 1 above, and UBI (SEQ ID NO:73). The internalizing peptides of the present invention may be linked to cargo by any method known to those in the art, such as, but not limited to chemical cross-linking, avidin bridge, glutathione-S-transferase bridge, peptide-cargo fusion protein, etc. The peptides of the present invention may also be synthesized as a fusion with a peptide nucleic acid (PNA) which is a DNA mimic capable of forming double and triple helices with DNA (see Knudsen and Nielsen, 1997, *Anticancer Drugs* 8:113–118). This peptide-PNA fusion can form a stable DNA or RNA/PNA duplex (Branden et al., 1999, *Nat. Biotechnol.* 17:784–787) which may enter cells via the peptides of the present invention, thereby delivering DNA or RNA to a target cell.

Additionally, the ability of the internalizing peptide to carry the cargo into the cell may be measured by the presence of functional cargo in the cell (e.g. the presence of β-gal may be demonstrated by the ability of the cell to cleave X-gal and give a blue color; the presence of cystic fibrosis transmembrane regulator (CFTR) protein may be demonstrated by the presence of a functional chloride ion channel in a cell originally lacking CFTR, and the presence of an apoptotic factor may be shown by the apoptosis of cells after the administration of a peptide-apoptosis factor construct of the present invention). The cargo (e.g. polypeptide, polynucleotide, small molecule, virus, plasmid) may be labeled by a method known in the art (e.g. radiolabeling or fluorescent labeling) and the presence of the label would establish the efficient delivery of the cargo into the target cell by the internalizing peptide. In addition, the presence of an immunogen in the cell of a subject may be measured by the ability to elicit an immune response in a subject.

To establish nuclear translocation of the internalizing peptides themselves and the ability of the internalizing peptide to transfer a small molecule linked thereto to a cell, the peptides were labeled with streptavidin-Cy3, a fluorescent marker (see Example 4 below). Using confocal microscopy, the ability of the peptide to translocate to the nucleus is determined. Other methods known in the art of establishing the presence of a peptide in the cytoplasm or nucleus of a cell are also contemplated by the present invention (e.g. labeling of the peptide with a radioisotope, a flourescent marker or a dye).

The internalizing peptides of the present invention facilitate uptake and delivery into a wide variety of cell types (see FIGS. 1-4 and 6) including cells which are refractory to virus infection, such as primary human airway epithelial cells (FIG. 6), as well as other types of primary and established cell lines, such as Hig-82 cells (a rabbit synovial cell line established by Christopher Evans, University of Pittsburgh, ATCC Deposit No. CRL-1832), rabbit synovial cells, human synovial cells, primary human islet cells, murine myoblast cells, dog kidney epithelial cells, murine fibroblast cells, and murine tumor cells (FIGS. 1-4 and 6) (see Examples 4 and 5 below), cells of different germal layers, as well as mucosa, such as cervical mucosa (FIG. 22).

The peptides of the present invention are also useful for delivery of cargo into cells in vivo and can facilitate in sutu or localized delivery of cargo in vivo (see FIG. 4 and Example 3 below). In one embodiment, a biotinylated peptide-streptavidin-β-gal complex was injected into synovial lining (knee joint) of rabbits which was then harvested. The harvested synovial lining was then incubated with X-gal to show that the peptide facilitated the uptake of β-gal by synovial lining cells in vivo. Ghivizzani et al. (*J. Immunol.* 159:3604 (1997) have described using the synovial lining of rabbits as a model system for studying arthritis (see also Nita et al., *Arthritis Rheum* 39:820 (1996); Ghivizzani et al., *Proc. Natl. Acad. Sci. USA* 95:4613 (1998); and Ghivizzani et al., *Gene Ther.* 4:977 (1997). Rheumatoid arthritis is correlated with an excessive proliferation of synovial cells and an apparent defect in synovial cell death that would ordinarily reduce the synovial cell number. Because the peptides of the present invention can facilitate the uptake of cargo into synovial lining cells in vivo, the peptides are useful in the alleviation of arthritis. One approach to alleviating rheumatoid arthritis in a subject is to induce synovial cell death. See Wakisaka et al., *Clin. Exp. Immunol.* 114:119–128 (1998); Sakai et al., *Arthritis Rheum.* 41:1251–1257 (1998).

The peptides of the present invention, as well as TAT-PTD, can induce apoptosis in rheumatoid arthritis synovial cells when linked to an apoptosis factor. For example, the peptides of the present invention, as well as TAT-PTD, when linked to an apoptosis factor (e.g. p53; caspase-3; an antimicrobial peptide such as KLAKLAK (SEQ ID NO:22) and KLAKLAKKLAKLAK (SEQ ID NO:23), which disrupts the mitochondrial membrane once inside a cell (see Ellerby et al., *Nat. Med*. 5:1032 (1999); are useful for delivering the apoptosis factor, or a DNA encoding an apoptosis factor, to arthritic joints and inducing apoptosis therein (see FIG. 18 and Example 7 below). In addition, the peptides of the present invention, as well as TAT-PTD, are useful for delivering apoptosis factors to tumor cells and inducing apoptosis therein. The induction of apoptosis in tumor cells is useful for the destruction of the tumor cell and for increasing the efficacy of drugs designed to treat cancer which are ineffective in tumor cells resistant to apoptosis. See Brown and Wouters, *Cancer Res*. 59:1391–1399 (1999); Yamabe et al., *Gene Ther*. 6:1952–1959 (1999). When the antimicrobial peptide, KLAKLAKKLAKLAK (SEQ ID NO:23), is coupled to the peptides of the present invention or TAT-PTD (e.g. the "death peptide"=peptide 5, SEQ ID NO:5, a linker and KLAKLAKKLAKLAK (SEQ ID NO:23) resulting in RRQRRTSKLMKRGGKLAK-LAKKLAKLAK (SEQ ID NO:24)) and administered to HIG 82 cells, apoptosis was induced in the cells (see FIGS. 14 and 15 and Example 7 below). Furthermore, when the "death peptide" was intra-tumorally injected subcutaneously into day 7–14 MCA205 (a murine fibrosarcoma cell line) established tumors in mice (the following references describe using MCA205 cells to establish tumors in mice for a model system for studying cancer: Hiroishi et al., *Cell Ther*. 6:1988 (1999); Osaki et al., *Gene Ther*. 6:808 (1999); Nishioka et al., *Cancer Res*. 59:4035 (1999); Gambotto et al., *Cancer Gene Ther*. 6:45 (1999); Kim et al., *Cancer Immunol Immunother*. 47:257 (1999); Mangency and Heidmann, *Proc. Natl. Acad. Sci. USA* 95:14920 (1998); Noffz et al., *J. Immunol*. 160:345 (1998); Osaiki et al., *J. Immunol*. 160:1742 (1998); Cayeux et al., *J. Immunol*. 158:2834 (1997); Ohno et al., *J. Immunol*. 156:3875 (1996)), there was shrinkage of the tumor with significant apoptosis/necrosis, especially in the middle of the tumor (see FIG. 16A, 16B, 16C and Example 7 below).

As noted above, the internalizing peptides of the present invention are useful for delivering and internalizing other apoptotic factors as well, including p53. When p53 was fused to pep5 (SEQ ID NO:5), the p53 was effectively internalized into a rabbit synovial cell line (Hig-82) and able to induce p21 promoter driven luciferase expression from a reporter plasmid therein (see FIG. 20 and Example 7 below). The pep5-p53 complex was similar in its ability to induce reporter plasmid expression as a plasmid which expresses p53 and much more effective than an adenovirus vector expressing p53 (see FIG. 20 and Example 7 below). Due to its apoptotic abilities, the internalizing peptide-p53 complex of the present invention is useful in the treatment of cancer and arthritis and may be administered to a subject, for example, by either local or systemic injection (such as intra-tumoral injection or intra-articular injection).

The "death peptide" is also useful for the induction of apoptosis in other cells, including synovial lining cells. When the death peptide was injected in the arthritic rabbit knees, it mediated apoptosis of the hyperplastic synovium (see FIG. 18 and Example 7 below). Internalization of apoptosis factors using the peptides of the present invention and TAT-PTD is advantageous since cellular uptake of cargo mediated by the peptides of the present invention is more efficient than viral vector mediated gene transfer or the commercially available antennapedia peptide (Example 3 and FIG. 4A).

Figure 19:
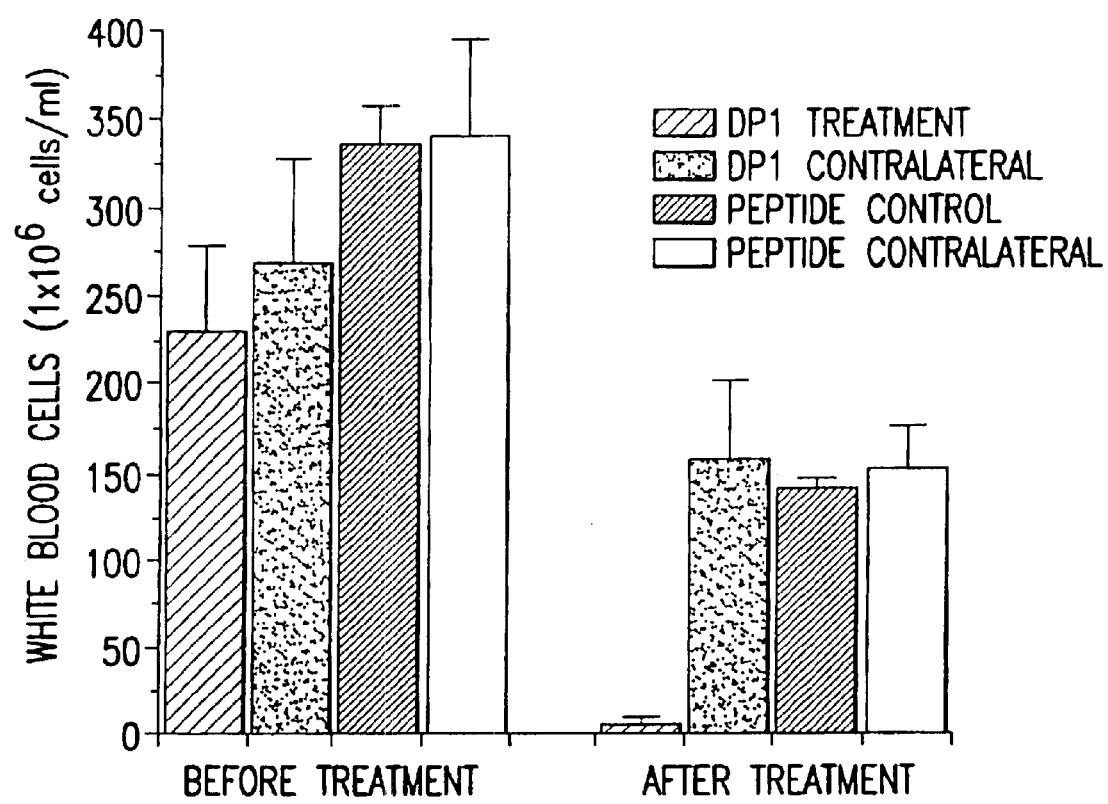
FIG. 19 is a bar graph showing that the death peptide (SEQ ID NO;24; DP1) causes great reduction of white blood cells in lavage fluid of IL1 inflamed rabbit joints.

Rheumatoid arthritis (RA) is a chronic inflammatory disease which is characterized by hyperplasia of the synovial lining of cells, angiogenesis, and infiltration of mononuclear cells resulting in pannus formation, cartilage erosion and ultimately joint destruction. Most of articular cartilage consists of collagens and proteoglycans whose degradation is initiated extra- or peri-cellularly by proteinases produced locally by cells in and around the joint. See Evans, *Agents Actions Suppl*. 32:135–152 (1991). Proteinases, and particularly serine proteinases and neutral mettaloproteinases, are involved in the degradation of articular cartilage. Mesenchynial cells of the joint and white blood cells which colonize the joint during the inflammatory response synthesize various proteinases which degrade articular cartilage. Therefore, reduction of white blood cells at the site of inflammation in arthritic joints is an approach to anti-crosive therapy in arthritis. The internalizing peptides of the present invention are useful in delivering apoptotic factors to cells in arthritic joints, including white blood cells in lavage fluid of inflamed arthritic joints. FIG. 19 shows that injection of the death peptide (SEQ ID NO:24; DP1) into inflamed rabbit joints causes a great reduction of the number of white blood cells in the lavage fluid of IL-1 inflamed rabbit joints (sea also Example 7 below). White blood cell reduction is useful to reduce swelling synovial proliferation and cartilage degradation in arthritic joints.

Delivery of apoptosis factors via the peptides of the present invention is rapid and potent. For example, low concentrations of the death peptide (SEQ ID NO:24) are required to mediate cell death. In one embodiment of the invention, cell death may be mediated by the internalizing peptides of the present invention (SEQ ID NOs:1–18 and 25–72) linked to cargo comprising an apoptosis factor wherein the concentration administered to cells is between 1 $\mu$M and 1 mM. In a preferred embodiment of the present invention, the concentration of the peptide+cargo administered to cells is between 10 $\mu$M and 100 $\mu$M.

In another aspect of the invention, the immune response against tumors may be augmented by co-administration of the internalizing peptides of the present invention linked to a cargo (e.g. apoptosis factor) with cytoklines and other activating molecules (e.g. Flt-3). The cytokines and other activating molecules may be administered to cells via the peptides of the present invention or by any other conventional means of administration known to those of skill in the art.

Additional potential applications for the peptides of the present invention when linked to cargo comprising an apoptosis factor may include the treatment of accessible head and neck tumors, papillomas and other solid tumors, or as an adjuvant therapy in conjunction with radiotherapy, standard chemotherapy or surgical debulking to extend excision margins.

The peptides of the present invention are also useful for developing improved immunogens. For example, the peptides of the present invention may facilitate delivery of, inter alia, proteins, polypeptides, DNA, RNA, vectors, and viruses to target cells in a subject which may be useful as immunogens. The peptide/cargo complexes of the present invention are capable of eliciting an immune response when administered to a target cell of a subject. In one embodiment of the invention, the immunogens are vaccines.

While intense efforts have been made in enigineering vaccines for HIV in the past decade, an effective vaccine has yet to be developed. The peptides of the present invention may be useful for the development of an effective vaccine for HIV. It is one object of the present invention to provide a vaccine for HIV which is effective at mucosal portals of entry and is capable of eliciting an immune response when delivered to target cells.

The existence of a "common mucosal immune compartment" distinct from systemic immunity is well documented. See Miller et al., *Lab. Invest.* 68:129–145 (1993) and James, *New Generation Vaccines*, edited by Levine M., Woodrow G C, Kaper J B and Cobon B S. Marcel Dekker, Inc., New York pages 151–171 (1995). The mucosal immune system is compartmentalized into "inductive" sites of mucosally associated lymphoid tissue (e.g. Peyer's Patches) where antigen printing occurs and "effector" sites (e.g. lamina protia and epithelium of mucosal tissue) where primed mature effector cells protect against invasion of foreign agents. See Haneberg et al., *Adv. Exp. Med. Biol.* 371A:107–109 (1995). In the intestine, antigen-stimulated induction of naive T and B lymphocytes in the Peyer's patches is followed by trafficking of these cells through adjacent draining lymph nodes (e.g. mesenteric lymph nodes). Fully mature effectors finally traffic to remote lamina propia of mucosal tissues via circulation through the thoracic duct and blood.

The present invention provides a method of eliciting an immune response and for immunogens (such as HIV vaccines). Since the primary mode of transmission of HIV is via sexual intercourse, the immunogens of the present invention can induce specific mucosal immune responses.

The immunogens of the present invention preferably comprise an internalizing peptide portion linked to cargo (e.g. antigen). The immunogens of the present invention can present antigen directly to any target cell (e.g. mucosal inductive sites).

The immunogens of the present invention can efficiently induce in immune response, e.g. T helper cell type 1 (TH1) immune responses. T-cells recognize antigens only if they are presented in the form of short, linear peptides (epitopes) in the cleft of major histocompatibility complex (MHC) molecules on the cell surface. Therefore, if antigens are to be recognized, they must first be processed into short, linear peptides. Most proteins in the cytosol are cleaved by proteases within proteosome complexes into short peptides and carried by transporter proteins into the endoplasmic reticulum (ER). In the ER, the peptides are bound to MHC molecules that are synthesized in the ER. The MHC molecules are then transported to the cell surface where the peptide bound to the MHC molecule is recognized by T-cell receptors (see FIG. 23).

Figure 23A:
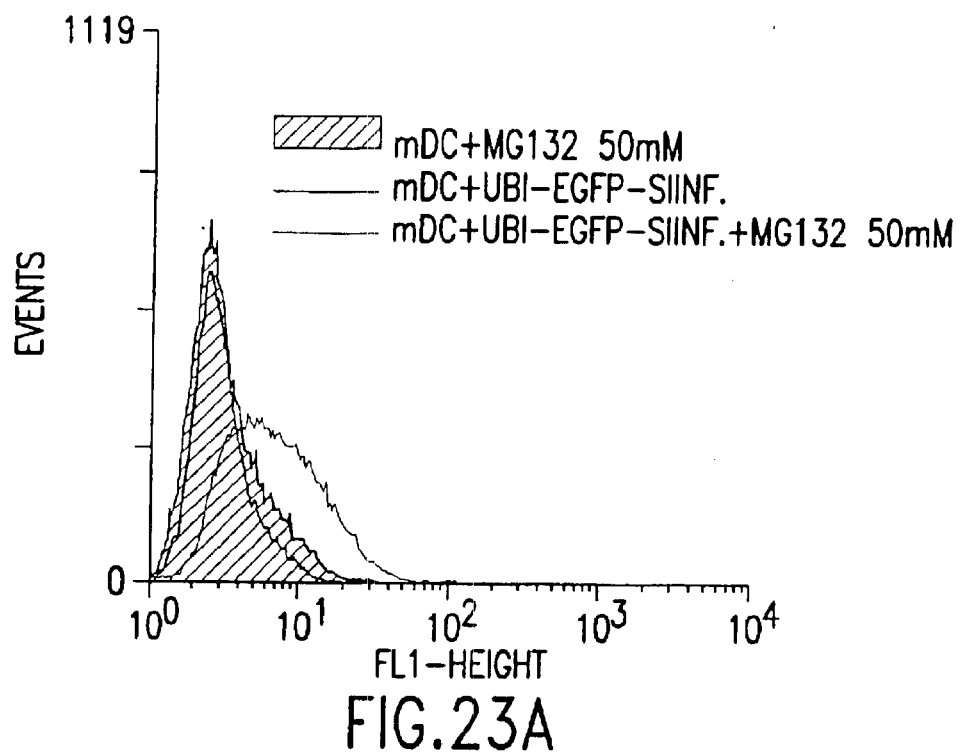
FIG. 23 is a flow cytometry analysis of GM-CSF+IL4 propagated bone marrow-derived murine dendritic cells transduced with UBI-3Epi-eGFP recombinant protein indicating that the transduction of dendritic cells with an internalizing peptide/antigen complex promotes processing and subsequent presentation of dominant epitopes. (A) represents overnight culture of transduced dendritic cells with or without the presence of the proteasome inhibitor MG132 and (B) represents overnight culture of dendritic cells transduced with UBI-3Epi-eGFP and stained with D16.25 antibody that recognizes the OVA epitope within MHC H2-Kb molecule.
Figure 23B:
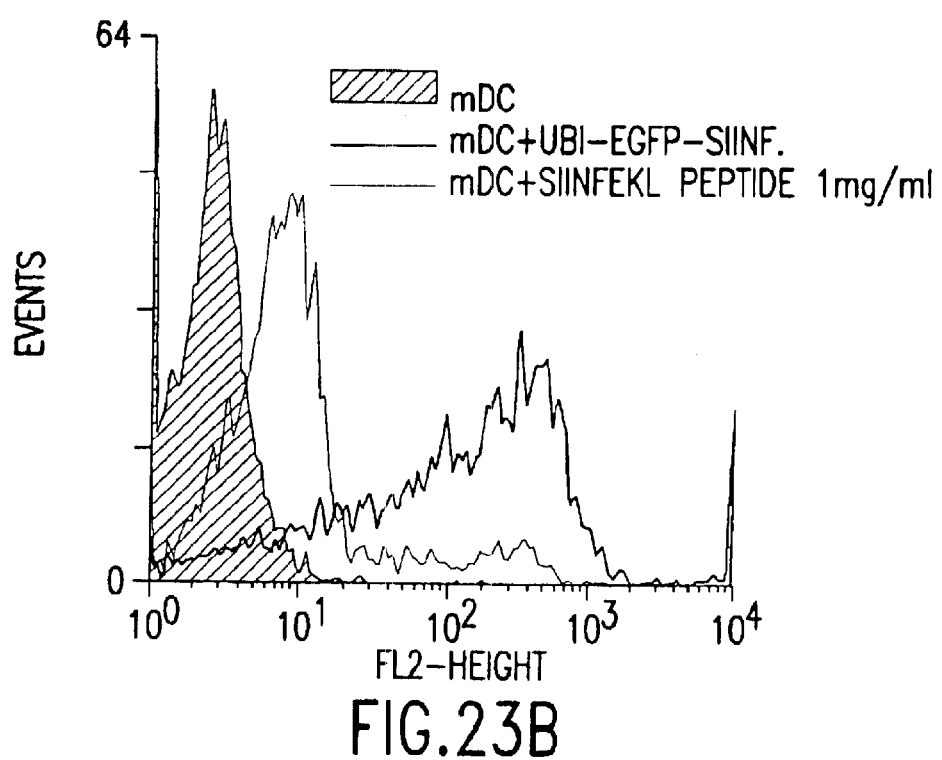
Figure 24:
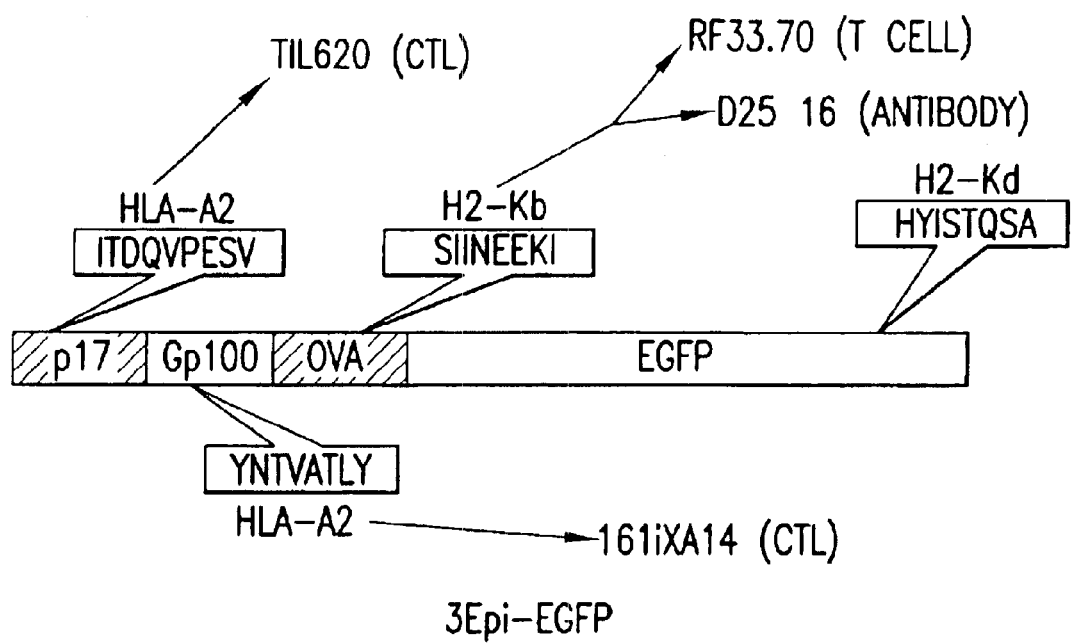
FIG. 24 is a diagram depicting a fusion protein (UBI-3Epi-eGFP) comprising the UBI peptide (SEQ ID NO:73), Gp100₂₀₉₋₂₁₇ HLA-A2-restricted epitope, HIV p17₂₃₋₂₁ HLA-A2-restricted epitope, chicken ovalbumin (OVA) epitope and green flourescent protein (eGFP).

FIG. 23 demonstrates that transduction of a target cell, e.g., dendritic cells, with the peptide/cargo complex of the present invention can promote processing and subsequent presentation of epitopes on the surface of the target cell. To demonstrate that the peptide/cargo complex of the present invention can promote processing and subsequent presentation of epitopes on the surface of a target cell, UBI (SEQ ID NO:73) was fused to a peptide comprising Gp100$_{209-217}$ HLA-A2-restricted epitope, HIV p17$_{23-21}$ HLA-A2-restricted epitope and chicken ovalbumin (OVA) epitope (termed 3-Epi) which was in turn fused to green flourescent protein (eGFP), to make UBI-3Epi-eGFP (see FIG. 24). As seen in FIG. 23, the UBI-3Epi-eGFP fusion was efficiently degraded by the proteasome complex in dendritic cells since the degradation is blocked by the proteasome inhibitor MG132 (see FIG. 23A). Furthermore, class I presentation and T cell specific recognition of epitope of the surface of mouse dendritic cells is shown in FIG. 23B using D16.25 antibody staining which recognizes the OVA epitope of UBI-3Epi-eGFP.

CD8+ cytotoxic T-lymphocytes generally recognize 8–11 mer peptides on MHC class I molecules, whereas CD4+ T-helper cells generally recognize 15–25 mer peptides on MHC class II molecules. The presentation of the short, linear peptides of the antigen on the cell surface by MHC molecules allows for the initial steps required for T-cell activation. Once T-cell activation is achieved, a potent immune response may be elicited.

The present invention provides for immunogens which may comprise an internalizing peptide of the present invention linked to cargo such as a protein representing an antigen or a DNA or RNA encoding for an antigen. The present invention also provides for a method for eliciting an immune response to a target cell, said method comprising delivering an immunogen comprising an internalizing peptide and a cargo (preferably an antigen) to a target cell. Once the immunogen is delivered to the target cell, the cargo may be processed (e.g. where the cargo is an antigen, the cargo is proteolyzed into short, linear peptides, or, where the cargo is an RNA or DNA encoding an antigen, the cargo is expressed and then proteolyzed into short, linear peptides) and presented to the cell surface thereby eliciting an immune response (see FIG. 23). The target cell may be a mucosal cell such as a cervical mucosal cell (see FIG. 22)

In a preferred embodiment of the invention, the immunogen comprises pep5 (SEQ ID NO:5) linked to cargo, such as an antigen. In another preferred embodiment of the invention, the immunogen comprises the UBI peptide (SEQ ID NO:73) linked to cargo, such as an antigen. In a further preferred embodiment of the invention, the immunogen comprises SEQ ID NO:74 linked to cargo, such as an antigen.

The cargo portion of the immunogens of the present invention may be an antigen capable of eliciting an immune response to HIV exposure, such as, inter alia, an HIV envelope protein, HIV Gag, HIV Pol, HIV Env, HIV Tat, HIV Nef, HIV Vpr, HIV Vpv and HIV Rev. Or the cargo portion of the immunogens of the present invention may be any antigen capable of eliciting a desired immune response.

The immunogens of the present invention and the methods of the present invention for eliciting an immune response in a subject can also be accomplished by ex vivo transduction of target cells followed by the presentation of the transduced cells to a subject by, for example, intramuscular or intra-dermal injection or any other technique known to the skilled artisan.

The method of the present invention for eliciting an immune response in a subject comprises administering to a target cell of said subject (whether in vitro, in vivo, or ex vivo) a peptide/cargo complex of the present invention wherein said peptide is selected from SEQ ID NOs:1–74 and the cargo is an antigen.

The peptide-cargo complexes of the present invention may be administered to a wide variety of cell types in vivo, in vitro, and ex vivo including, inter alia, epithelial cells, tumor cells, hepatocytes, endothelial cells, neurons, muscle, T-cells, dendritic cells, β cells, primary cells, differentiated cells, stem cells, antigen presenting cells, mucosa, etc by methods known to those skilled in the art.

When administered to stem cells (e.g. hematopoietic, muscle, brain, etc.), the peptide-cargo complexes of the present invention can induce differentiation of the stem cells. The peptide cargo complex comprises factors which can stimulate differentiation of stem cells, such as the transcription factor MyoD. Stem cells isolated from bone marrow have been shown to differentiate into a wide variety of tissues, including cartilage and bone, and may be useful therapeutically. See Pittenger et al., *Science* 284:143 (1999).

In addition, the peptide-cargo complex may be used to expand a stem cell population. The internalizing peptides of the present invention can deliver proteins to CD34+ hematopoietic progenitor stem cells (see FIG. 17 and Example 4). The delivery of immortalizing proteins, such as SV40 T-antigen, HPV E6, HPV E7 and telomerase, can facilitate the transient expansion of stem cell populations. Since the delivery of the immortalizing proteins using the peptides of the present invention is transient and reversible (e.g. delivery of the immortalizing protein which will be degraded subsequently in the cell), such delivery offers an advantage in that the stem cell status may be maintained (i.e. the cells may be transiently immortalized) while increasing the number of cell doublings that may be achieved. Stable delivery of immortalizing factors may also be achieved by the delivery of cargo encoding the immortalizing factor, e.g. a viral vector, plasmid, DNA. This approach can be used to expand a wide variety of stem cells in culture for transplant applications since the peptides of the present invention can facilitate the uptake and delivery of cargo linked thereto to a variety of cells (see Example 3 and FIG. 6).

Similarly, the peptides of the present invention may be used for expanding diffentiated cells (e.g. β cells in pancreatic islets, neurons, chondrocytes, etc) which also have a finite number of cell doublings in culture. The peptides of the present invention enter and facilitate the internalization of cargo in differentiated cells, such as islet β cells, (see Example 3, and FIG. 6) without affecting the ability of the islet cells to respond to signals which are indicative of differentiated function, such as glucose. The proliferation of differentiated cells may be induced by delivering immortalizing factors (e.g. SV40 T-antigen, HPV E6, HPV E7 and telomerase), and particularly SV40 T-antigen, complexed to the peptides of the present invention. The delivery may be transient (delivery of the protein) or may be stable (delivery of a DNA, viral vector, or plasmid encoding the immortalization factor).

It is also an object of the present invention to provide a construct comprising a peptide of the present invention linked to an antigen which can be taken up efficiently by a number of antigen presenting cells (e.g. dendritic cells) both in vivo and in vitro and stimulate an immune response. The peptides may be linked to, inter alia, viral antigens (e.g., HIV antigens such as Gag, Pol, Env; HPV-E6; HPV-E7; EBV-LMP1, EBV-LMP2; EBNA1; EBNA3A; EBNA3C, etc), ovalbumin, differentiation antigens (e.g., MART-1/Melan A, gp100, tyrosinase, TRP-1, TRP-2, etc.), tumor specific multilineage antigens (e.g., MAGE-1, MAGE-3, BAGE, GAGE-1, GAGE-2, p15, etc), antigens expressed uniquely by an individual's tumor (e.g., mutated gene products such as p53, CDK4, p16, p21, etc.). In one embodiment, the peptides of the present invention are linked to SIV antigens and are delivered in vivo to monkeys to determine the efficacy of said constructs in an in vivo system.

In another embodiment, the peptides of the present invention when complexed to the adeno-associated virus (AAV) Rep protein, can facilitate the integration of AAV DNA (and any DNA inserted into an AAV vector) into the genome of a target cell. The Rep protein of adeno-associated virus is able to facilitate integration of the AAV genome into a specific site on human chromosome 19. See Weitzman et al. *Proc. Natl. Acad. Sci. USA* 91:5808–5812 (1994). However the Rep protein is toxic and is difficult to deliver to cells as a DNA encoding the protein. In fact, to date it has not been feasible to generate a stable cell line constitutively expressing Rep or an adenoviral helper vector that can transiently express Rep. The present invention provides a complex comprising a peptide of the present invention (e.g. peptide 2, 3, 4 or 5) linked to the Rep protein. Such a complex facilitates the delivery of the Rep protein to a target cell. The target cell can be infected with AAV (or transfected with AAV DNA) before or after treatment with the peptide-Rep complex. The presence of the peptide-Rep complex and the AAV DNA allows for the integration of the AAV DNA into the target cell genome.

The present invention is further directed to promoting the growth of defective viruses, such as HSV, in culture. The generation of defective viruses is useful for gene therapy applications. Defective viruses do not replicate without the help of necessary replication proteins which are not encoded by such defective viruses. One approach has been to construct cell lines expressing the necessary viral replication proteins (e.g. ICP0, ICP4, ICP22 and ICP27), which have been difficult to generate. In one embodiment of the present invention, replication defective virus is grown in cells by infecting the cells with the defective virus and administering one or more complexes comprising a peptide of the present invention linked to a protein necessary for the replication of the defective virus.

GST fusion proteins are widely used in research to study various proteins due to the ease of expressing and purifying such fusion proteins. The internalizing peptides of the present invention are useful for a universal system for delivering any GST fusion protein to cells. The GST fusion protein may be made by techniques known in the art, such as the method described by Phamacia (Piscataway, N.J.). The peptides of the present invention, when linked to glutathione, can facilitate the delivery of GST fusion proteins in a target cell. The glutathione-peptide constructs of the present invention can bind to any GST fusion protein and facilitate the internalization of the GST fusion protein into a cell (see FIG. 21 and Example 8 below). The present invention is also directed to kits comprising the glutathione-peptide construct.

It is also an object of the present invention to provide an expression cassette comprising a nucleic acid encoding a fusion protein comprising a leader sequence, an internalizing peptide of the present invention, and a protein of interest, operably linked to expression control sequences. Such a fusion protein is capable of post-translational intercellular transport via the leader sequence or the internalizing peptides of the present invention. The leader sequence may be derived from secreted gene products such as interleukin-1 receptor antagonist (IL-1ra), Parathyroid hormone (PTH), or cathelin (see Huttner et al., *Ped. Res.* 45:785 (1999)). Since the leader sequence may be clipped or removed during translocation, the internalizing peptides of the present invention ensure that the fusion protein encoded by the expression cassette of the present invention may still be internalized into surrounding cells even after removal of the leader sequences, thereby improving the efficiency of intercellular transport. The protein of interest may include, inter alia, apoptotic proteins, suicide proteins, therapeutic proteins, etc. In addition, a herpes simplex virus protein, VP22, has been shown to be released from cells and taken up by neighboring cells. See Elliot & O'Hare, *Cell* 188:223–233 (1997); Elliot & O'Hare, *J. Virol.* 74:2131–2141 (2000); Derer et al., *J. Mol. Med.* 77:609–613 (1999). Another embodiment of the present invention is directed to a fusion construct comprising the leader sequence of VP22, a peptide of the present invention (preferably peptide 2, 3, 4 or 5) and a protein capable of achieving a desired effect in a cell (e.g. apoptotic protein, suicide protein, therapeutic protein, etc).

The expression cassette of the present invention may further comprise expression control sequences operably linked to the nucleic acid encoding the fusion protein and may be contained within a transfer vector which may be administered to cells either in vivo or in vitro and mediate expression therein. In addition to containing the DNA sequences encoding one or more transgenes, the chimeric adenoviral vectors of the invention may contain any expression control sequences such as a promoter or enhancer, a polyadenylation element, and any other regulatory elements that may be used to modulate or increase expression, all of which are operably linked in order to allow expression of the transgene. The use of any expression control sequences, or regulatory elements, which facilitate expression of the transgene is within the scope of the invention. Such sequences or elements may be capable of generating tissue-specific expression or be susceptible to induction by exogenous agents or stimuli. For example, suitable promoters include promoters such as from phosphoglycerate kinase (PGK) promoter or a cytomegalovirus (CMV). In one embodiment, a vector containing the expression cassette comprising DNA sequences encoding a fusion protein comprising a leader sequence, an internalizing peptide and a protein of interest is administered to a cell wherein said expression cassette is transcribed and translated and the resultant fusion protein is then secreted via the leader sequences. After secretion from the cell in which it was expressed, the fusion protein comprising an internalizing peptide, therapeutic protein or other protein of interest, and optionally the leader sequence (which may alternatively be cleaved) may be internalized into surrounding cells in vivo or in vitro via the internalizing peptides of the present invention.

Such an expression cassette is useful for sustained delivery of a peptide-cargo complex in cells. Any leader sequence capable of directing the secretion of a polypeptide linked thereto is contemplated by the present invention, including, but not limited to IL-1ra, PTH and related sequences. The expression cassette comprising DNA sequences encoding a fusion protein comprising a leader sequence, an internalizing peptide and a protein of interest is useful to direct the delivery of the protein of interest to surrounding cells. The protein of interest may be an apoptotic protein, anti-apoptotic protein, cell cycle regulatory protein, transcription factor, suicide gene product, viral or tumor antigens, or cell proliferation factors (e.g. viral oncoproteins, telomerase, etc.).

The invention is also related to methods of identifying the internalizing peptides of the present invention. Peptides having the ability to be internalized into cells can be identified by random peptide libraries coupled with an affinity enrichment process. A phage display peptide library kit, such as that supplied by New England Biolabs, Inc. (Beverly, Mass.) may be employed in the present invention for the identification of peptides which are capable of being internalized into cells and are also capable of facilitating the internalization of cargo into cells. A random peptide library may also be presented of a plasmid (as part of a fusion protein) or protein as a peptide-protein complex by techniques known in the art. Methods of identifying internalizing peptides can facilitate the isolation of peptides with superior internalizing capabilities and provide numerous peptides which can be selected for a reduced likelihood of eliciting an immune response when administered to a subject and an increased half life in vivo and/or in vitro.

The method comprises (a) incubating a target cell with a peptide display library; (b) isolating internalized peptide presented by said peptide display library from the cytoplasm and nuclei of the cells and identifying said peptides, (c) linking said peptides to cargo; (d) incubating said peptide-cargo complex with a target cell; and (e) determining ability of said peptides to facilitate the uptake and, where desired, nuclear localization of said cargo into said target cell.

In a preferred embodiment, a random peptide library is presented on the surface of bacteriophage M13 as coat protein fusions creating a physical linkage between the displayed peptide and its encoding DNA sequence. E.g., New England Biolabs, Inc. Ph.D.T.™ phage display peptide library kits (Beverly, Mass.). Such phage display peptide libraries allow for the selection of peptide ligands for a variety of targets through biopanning, including panning against intact cells. See Barry and Johnston, 1996, *Nature Medicine* 2:290–305; Szardenings et al., 1997, *J. Biol. Chem.* 272:27943–27948. Panning against intact cells may allow for the identification of peptides which facilitate the internalization of the phage on which they are displayed. See Vasily et al., 1999, *Biochimica et Biophysica Acta* 1448:450–462; and Vasily et al., 1999, *Biochimica et Biophysica Acta* 1448:463–472. Additionally, a T7 phage display library which is able to express larger peptides fused to the carboxyl terminus of the T7 phage 10B fiber protein (as compared to a 12 amino acid peptide library which is expressed on the coat of the New England Biolabs M13 library) may also be employed for biopanning.

The phage display peptide library may be incubated in a target cell line (e.g. Hig-82 cells) to isolate phage which are internalized into the cells (see Examples 2 and 3 below). The cells are then harvested and lysed to isolate the internalized phage which express peptides which are capable of facilitating their internalization. The cell lysate is collected for phage titering and amplification in bacteria. The procedure is repeated with amplified phage a total of three times to obtain phage preparations which are enriched for the peptides responsible for the internalization of the phage. After three rounds of biopanning, titering and amplification, the phage are used to infect bacterial lawns for the purpose of isolating single plaques representing a single peptide responsible for the internalization of the phage. The phage is then amplified and the phage DNA is isolated and sequenced to determine the sequence of the DNA encoding the peptide presented on the surface of the phage which was isolated by biopanning.

Where plasmid display library is used, random peptides are presented on the surface of a plasmid according to U.S. Pat. No. 5,338,665, incorporated herein by reference. The plasmid display library is then utilized in a manner similar to the method employed for the phage display library by techniques known to those skilled in the art.

After determining the sequence of the peptides isolated by the biopanning (whether by phage or plasmid display libraries or any other technique known to those skilled in the art), "free" peptides (peptides without phage) may be synthesized according to peptide synthesis methods (e.g. Merrifield solid phase synthesis). Such peptides are then conjugated to cargo. In a preferred embodiment, the peptides are synthesized such that they are biotinylated and may be conjugated to avidin labeled cargo (e.g. avidin β-gal, avidin Cy3). This allows for ease of screening of multiple peptides for their ability to internalize cargo. Additionally, the peptide may be expressed as a fusion protein with the cargo of interest (e.g. β-gal) by methods known to those skilled in the art. See e.g. Villaverde et al., 1998, *Biotechnology and Bioengineering* 59:294–301.

Other preferred cargo include, but are not limited to, proteins, such as suicide proteins (e.g. HSV TK), tumor suppressor proteins, transcription factors, kinase inhibitors, kinases, apoptotic proteins, anti-apoptotic proteins, cell cycle regulatory proteins, viral and cellular antigens, toxins, transgenes (encoding for, inter alia, protein, RNA, ribozymes, antisense RNA), RNA, plasmids, oligonucleotides (single and double stranded) and virus.

The peptide conjugates (peptide+cargo) are then incubated with a target cell to allow for delivery of the peptide-cargo complex into the cell (e.g. Hig-82 cells). The ability of the peptide to transfer the cargo into the target cell may be measured by the presence of the cargo in the target cell by techniques known in the art. Where the cargo is β-gal, the addition of Xgal to the cells will produce a blue color in the cells if the β-gal is present. Where the cargo is Cy3, confocal microscopy may be employed to determine whether the cells fluoresce. Functional assays may also determine the presence of cargo in a cell. For example, but not by way of limitation, where the cargo is CFTR (or a nucleic acid encoding CFTR), the manifestation of a functional chloride ion channel would indicate delivery of the CFTR cargo to the target cell. Where the cargo is a toxin, cell death may indicate the presence of the cargo in the target cell and, where the cargo is a virus (e.g. Human Immunodeficiency Virus, Murine Leukemia Virus, Equine Infections Anemia Virus), the virus may comprise green flourescent protein (GFP) as a marker or the virus may be labeled with Cy3, also a flourescent marker to track the internalization of the virus by the peptides of the present invention in cells which would otherwise be resistant to infection by the virus. If the virus is a viral vector comprising a transgene, the presence of the virus in the cell may be demonstrated by the presence of a transgene product. The presence of the cargo in the nuclei by the methods described above, indicates that the peptides are capable of facilitating the translocation of the cargo to the nucleus and may be demonstrated as described for internalization generally. For example, confocal microscopy may be used to demonstrate the presence of a flourescent tagged molecule in the nucleus. Alternatively, the cells may be harvested and the nuclei separated therefrom for the determination of the presence of a functional cargo therein by methods known to those skilled in the art.

In accordance with the present invention, screening for internalizing peptides by phage biopanning yielded the peptides represented by SEQ ID NO:1 through SEQ ID NO:18, further illustrated in Table 1 above. Particularly preferred peptides include KRIHPRLTRSIR (SEQ ID NO:2), PPRLRKRRQLNM (SEQ ID NO:3), PIRRKKLR-RLK (SEQ ID NO:4) and RRQRRTSKLMKR (SEQ ID NO:5) which facilitated the internalization of phage as well as the facilitation of the internalization of a cargo (e.g. β-gal and Cy3).

The peptides of the present invention may also be useful for the determination of the cell proteins which mediate internalization. For example, a cell lysate may be prepared from the cells used to isolate the internalizing peptide. The internalizing peptide may be fused to a peptide (e.g. glutathione-S-transferase or poly-histidine) which can be use for immuno-affinity purification. The peptide fusion can then be incubated with the cellular lysate and passed over a column specific for the fusion peptide (e.g. a glutathione column for the glutathione-S-transferase fusion or a nickel or cobalt column for the poly-his fusion). Proteins which bind to the internalizing peptide (e.g. cell surface receptors) may remain bound to the peptide fusion during the purification process and be purified along with the peptide fusion. The peptide-bound protein may then be isolated and its sequence may be determined by methods known in the art (e.g. N-terminal protein sequencing). Such determination may lead to the identification of other pathways which might be useful for the delivery of cargo to a target cell.

The peptides of the present invention can be prepared by classical methods known in the art, for example, by using standard solid phase techniques. The standard methods include exclusive solid phase synthesis, partial solid phase synthesis methods, fragment condensation, classical solution synthesis, and recombinant DNA technology. See, e.g., Merrifield, 1963, *J. Am. Chem Soc.* 85:2149, incorporated herein by reference.

On solid phase, the synthesis is typically commenced from the C-terminal end of the peptide using an alpha-amino protected resin. A suitable starting material can be prepared, for instance, by attaching the required alpha-amino acid to a chloroethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonsky et al., 1966, *Chem. Ind.* 38:1597. The benzhydrylamine (BHA) resin has been described by Pietta and Marshall, 1970, *Chem. Commun.* 650 and is commercially available from Beckman Instruments, Inc., Palo Alto, Calif., in the hydrochloride form.

Thus, the peptides of the invention can be prepared by coupling an alpha-amino protected amino acid to the chloromethylated resin with the aid of, for example, cesium bicarbonate catalyst, according to the method described by Gisin, 1973, *Helv. Chim. Acta.* 56:1467. After the initial coupling, the alpha-amino protecting group is removed by a choice of reagents including triflouro acetic acid (TFA) or hydrochloric acid (HCl) solutions in organic solvents at room temperature.

The alpha-amino protecting groups are those known to be useful in the art of stepwise synthesis of peptides. Included are acyl type protecting groups urethane type protecting groups, aliphatic urethane protecting groups and alkyl type protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator.

After the desired amino acid sequence has been completed, the desired peptide is decoupled from the resin support by treatment with a reagent such as TFA or hydrogen fluoride (HF), which not only cleaves the peptide from the resin, but also cleaves all remaining side chain protecting groups.

These solid phase peptide synthesis procedures are well known in the art and are further described by Stewart and Young, *Solid Phase Synthesis* ($2^{nd}$ Ed., Pierce Chemical Co., 1984), incorporated herein by reference.

The internalizing peptides of the present invention may be synthesized with additional groups, such as biotin or other markers, such that the peptide may be tracked in the cell or conjugated via the additional group to cargo. The peptides may also be later modified to incorporate any desired additional groups according to methods known in the art.

The internalizing peptides are typically synthesized as the free acid but could be readily prepared as the amide or ester where desired. Other types of modifications include, but are not limited to, methylation, acetylation and adding a benzyloxycarbonyl (t-BOC) group. Additionally the peptides may be synthesized as cyclic peptides. The C-terminal carboxyl group or a C-terminal ester can be induced to cyclize by internal displacement of the —OH or ester of the carboxyl group or ester respectively with the N-terminal amino group to form a cyclic peptide. Such methods are well known in the art.

Cyclization of the peptides or incorporation of a desamino or descarboxy residue at the termini of the peptides of the present invention, so that there is no terminal amino or carboxy group, to decrease susceptibility to proteases or to restrict the confirmation of the peptide, are also contemplated by the present invention.

The present invention also provides for compositions comprising the internalizing peptides of the present invention, complexes comprising the peptides linked to cargo, and immunogen of the present invention. Non-limiting examples include: the administration of internalizing peptides and peptide-cargo in vivo by oral, pulmonary, parental (intramuscular, intrarticular, intraperitoneal, intravenous (IV) or subcutaneous injection), inhalation (via a fine powder formulation or a fine mist), transdermal, nasal, vaginal, rectal, or sublingual routes of administration and can be formulated in dosage forms appropriate for each route of administration.

The peptide-cargo complexes of the present invention may be administered with a carrier. Such carriers include any suitable physiological solution or dispersant or the like. The physiological solutions include any acceptable solution or dispersion media, such as saline or buffered saline. The carrier may also include antibacterial and antifungal agents, isotonic and adsorption delaying agents, and the like. Except insofar as any conventional media, carrier or agent is incompatible with the active ingredient, its use in the compositions is contemplated.

The invention is further directed to methods for using the compositions of the invention for in vivo or ex vivo applications in which it is desired to deliver cargo into cells to achieve a particular phenotypic effect. In vivo applications involve, e.g., the direct administration of the peptide-cargo complex of the present invention formulated as a composition to the cells of an individual. Ex vivo applications involve, e.g., the transfer of the peptide-cargo complex of the present invention directly to autologous cells which are maintained in vitro, followed by the re-administration of the cells comprising the internalized cargo to a recipient.

Dosage of the peptide-cargo complex of the present invention to be administered in vivo in order to effect efficient delivery of cargo into a target cell and/or achieve a phenotypic effect correlated to the delivery of cargo is determined with reference to various parameters, including the species of the subject, the age, weight, and disease status and the particular physiological conditions requiring phenotypic alteration. Dosage also depends upon the location of the cells to be targeted within the subject. For example, target cells of the lung may require different dosages than administration into the blood stream of an organism. The dosage is preferably chosen so that administration causes an effective result, as measured by molecular assays or phenotypic alteration. Such assays include Western blot of a particular protein being administered or encoded by a transgene that has been administered, immunoprecipitation, immunocytochemistry, or other techniques known to those skilled in the art. Dosages may range from 0.01 nM to 1 $\mu$M. In a preferred embodiment, the dosage ranges from 1 nM to 1 $\mu$M. In a particularly preferred embodiment, the dosage is 1.5 nM for pep4 and pep5 and 15 nM for pep2 and pep3.

The practice of the present invention can be achieved by employing a number of conventional techniques of molecular biology, microbiology, recombinant DNA technology, biochemistry and immunology which are within the skill of the art. Such techniques are explained fully in the literature, see, e.g., Fritsch and Maniatis, *Molecular Cloning: A Laboratory Manual*, 2nd Edition (1989); Ausubel et al. (eds.), *Current Protocols in Molecular Biology*, (992); incorporated herein by reference.

Although only preferred embodiments of the invention are specifically described above, it will be appreciated that modifications and variations of the invention are possible without departing from the spirit and intended scope of the invention.

The following examples are provided to more clearly illustrate the aspects of the invention and are not intended to limit the scope of the invention.

EXAMPLES

Example 1

Titering M13 Phage

A phage display library (Ph.D.-12™ Catalog # 8110) was obtained from New England BioLabs (Beverly, Mass.). The Ph.D.-12™ phage display library is a library of M13 coliphage with each phage displaying a different 12 residue peptide and represents $1.9 \times 10^9$ independent clones. The randomized peptides in the library are expressed between the leader sequence and the N-terminus of the minor coat protein pIII, resulting in an average valency of 5 displayed peptides per vision. The display vector for the library is a derivative of wild-type M13 phage which is not a lytic phage. There is a physical linkage between each displayed peptide and its encoding DNA for easy determination of the selected peptide sequence.

*E. coli* ER2537 was the host strain used for the M13 phage display library. ER2537 is a robust F+ strain with a rapid growth rate and is well suited for M13 propagation.

For titering the phage, ER2537 was streaked out from a glycerol stock onto a minimal plate (500 ml 2× M9 salts (12 g $Na_2HPO_4$, 6 g $KH_2PO_4$, 1 g NaCl, 2 g $NH_4Cl$ per liter), 500 ml 3% agar, 20 ml 20% glucose, 2 ml 1 M $MgSO_4$, 0.1 ml 1 M $CaCl_2$, 1 ml thiamine (10 mg/ml)) for phage titering. After 24 hours, a single colony was picked and used to inoculate 5 ml of LB (10 g bacto tryptone, 5 g yeast extract, and 5 g NaCl per liter) which was grown for 3 hours to mid-log phase ($OD_{600}$~0.5) at 37° C. Approximately 200 $\mu$l of the stock was then spread onto a plate containing LB, IPTG and Xgal (per liter LB add 15 g agar, 0.05 g IPTG and 0.04 g Xgal). The plates were inoculated with serial dilutions of 10-fold of the phage stock and incubated overnight at 37° C. The cells infected with phage stained blue due to the presence of the phage (which contains β-gal) and the plaques were counted to determine the titer. The titer was preferably $1-2 \times 10^{11}$. Biopanning (as described below in Example 2) can be carried out with as little as $10^9$ plaque forming unites (pfu).

Example 2

Screening a Phage Display Library to Identify Internalizing Peptides

Hig-82 biopanning: Hig-82 cells (rabbit synovial cell line supplied by Christopher Evans, University of Pittsburgh, ATFCC Deposit No. CRL-1832) were employed for screening the New England Biolabs Ph.D-12™ phage-display library. The Hig-82 cells were cultured in 10 cm plates and grown to 100% confluency. The cells were then incubated with approximately $4\times10^{10}$ phage in a volume of 10 µl overnight at 4° C. The Hig-82 cells were then harvested and washed twenty times with wash buffer (25 mM Tris-HCL pH 7.4, 150 mM NaCl, 1 mM CaCl$_2$, 10 mM MgCl$_2$, 1% bovine serum albumin (BSA)). The last washing solution was collected and titered to determine if any phage were present. This wash had no phage indicating that the washing was sufficient. Phage which were bound to the cells were eluted with 50 mM glycine, pH 2.2 for 30 minutes at room temperature and the eluate was immediately thereafter neutralized for two minutes with 0.2M NaPO$_4$ buffer, pH 8.0. The eluate was collected for phage titering and amplifying.

The cells were then trypsinized from the plate with 0.05% trypsin, 0.53 mM EDTA and lysed by three consecutive rounds of freeze/thaw in dry ice/EtOH. The lysed cells were then centrifuged and the supernatant was collected for phage titering and amplification. The cell pellets containing the cell debris were washed with wash buffer (see above) five times and the last wash was collected for phage titering. The cell pellet containing the cell debris was then eluted with 50 mM glycine, pH 2.2 for 30 minutes at room temperature and the eluate was immediately thereafter neutralized for two minutes with 0.2 M NaPO$_4$ buffer, pH 8.0. The eluate was collected and saved for phage titering and amplification.

Phage titering as accomplished as described above in Example 1 and the phage were amplified by adding the eluates to a 20 ml ER2537 culture grown to early-log phase in LB medium as described above in Example 1 and incubating for 4.5 hours at 37° C. with vigorous shaking. The culture was then centrifuged for 10 minutes at 10,000 rpm in a Sorvall model SS-34 centrifuge at 4° C. The supernatant was transferred to a new tube and spun a second time. The upper 80% of the supernatant was then transferred to a new tube and 1/6 volume of PEG/NaCl (20% w/v polyethylene glycol-8000, 2.5 M NaCl) was added and incubated overnight at 4° C. to precipitate the amplified phage. The PEG precipitate was then centrifuged for 15 minutes at 10,000 rpm at 4° C. (supernatant was decanted and pellet was respun briefly) and residual supernatant was removed with a pipette. The pellet was resuspended in 1 ml TBS (50 mM Tris-HCL (pH 7.5), 150 mM NaCl) and spun in a microcentrifuge tube to remove any remaining debris. The supernatant was transferred to a fresh microcentrifuge tube and re-precipitated with 1/6 volume PEG/NaCl, incubated for 60 minutes on ice and microcentrifuged for 10 minutes at 4° C. The pellet was resuspended in 200 µl TBS, 0.02% NaN$_3$ and recentrifuged to remove any remaining debris. The supernatant represented the amplified phage.

The procedure (referred to hereafter as biopanning) was repeated a total of three times to achieve phage stocks enriched for phage which were internalized into the Hig-82 cells.

Human Primary T-cell biopanning: Human primary CD4 and CD8 T-cells (purified from peripheral blood mononuclear cells (PBMC) of normal donors using immunomagnetics beads (Miltenyi Biotech., Bergish Gladbach, Germany)) were employed for screening the New England Biolabs Ph.D-12™ phage-display library. The T-cells were incubated at 37° C. overnight in the presence of 25 IU/ml interleukin2 (IL2). The cells were then incubated with approximately $4\times10^{10}$ phage in a volume of 10 µl for 4 hours it 4° C. with gentle shaking. The T-cells were then harvested and washed extensively with Tris-buffered saline (TBS).

Phage which were bound to the cells were eluted with 50 mM glycine, pH 2.2 for 10 minutes at room temperature and the eluate was immediately thereafter neutralized for two minutes with 0.2M NaPO$_4$ buffer, pH 8.0. The eluate was collected for phage titering and amplifying.

The cells were then trypsinized from the plate with 0.5% trypsin, 0.53 mM EDTA, washed 2× with TBS at room temperature, centrifuged to remove wash and resuspended in 0.2 ml TBS. The T-cells were then lysed by three consecutive rounds of freeze/thaw in dry ice/EtOH. The lysed cells were then centrifuged and the supernatant was collected for phage titering and amplification.

Phage titering was accomplished as described above in Example 1 and the phage were amplified as described for Hig-82 cells.

The procedure (referred to hereafter as biopanning) was repeated a total of three times to achieve phage stocks enriched for phage which were internalized into the T-cells.

Calu 3 cell biopanning: The human lung adenocarcinoma cell line Calu 3 (ATCC, Rockville, Md.) was cultured in a flask with a 1:1 ratio of DMEM media and F12 media to 70% confluency, then trypsinized from the flask, washed 1× with TBS and transferred into a cell culture filter and grown to 100% confluency in a 1:1 ratio of DMEM media and F12 media. Phage biopanning was performed as above for human primary T-cells.

Cervical Tissue biopanning: Surgically resected cervical mucosa cells from human patients were grown in a 60 mm tissue culture dish in the presence of 5 ml of complete DMEM media. The cervical mucosa cells were then incubated with approximately $4\times10^{10}$ phage in a tissue culture dish for 18 hours. The mucosa tissue was then trypsinized and class II positive cells were selected from a single cell suspension using immunomagnetics beads (Miltenyi Biotech, Bergish Gladbach, Germany) following the manufacturer's protocol. The purified mucosal cells were then lysed by three consecutive rounds of freeze/thaw in a −70° C. freezer. The lysed cells were then centrifuged and the supernatant was collected for phage titering and amplification.

Phage titering was accomplished as described above in Example 1 and the phage were amplified as described for Hig-82 cells.

Example 3

Figure 7:
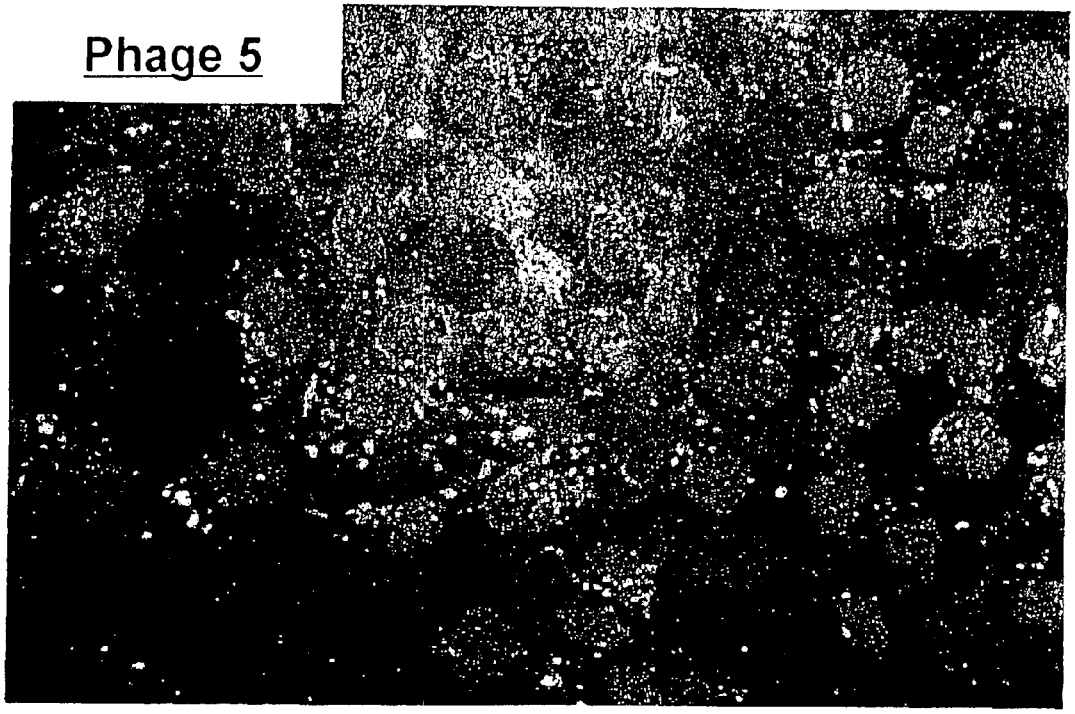
FIG. 7 shows the ability of peptide 3 (SEQ ID NO:3) and peptide 5 (SEQ ID NO:5) to internalize Cy3 labeled-M13 phage when said peptides are expressed on the surface of the phage.
Figure 7:
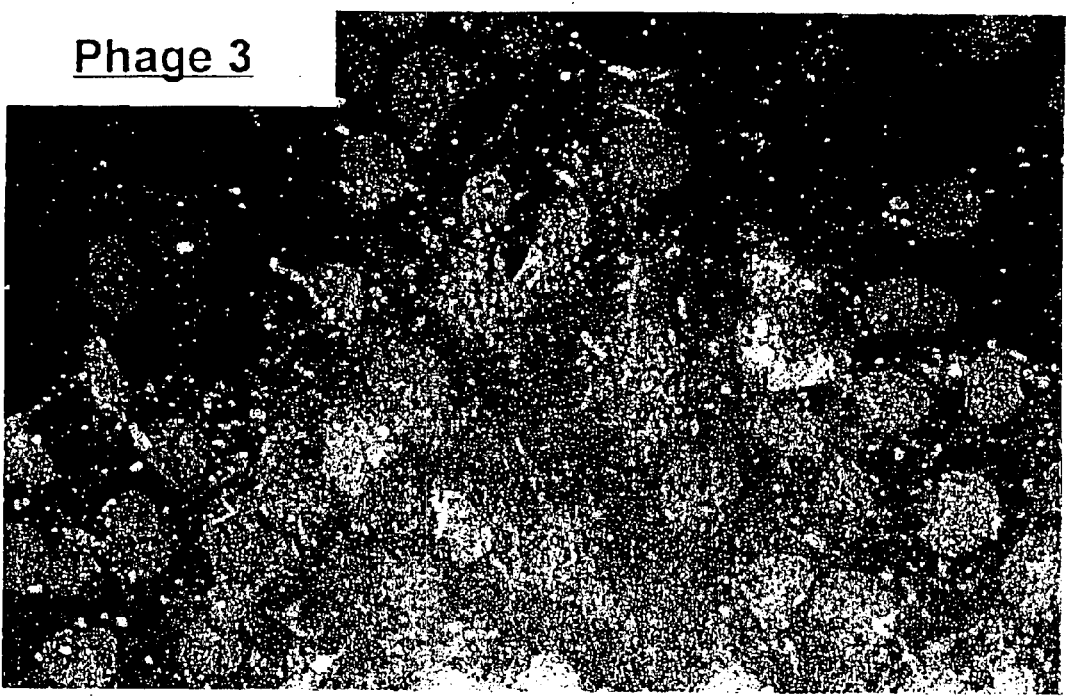

Identification of Phage Displayed Peptides which were Internalized into Hig-82 Cells, T-cells, Calu3 Cells, and Cervical Tissue After three rounds of biopanning, the enriched phage preparations were plaqued as described above in Example 1 for phage titering. A single plaque was then picked (from plated containing approximately 100 plaques) with a sterile wooden stick and transferred to a tube containing 1 ml of ER2537 culture in LB and incubated for 4.5 hours with shaking. The phage were amplified as described above in Example 2. Phage DNA was prepared from the amplified stock by centrifuging the 1 ml cultures in a microcentrifuge for 30 seconds, removing the supernatant, adding 200 µl PEG/NaCl and precipitating the phage for 10 minutes at room temperature. The precipitated phage were then centrifuged for 10 minutes in a microcentrifuge and the supernatant was discarded (a subsequent spin was performed to remove any remaining supernatant). The pellet was resuspended in 100 µl iodide buffer (10 mM Tris-HCl (pH 8.0), 1 mM EDTA, 4 M NaCl), 250 µl EtOH was added and the mixture was incubated for 10 minutes at room temperature to preferentially precipitate single-stranded phage DNA and leave most of the phage protein in solution. The precipitated phage DNA was then centrifuged for 10 minutes in a microcentrifuge and the pellet was washed with 70% EtOH and dried briefly under vacuum. The dried phage DNA pellet was then resuspended in 30 µl TE buffer (10 mM Tris-HCl (pH 8.0, 1 mM EDTA). The phage DNA (approximately 5 µl of the 30 µl preparation) was then sequenced (automated DNA sequencing at the University of Pittsburgh) to determine the sequence of the peptides which were internalized. FIG. 7 shows the uptake of M13 phage labeled with Cy3 by peptide 3 (SEQ ID NO:3) and peptide 5 (SEQ ID NO:5). The peptides identified are pep 1 through pep 66 (SEQ ID Nos:1–18 and 25–72 respectively) as represented in Table 1–4 above.

Figure 13B:
FIGS. 13A-D: (A) fluorescence microscopy showing the ability of peptide 5 (SEQ ID NO:5) to internalize a streptavidin-488 flourescent marker and a Cy3 flourescent marker into HIG-82 cells; (B) confocal microscopy showing the ability of peptide 5 to internalize a streptavidin-488 flourescent marker and a Cy3 flourescent marker into HIG-82 cells; (C) shows the ability of peptide 5 linked to Cy3 to be internalized into HIG-82 cells; and (D) shows the ability of peptide 5 linked to M13 phase labeled with Cy3 to be internalized into HIG-82 cells.
Figure 13D:
Figure 13A:

To show that the peptides of the present invention are able to facilitate internalization and transport of protein complexes and phage (virus) to the nucleus of a cell, biotinylated peptides were coupled to streptavidin-488. See Bayer et al., *Histochem. Cytochem.* 24:933–939 (1976); Ivanenkov & Menon, *Biochim. Biophys. Acta.* 1448:463–472 (1999). The use of the 488 flourescent marker allows for analysis of the treated cells by confocal microscopy to determine the exact location of the complexes in the cells. Peptide 5 (SEQ ID NO:5) was able to facilitate the efficient internalization of the streptavidin-488 complex (FIG. 13A) with a significant percentage of the peptide-streptavidin-488 complex being found in the nucleus by confocal microscopy of treated cells (FIG. 13B).

Figure 13C:
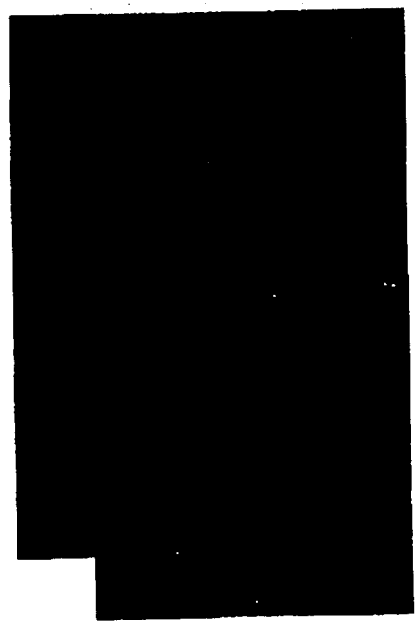

To determine if the peptides of the present invention are able to facilitate internalization of intact M13 phage (a virus), as suggested by the screening and isolation procedure, a peptide 5/M13 phage complex was labeled with Cy3 (as for FIG. 5) and added to rabbit synovial fibroblasts. Labeled peptide 5/M13 phage complex was detected in the treated cells (FIG. 13D) compared to the control phage (FIG. 13C). Thus peptide 5, as well as peptides 2, 3, and 4 (SEQ ID NOs:2–4 respectively) were able to facilitate internalization and nuclear localization of protein complexes as well as intact M13 phage. Therefore, the peptides of the present invention are useful for facilitating the internalization of virus and viral vectors.

Example 4

Identifying Peptides which Facilitate Internalization of Conjugated Cargo (β-Galactosidase and CY3)

Internalizing peptides 1–6 (SEQ ID Nos:1–6 respectively), which were identified as described above in Example 3, were synthesized, and biotinylated (synthesis and biotinylation performed by the Biotech Center of the University of Pittsburgh). The biotinylated peptides were then conjugated to avidin β-gal or avidin Cy3 at room temperature for 2 hours.

The peptide conjugates were then added to cells (Hig-82 cells, rabbit synovial cells, human synovial cells, rabbit synovial lining, human primary airway cells HBE 144, human primary islet cells, murine myoblast cells C2C12, dog kidney epithelial cells MDCK, murine fibroblast cells NIH3T3 and murine tumor cells MCA 205 (human synovial cells and human primary airway cells (HBE144) were isolated from patients from the Presbyterian Hospital, University of Pittsburgh by standard techniques for establishing a primary cell culture; human islet cells were provided by the University of Miami and were isolated by standard techniques for establishing a primary cell culture; C2C12, MDCK, 3T3 and MCA205 cells were purchased from ATTC, Bethesda, Md.; all cells were cultured in DMEM and grown to 100% confluency) and incubated while gently rotating at 37° C. for 3 hours with TBS buffer. The cells were then washed 10 times with TBS buffer and fixed with 4% paraformaldehyde at room temperature for 30 minutes. Cells were then washed 3 times with TBS buffer and stained with 1 mg/ml X-gal (Bochringer Mannheim, Indianapolis) at 37° C. overnight for β-gal-conjugated peptides. Cells which were blue indicated the presence of β-gal in the cells. For Cy3-conjugated peptides, fluorescence of the cells as measured by confocal microscopy indicated the ability of the peptide to internalize the Cy3 (a small molecule cargo).

Figure 1B:
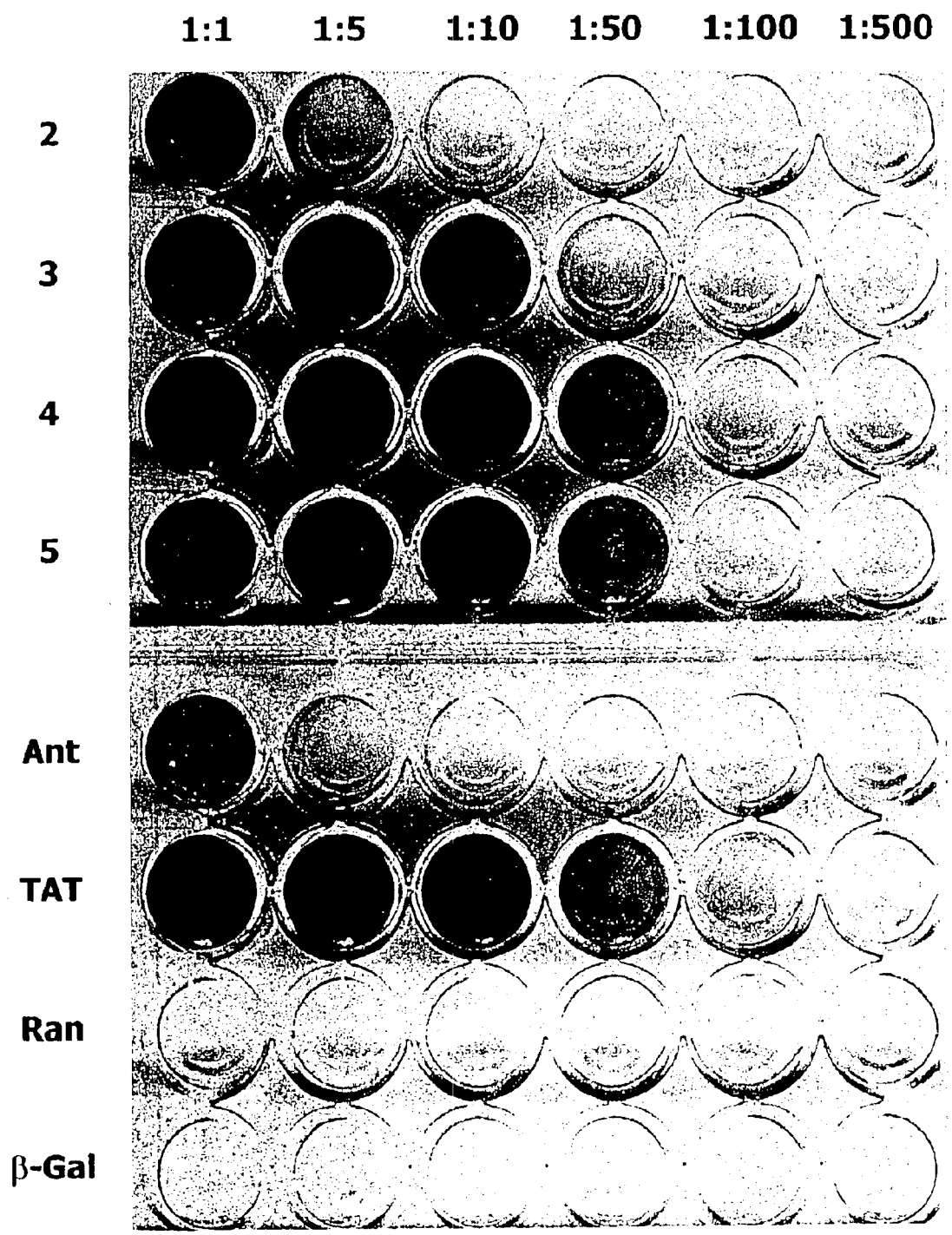
Figure 2B:
FIGS. 2A-D.
Figure 2A:
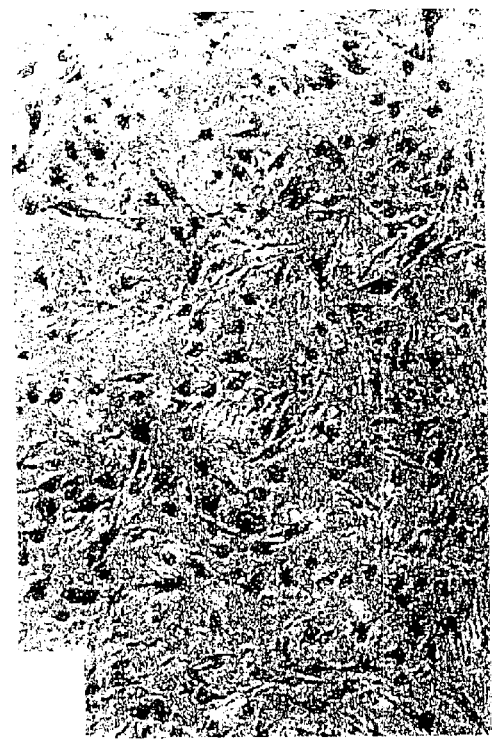
Figure 2C:
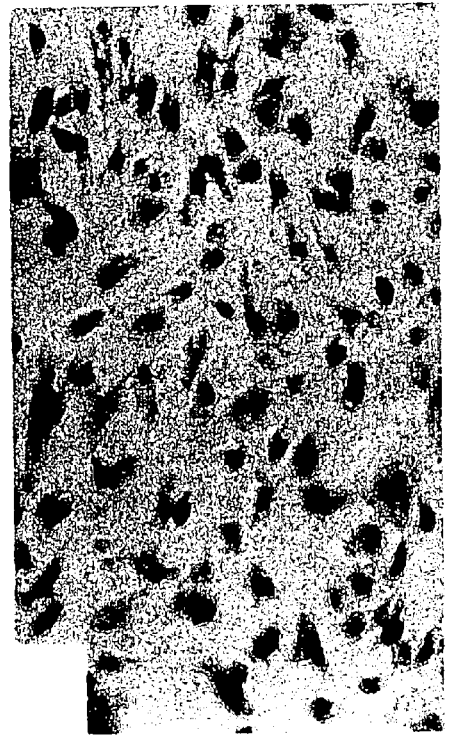
Figure 2D:
Figure 3B:
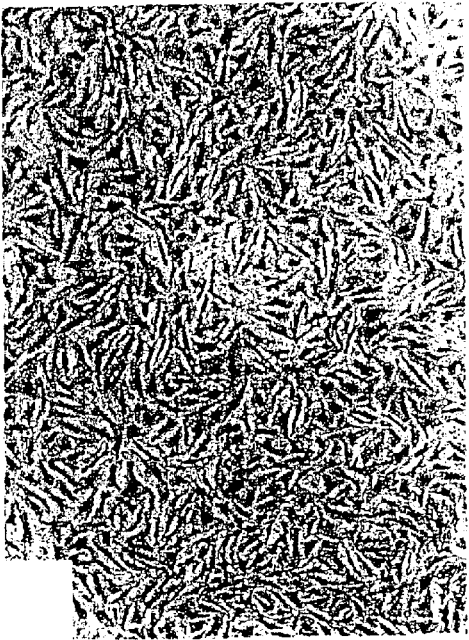
FIGS. 3A-D.
Figure 3D:
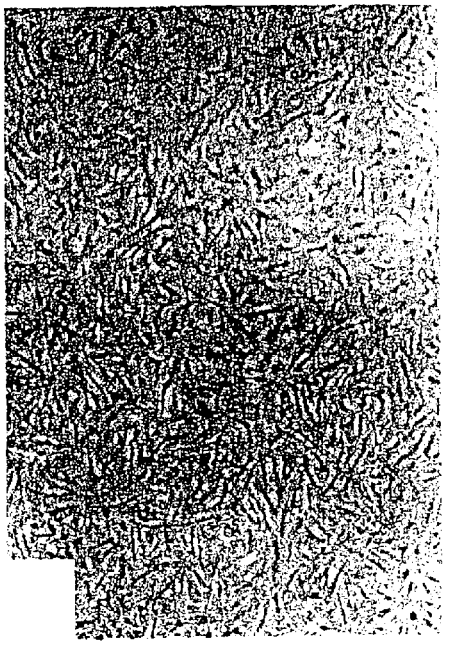
Figure 3A:
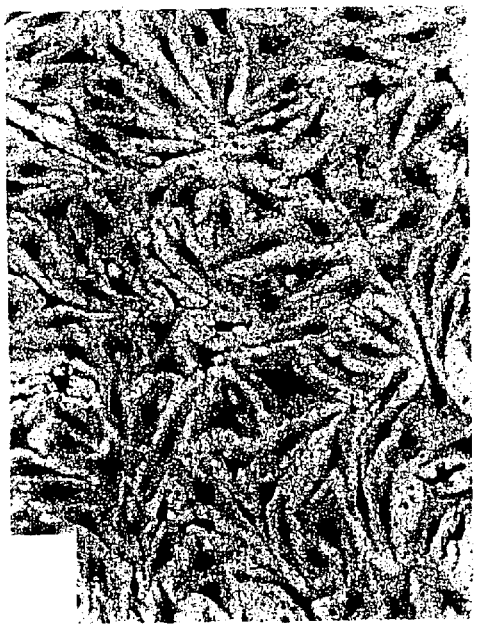
Figure 3C:
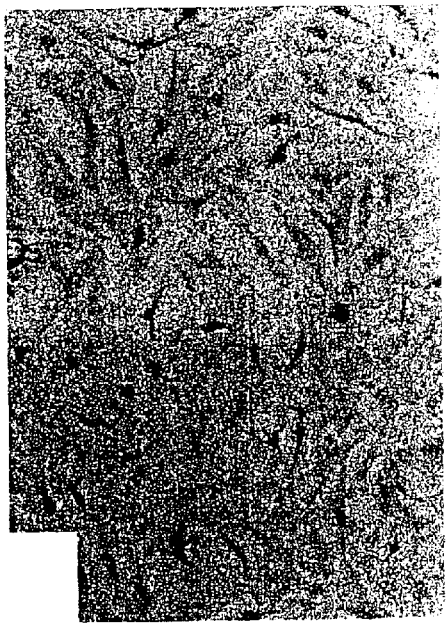

FIG. 1A shows the results of peptide-β-gal complex internalization into Hig-82 cells using peptide 1, 2, 3, 4, 5 and 6 (SEQ ID Nos:1–6 respectively) as compared to antennapedia peptide (RQIKIWFQNRRRMKWKK; SEQ ID NO:19). TAT-PTD (YGRKKRRQRRR; SEQ ID NO:21), and a random control peptide (ARPILEHGSDKAT; SEQ ID NO:20). FIG. 1B shows the relative strength of internalization mediated by peptides 2, 3, 4 and 5 (SEQ ID NOs:2–5 respectively) as compared to antennapedia peptide (SEQ ID NO:19), TAT-PTD (SEQ ID NO:21), and a random control peptide (SEQ ID NO:20). In FIG. 1B, various concentrations of peptides linked to β-gal were tested (1:1=150 nM of β-gal). The results show that peptides 4 and 5 (SEQ ID NOs:4 and 5 respectively) effect internalization of β-gal linked thereto at a concentration equal to or less than TAT-PTD, suggesting that internalization mediated by peptides 4 and 5 is equal or superior to internalization mediated by TAT-PTD. Peptides 3 and 4 achieved internalization of β-gal at a slightly higher concentration. Strikingly, peptides 2–5 were more effective than the commercially available antennapedia peptide.

FIG. 2A-D shows the ability of peptide 1 (SEQ ID NO:1) (FIGS. 2A and 2C, low and high magnification respectively) and peptide 3 (SEQ ID NO:3) (FIGS. 2B and 2D, low and high magnification respectively) to facilitate the internalization of β-gal into rabbit synovial cells. FIG. 3A-D shows the ability of peptide 5 (SEQ ID NO:5) (FIGS. 3A and 3B, high and low magnification respectively) and peptide 1 (SEQ ID NO:1) (FIGS. 3C and 3D, high and low magnification respectively) to facilitate the internalization of β-gal into human synovial cells.

Figure 4A:
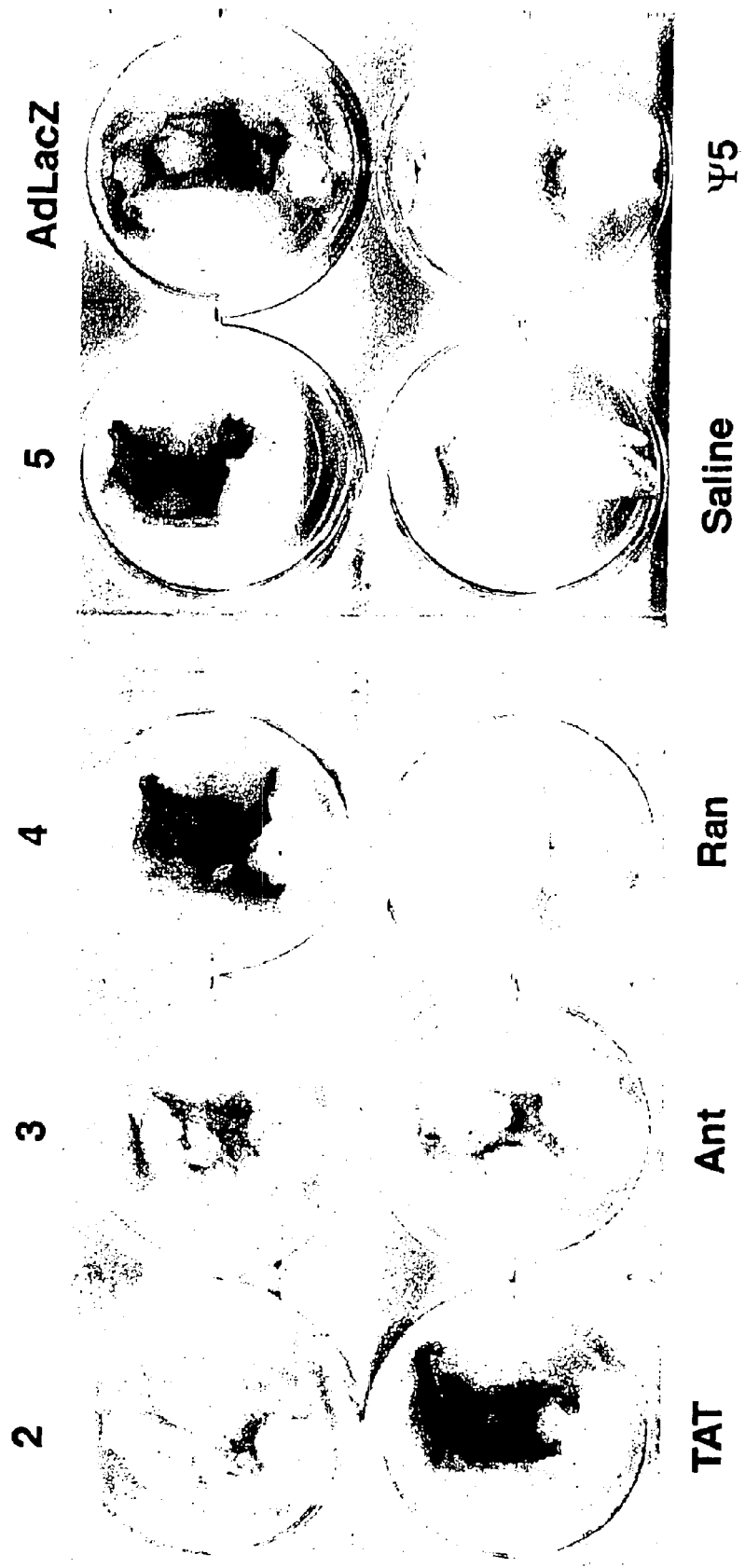
FIGS. 4A & B: (A) shows the ability of peptides 2, 3, 4, 5, TAT-PTD, antennapedia peptide and a random peptide (SEQ ID Nos:2, 3, 4, 5, 21, 19 and 20 respectively), to facilitate the uptake of β-gal in rabbit synovial lining; (B) histology of rabbit synovial lining using eosin counter-stain.

FIG. 4 shows the ability of peptides 2–5 (SEQ ID NOs:2–5, respectively), TAT-PTD (SEQ ID NO:21), antennapedia peptide (SEQ ID NO:19), a random control peptide (SEQ ID NO:20) and an adenoviral vector encoding β-gal (ψ5) to facilitate in vivo transfer of peptide-conjugated β-gal into rabbit synovial lining. Peptide-β-gal complexes (fusions) were injected into rabbit knee synovial lining, the lining as then removed, washed with wash buffer, fixed with 4% paraformaldehyde, and stained with β-gal. Peptides 4, 5 and TAT-PTD showed the highest level of uptake into the rabbit synovial lining (FIG. 4A). The control peptide and saline alone showed no uptake. The level of uptake was significantly higher for all the internalizing peptides as compared to the adenoviral vector encoding β-gal, which was injected 3 days prior to injection of the peptide-β-gal constructs (FIG. 4A).

Figure 4B:
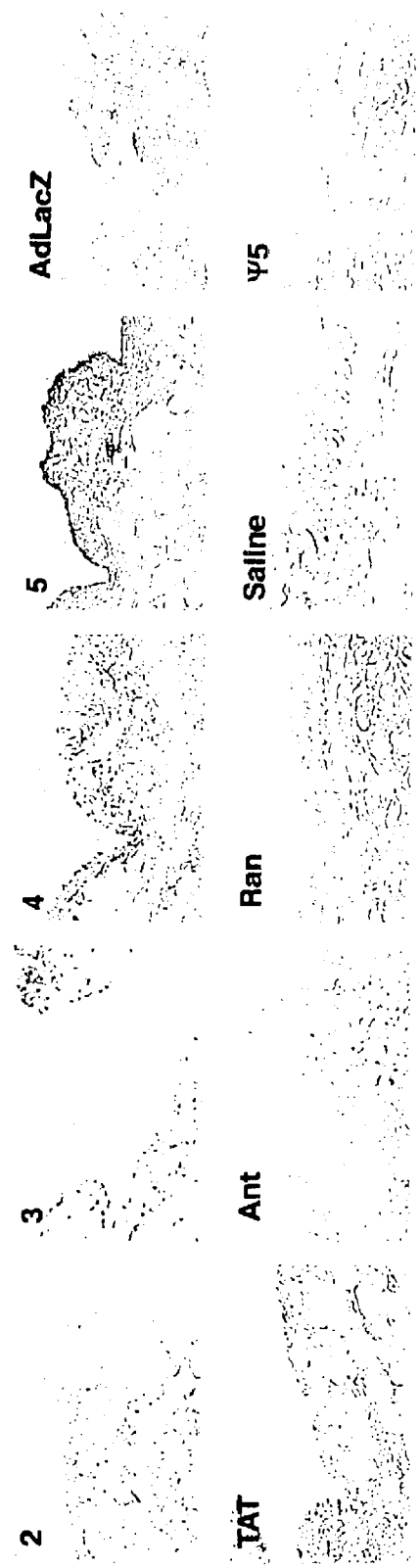

FIG. 4B shows the histological analysis of the rabbit synovial lining using an eosin counter-stain. The histological analysis showed that β-gal staining was intracellular and limited to the synovial lining. Peptide 5 (SEQ ID NO:5) was able to facilitate uptake of β-gal in nearly 100% of the synovial cells in vivo (FIG. 4B). Injection of peptide 5 (SEQ ID NO:5) into day 14 murine tumors which were prepared by subcutaneously injecting MCA-205 cells (fibrosarcoma cell line) resulted in significant β-gal staining that was also significantly higher than that observed for an adenoviral vector encoding β-gal. These in vivo results show that the peptides of the present invention can facilitate efficient internalization of protein complexes into joints and tumors and thus are useful for delivery of proteins of interest (such as apoptotic proteins, suicide proteins, tumor suppressor proteins, chemotherapeutic agents, etc) to joints (e.g. arthritic joints) and tumor cells.

Figure 9A:
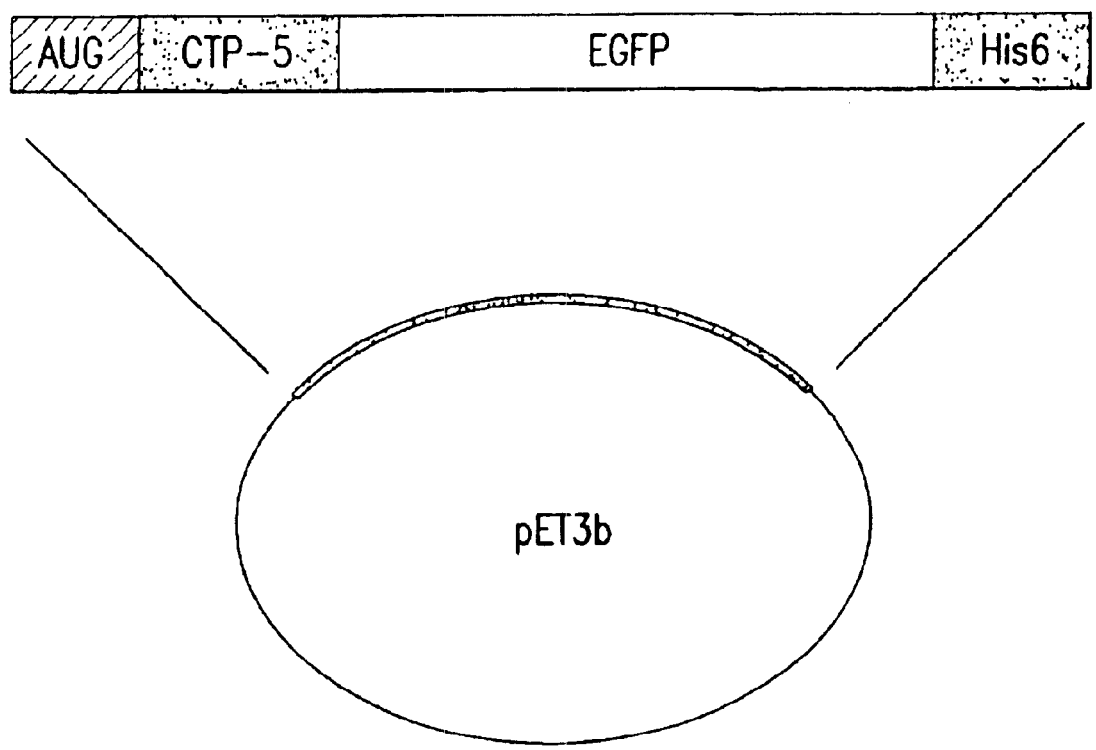
FIGS. 9A-G: (A) schematic drawing of the vector construct for eGFP fusion protein; (B & C) shows the ability of peptide 5 to internalize eGFP in human islets at low magnification (B is a photomicrograph of the histologically stained cells and C shows the fluorescent detection of eGFP); (D & E) shows the ability of peptide 5 to internalize eGFP in human islets at high magnification (D is a photomicrograph of the histologically stained cells and E shows the fluorescent detection of eGFP); and (F & G) shows the ability of peptide 5 to internalize eGFP in human dendritic cells (F is a photomicrograph of the histologically stained cells and G shows the fluorescent detection of eGFP).
Figure 9F:
Figure 9G:
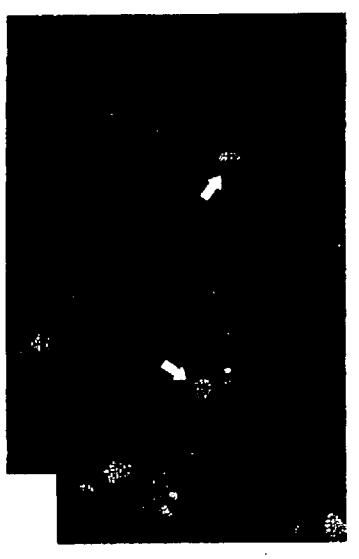
Figure 9D:
Figure 9E:
Figure 9B:
Figure 9C:
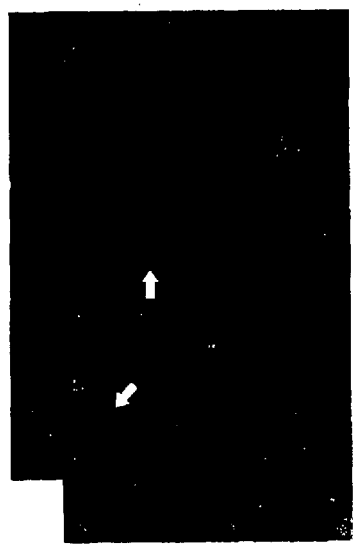

FIG. 6A-I shows the ability of peptide 5 (SEQ ID NO:5) to facilitate the uptake of β-gal in (6A) HIG-82 cells; (6B) rabbit primary synovial cells; (6C) human primary synovial cells; (6D) HBE 144 primary human airway epithelial cells; (6E) MDCK polarized canine kidney cells; (6F) human β islet primary cells; (6G) C2C12 murine myoblast cells; (6H) MCA205 murine fibrosarcoma cells; and (6I) NIH3T3 cells. Additionally, FIG. 9B-C shows the ability of peptide 5 to facilitate internalization of eGFP in human islets at low magnification (9B is a photomicrograph of the histologically stained cells and 9C shows the fluorescent detection of eGFP). FIG. 9D-E show the ability of peptide 5 to facilitate internalization EGFP in human islets at high magnification (9D is a photomicrograph of the histologically stained cells and 9E shows the fluorescent detection of eGFP). FIG. 9F-G shows the ability of peptide 5 to facilitate the internalization of EGFP in human dendritic cells (9F is a photomicrograph of the histologically stained cells and 9G shows the fluorescent detection of eGFP). FIG. 9A is a schematic representation of the expression construct encoding the peptide5-eGFP fusion protein.

Figure 17:
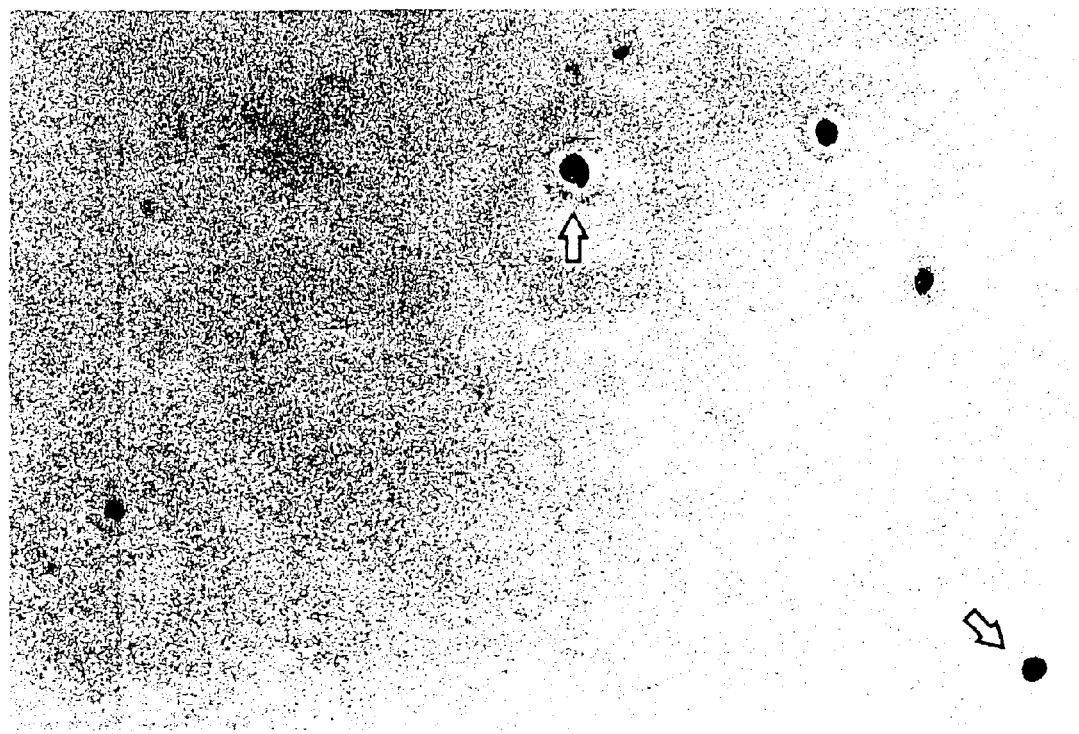
FIG. 17 shows the ability of peptide 5 to facilitate the uptake of β-gal into CD34+/LIN− stem cells.

FIG. 17 shows the ability of peptide-5 linked to β-gal to transduce CD34+/LIN- stem cells. Peptide 5 is biotin labeled and the β-gal is avidin labeled so that they may be linked together by an avidin/biotin interaction. The cells which stained dark were transduced with the peptide/β-gal complex as indicated by an arrow.

Figure 8:
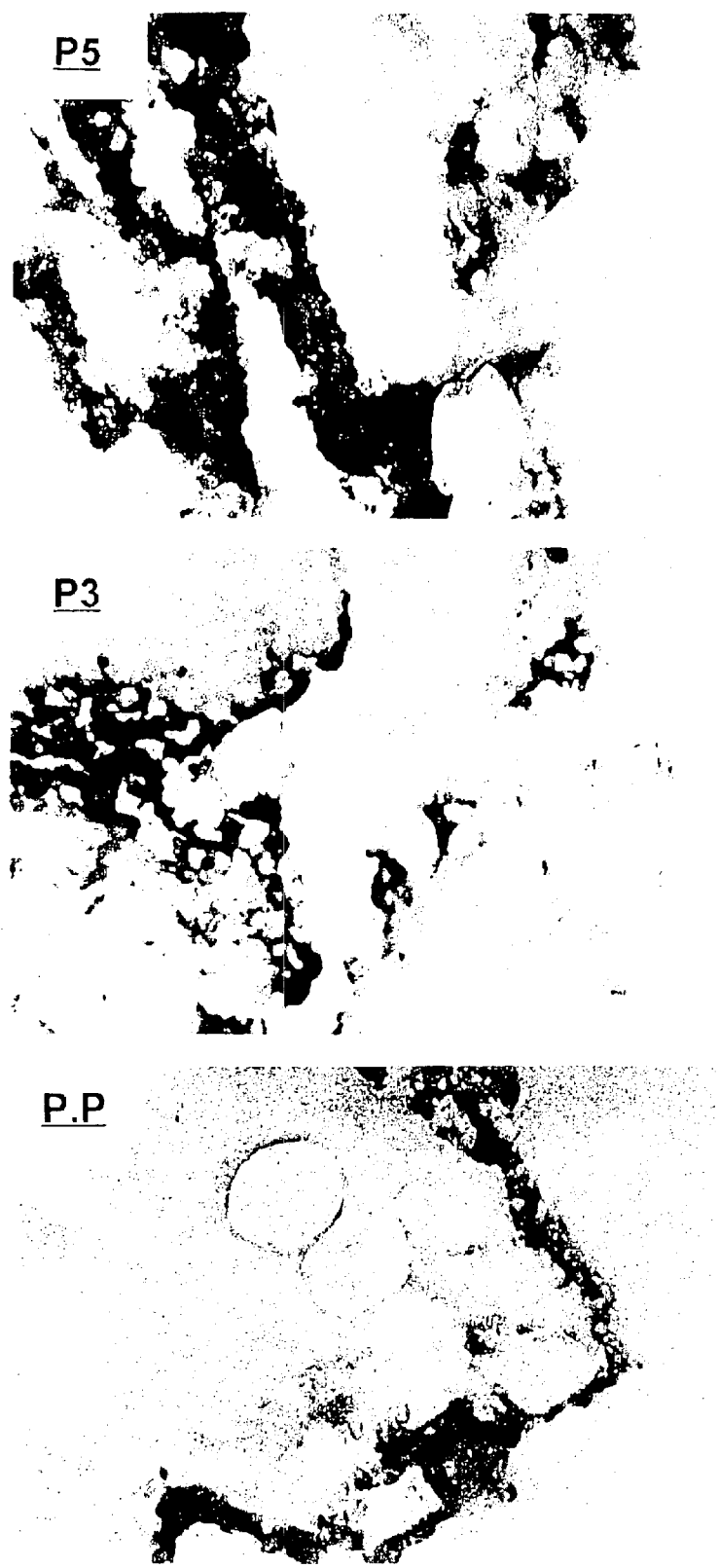
FIG. 8 shows the ability of peptide 3 (SEQ ID NO:3), peptide 5 (SEQ ID NO:5) and the antennapedia peptide (P.P) (SEQ ID NO:19) to facilitate the uptake of β-gal when linked thereto into tumor cells in vivo following intra-tumoral injection.

To make the nucleic acid encoding the peptide-eGFP fusion depicted in FIG. 9A, PCR was employed using 5' and 3' primers that encoded the peptide and a his tag, respectively, and had complimentary sequences to eGFP DNA coding sequences. The resultant PCR product was subcloned into the bacterial expression vector pET ((Novagen, Madison, Wis.). For protein expression, the expression vector comprising the DNA encoding a peptide eGFP fusion with a his tag was transfected into bacterial cells which were grown by standard techniques. The cells were induced to express the fusion product with 1 mM IPTG and were harvested and lysed. The fusion protein was purified over a Nickel column. The purified protein was then added to the media of Hig-82 cells in culture. The eGFP positive cells were visualized under a fluorescence microscope. FIG. 8 shows the ability of peptide 3 (SEQ ID NO:3) and peptide 5 (SEQ ID NO:5), as well as the antennapedia peptide (SEQ ID NO:19) to facilitate the internalization of β-gal into murine tumor cells in vivo. MCA 205 tumor cells (5×10⁵ cells) were injected subcutaneously into the flank of a C57/BL6 mouse. At day 14, a single intra-tumoral injection of the peptide β-gal complex was performed. The mice were sacrificed 3 hours post-injection and the tumor tissue was isolated, sectioned and stained with X-gal.

These data indicate that the internalizing peptides of the present invention can facilitate the uptake of cargo (β-gal or Cy3) into cells both in vitro and in vivo. Additionally, since the cargo was transported to the nucleus of the cells, the data also indicate that the peptides facilitated nuclear translocation of the cargo as well (see FIGS. 1, 2, 3, and 6).

Example 5

Peptide Competition Assay

A peptide competition assay was carried out to determine the relative efficiency and specificity of the various peptides. The peptides were conjugated to β-gal as described above in Example 4 and incubated with Hig-82 cells grown to 85% confluency in 24 well plates in the presence of non biotinylated peptides for 3 hours at 37° C. in TBS buffer while being gently rotated. The cells were then washed 10 times with TBS buffer, fixed with 4% paraformaldehyde at room temperature for 30 minutes, washed 3 times with TBS buffer, and stained with Xgal, as described above in Example 4, overnight. Cells which stained blue had internalized peptide-conjugated β-gal.

Figure 5:
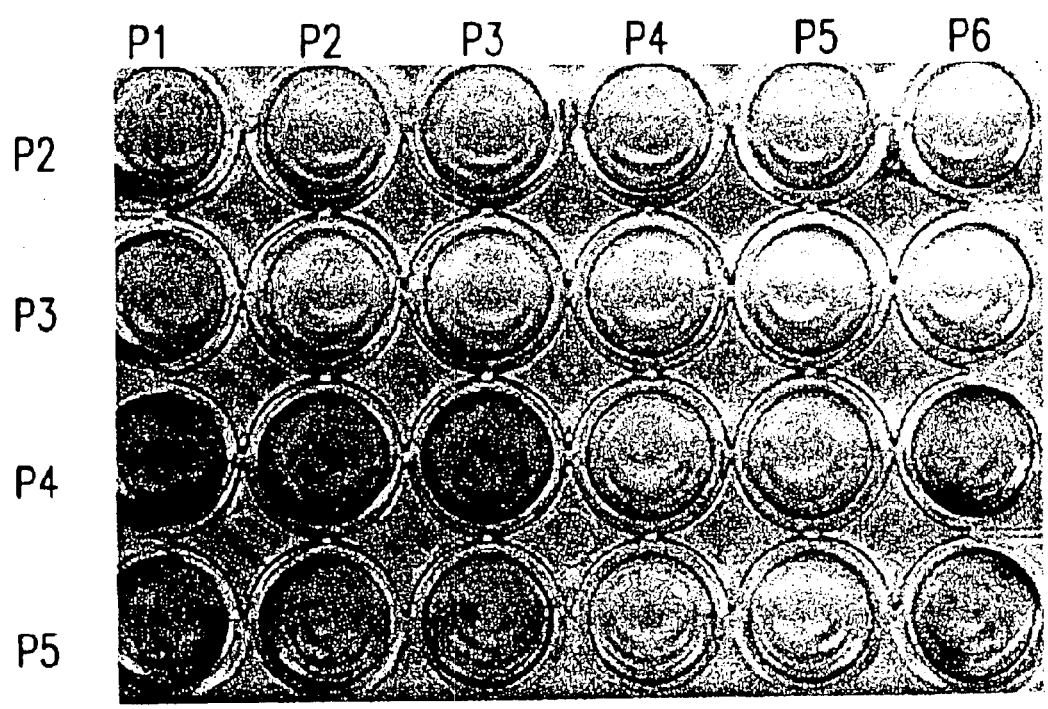
FIG. 5 shows the ability of various peptides (peptides 1–6; SEQ ID Nos:1–6 respectively) to compete for binding in Hig-82 cells.
Figure 6C:
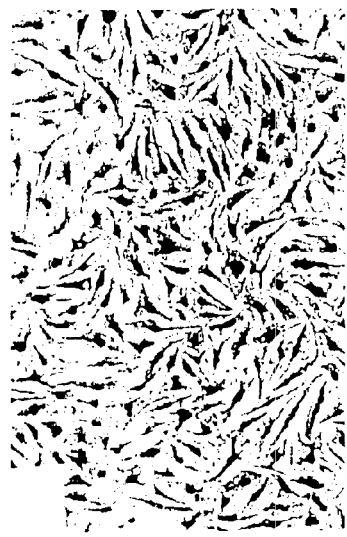
Figure 6B:
Figure 6A:
Figure 6F:
Figure 6E:
Figure 6D:

FIG. 5 shows the ability of the various non-biotinylated peptides to compete for internalization of the peptide-conjugated β-gal. In rows 1–4 peptide-conjugated β-gal comprising peptide 2, 3, 4 and 5 respectively (SEQ ID Nos:2–5 respectively) were incubated with cells in the presence of non biotinylated peptides 1–6 (SEQ ID Nos:1–6 respectively) which were added to columns 1–6 respectively. Peptide 1 (SEQ ID NO:1) did not block the internalization by any of the peptides. Peptides 2–6 (SEQ ID Nos:2–6 respectively) blocked the internalization of peptide 2-conjugated β-gal and peptides 4 (SEQ ID NO:4) and peptide 5 (SEQ ID NO:5) blocked the internalization of peptide 2 through peptide 6-conjugated β-gal indicating that these peptides more efficiently bound to the cells than any others.

Figure 12:
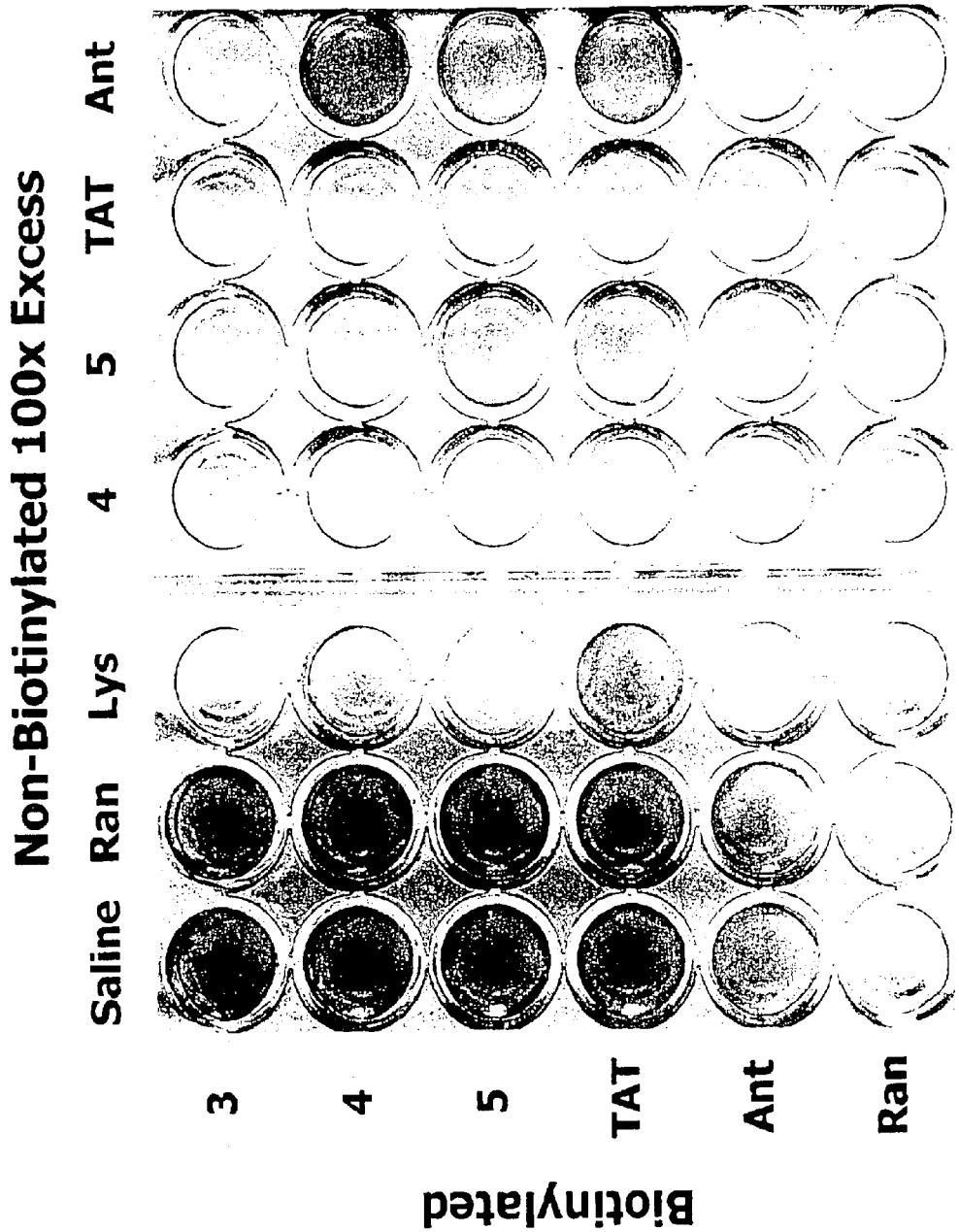
FIG. 12 shows the ability of various peptides (peptides 4, 5, random peptide, antennapedia peptide, and TAT-PTD SEQ ID NO:4, SEQ ID NO:5, SEQ ID NO:20, SEQ ID NO:19 and SEQ ID NO:21 respectively) to compete for binding to peptide 3, 4, 5, TAT-PTD, antennapedia peptide, and a random peptide (SEQ ID NO:3, SEQ ID NO:4, SEQ ID NO:5, SEQ ID NO:21, SEQ ID NO:19 and SEQ ID NO:20 respectively) in Hig-82 cells.

FIG. 12 also shows the ability of the various non-biotinylated peptides to compete for internalization of the peptide-conjugated β-gal. A 100 fold excess of peptide 5 (SEQ ID NO:5) was able to completely inhibit the uptake of peptides 3, 4 (SEQ ID NOs:3 and 4 respectively) and the antennapedia peptide (SEQ ID NO:19) and significantly inhibit the uptake of TAT-PTD (SEQ ID NO:21) and itself. Surprisingly peptide 6 (SEQ ID NO:6) was able to inhibit the uptake of peptide 2 and 3, but not peptides 4 and 5, even though peptide 6 is only weakly able to transduce cells compared with peptides 2–5. Also tested were saline alone, a random peptide (SEQ ID NO:20), TAT-PTD (SEQ ID NO:21) and a polylysine peptide having a MW between 1,000 D and 4,000 D with an average MW of 2,500 D (purchased from Sigma, St. Louis, Mo.). The ability of the polylysine peptide to inhibit uptake suggests that the charge of the peptide is important for at least part of the process of peptide-mediated internalization.

Example 6

Circular Dichroism Spectroscopy

Stock solutions of peptides 1, 2, 3, 4, 5 and 6 (SEQ ID NOs:1–6 respectively), as well as TAT-PTD (SEQ ID NO:21), and the antennapedia peptide (SEQ ID NO:19) were diluted to 1.5 mg/ml in 5 mM $KPO_4$ at pH 7.4. Measurements were made using an Aviv 62DS spectropolarimeter over the wavelength range from 300 to 190 nm (except for TAT-PTD, where sample absorbency precluded measurements below 192 nm even after sample dilution), with a 0.5 nm step size, at room temperature using a 0.1 cm pathlength quartz cell (Hellma). Ellipticity measurements below 190 nm were precluded due to solvent absoption. All reported spectra were baseline corrected (by subtraction of similarly collected, averaged baselines of buffer alone) and smoothed using a Savitzky Golay filter.

Figure 10A:
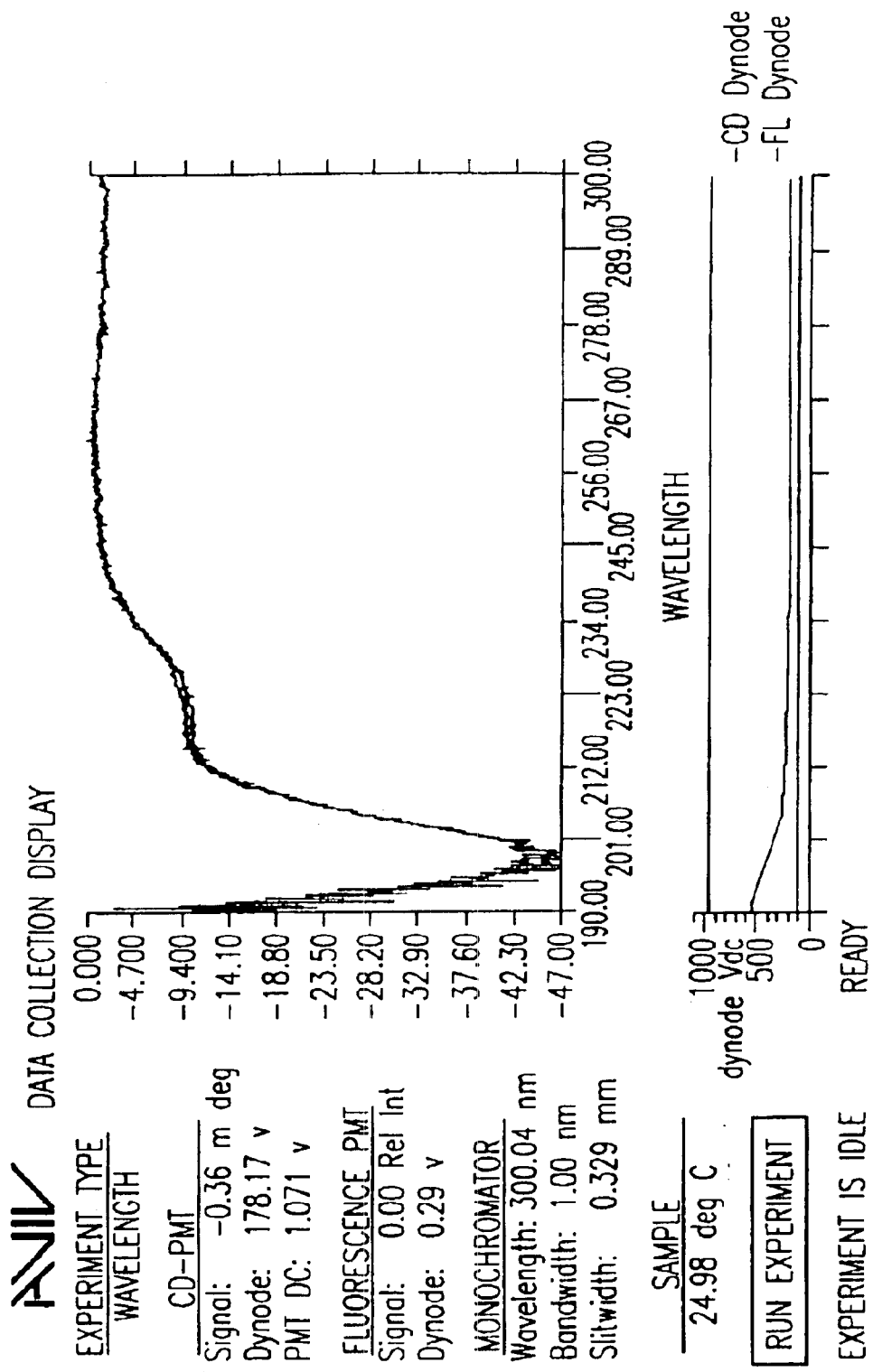
FIGS. 10A-H shows the circular dichroism plot for the peptides 1–6 (SEQ ID Nos:1–6 respectively) (FIGS. 10A-F respectively), antennapedia peptide (SEQ ID NO:19) (FIG. 10G) and a random peptide (SEQ ID NO:20) (FIG. 10H) at different wavelengths.
Figure 10B:
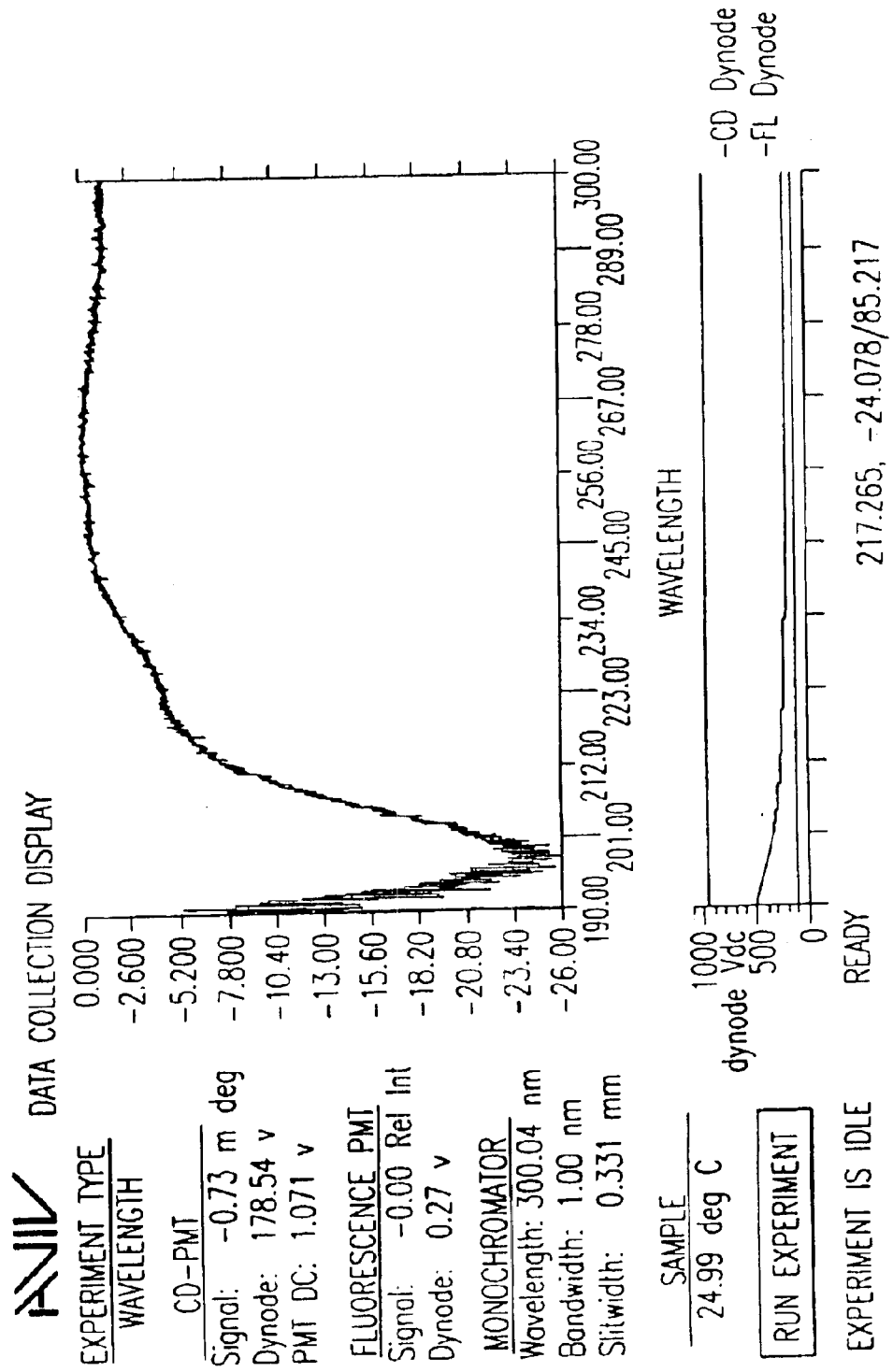
Figure 10C:
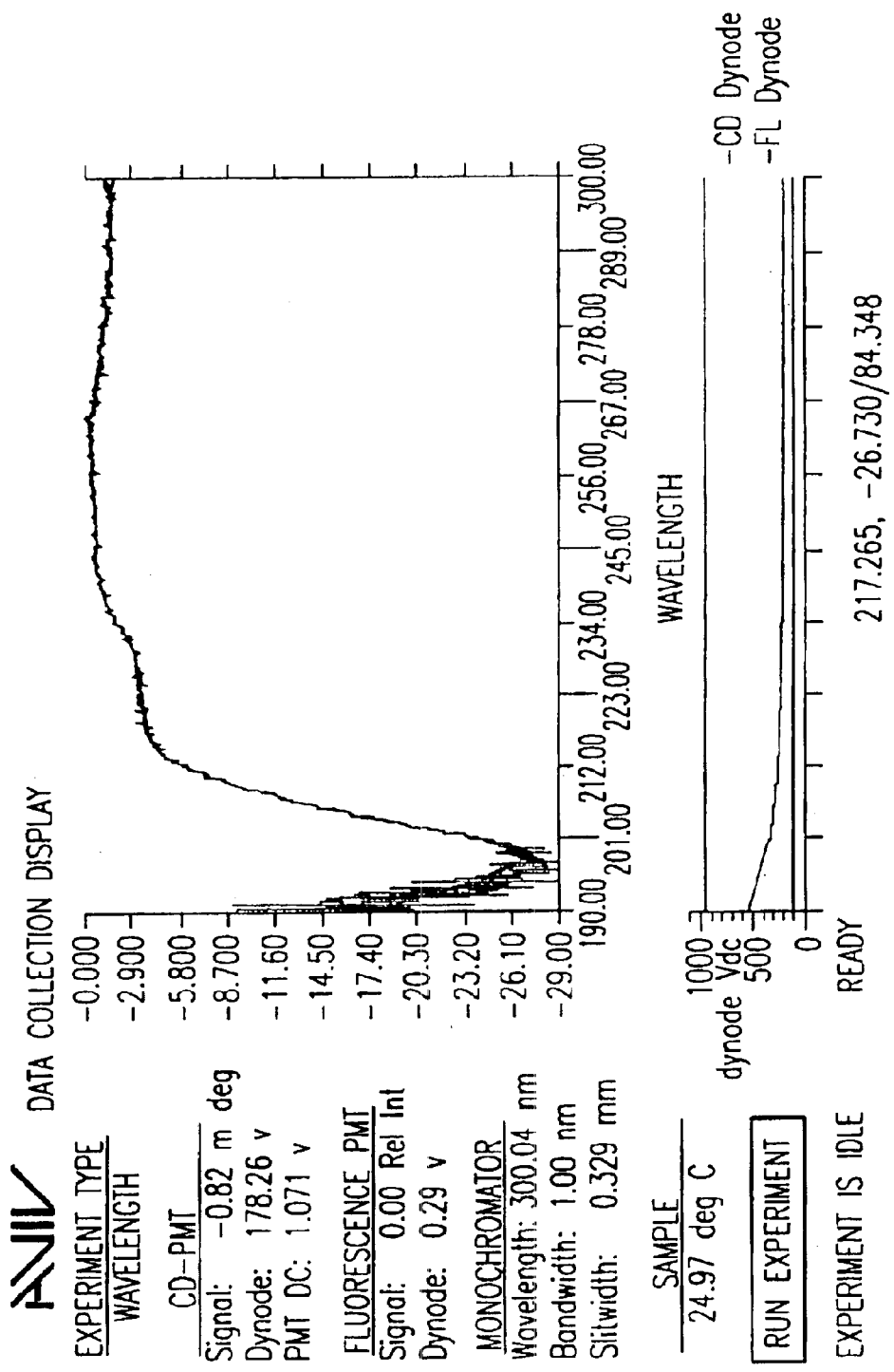
Figure 10D:
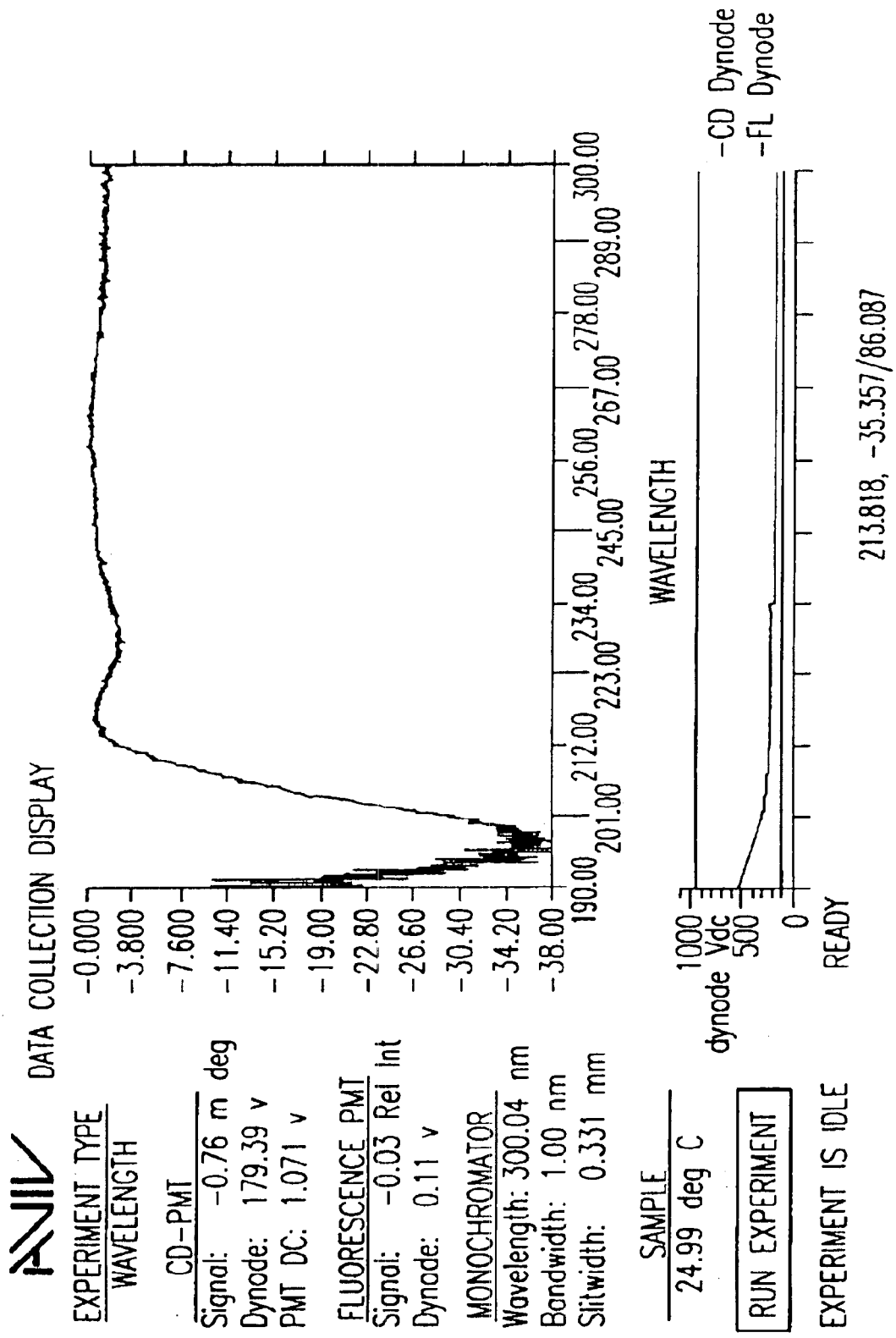
Figure 10E:
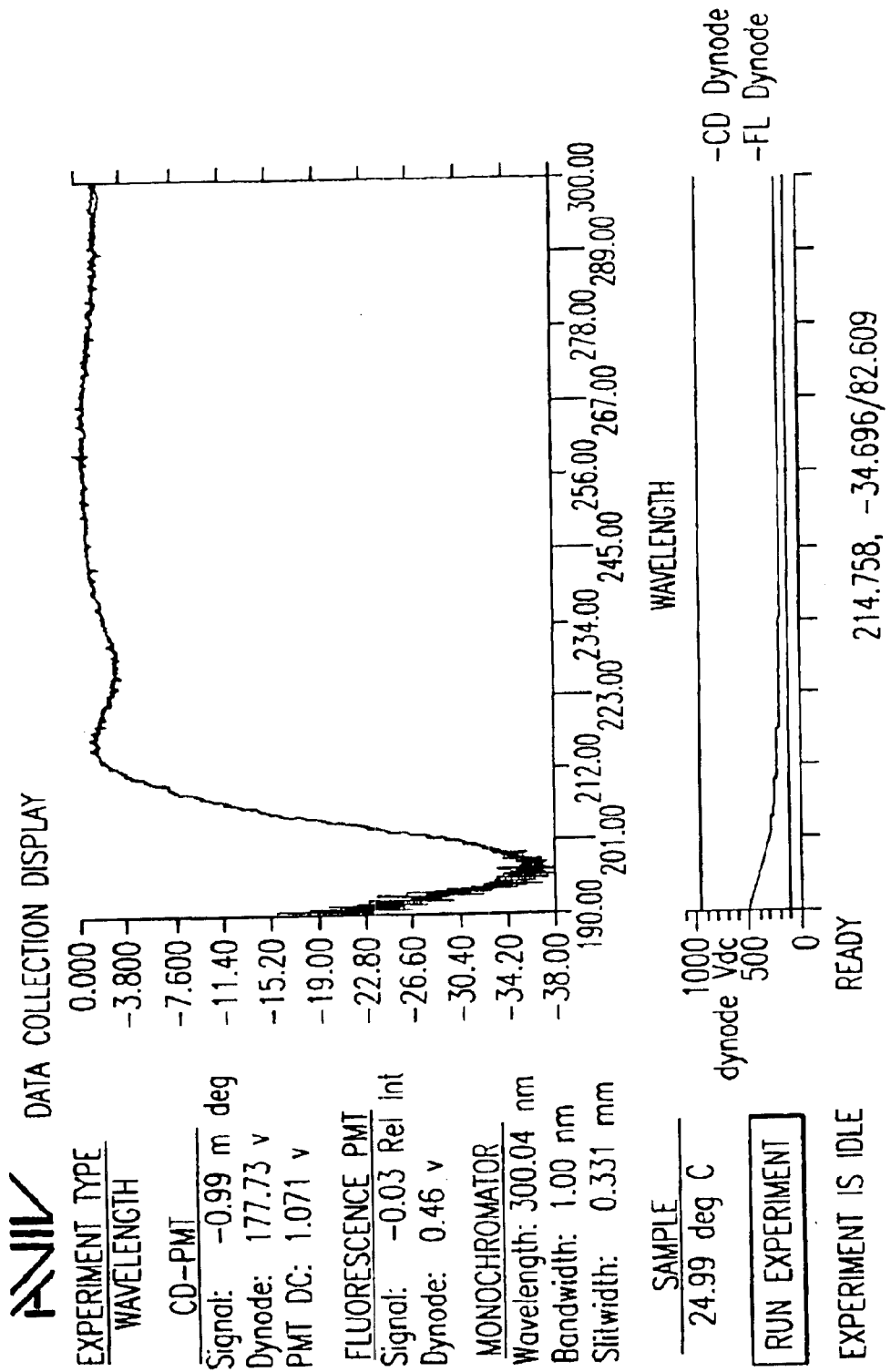
Figure 10F:
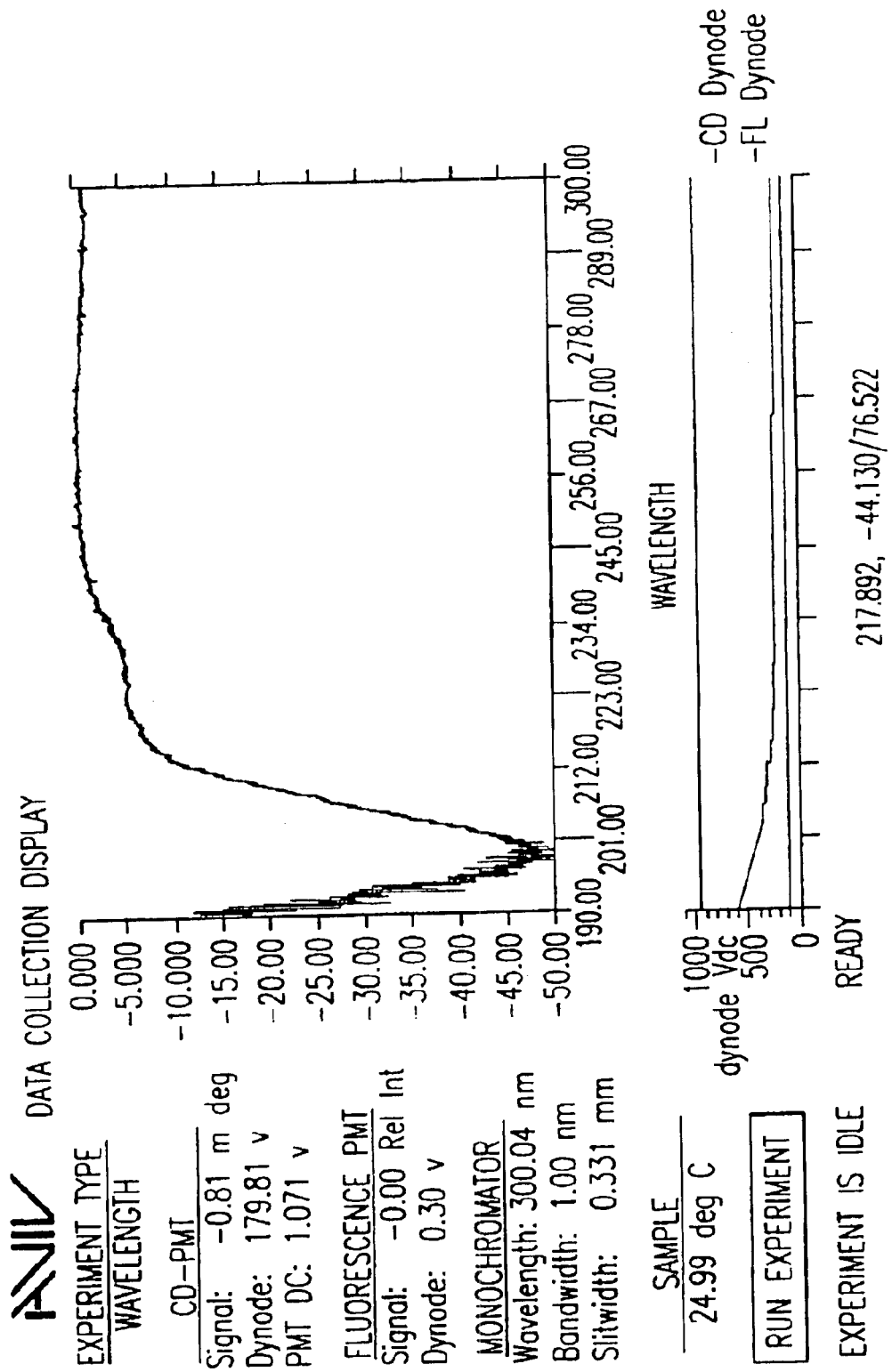
Figure 10G:
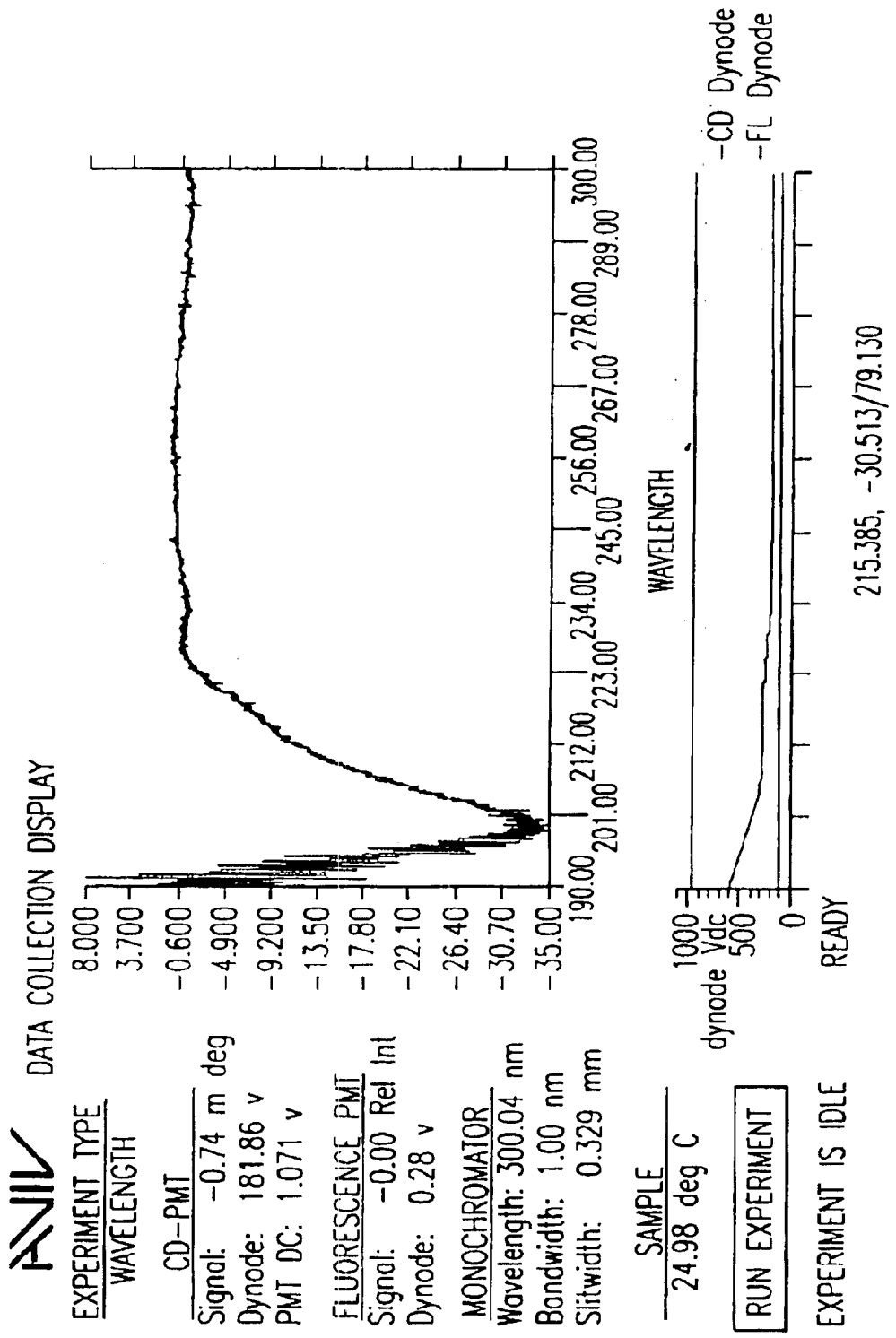
Figure 10H:
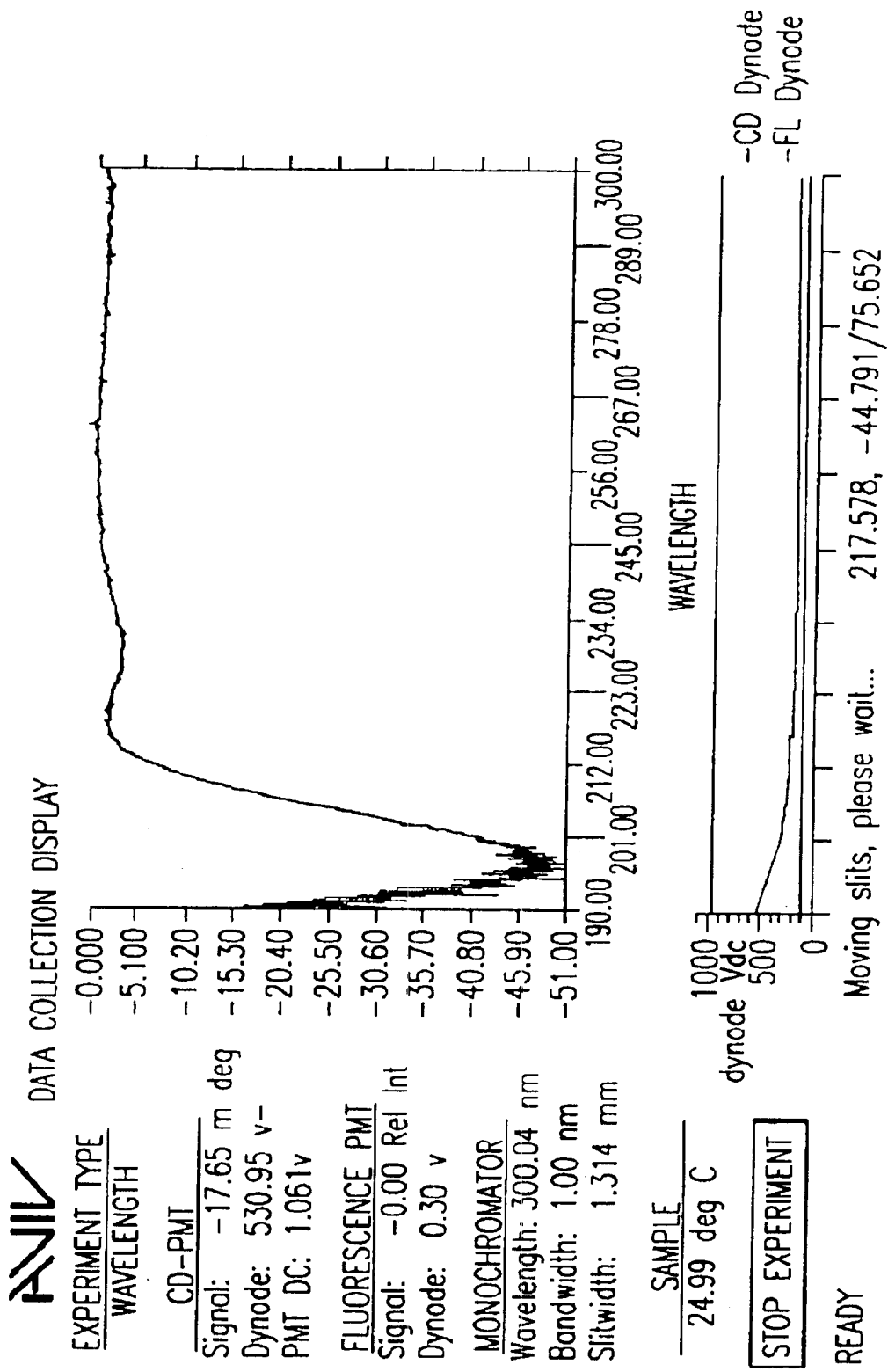

FIG. 10A-H shows that the peptides have a small dip at a wavelength of 225 nm which indicative of possible insignificant secondary structure for α helices. Specifically, FIG. 10A-H shows the circular dichroism plot for peptide 1 (SEQ ID NO:1; FIG. 10A), peptide 2 (SEQ ID NO:2; FIG. 10B), peptide 3 (SEQ ID NO:3; FIG. 10C), peptide 4 (SEQ ID NO:4, FIG. 10D), peptide 5 (SEQ ID NO:5, FIG. 10E), peptide 6 (SEQ ID NO:6, FIG. 10F), antennapedia peptide (SEQ ID NO:19, FIG. 10G) and a random peptide (SEQ ID NO:20; FIG. 10H).

Figure 11A:
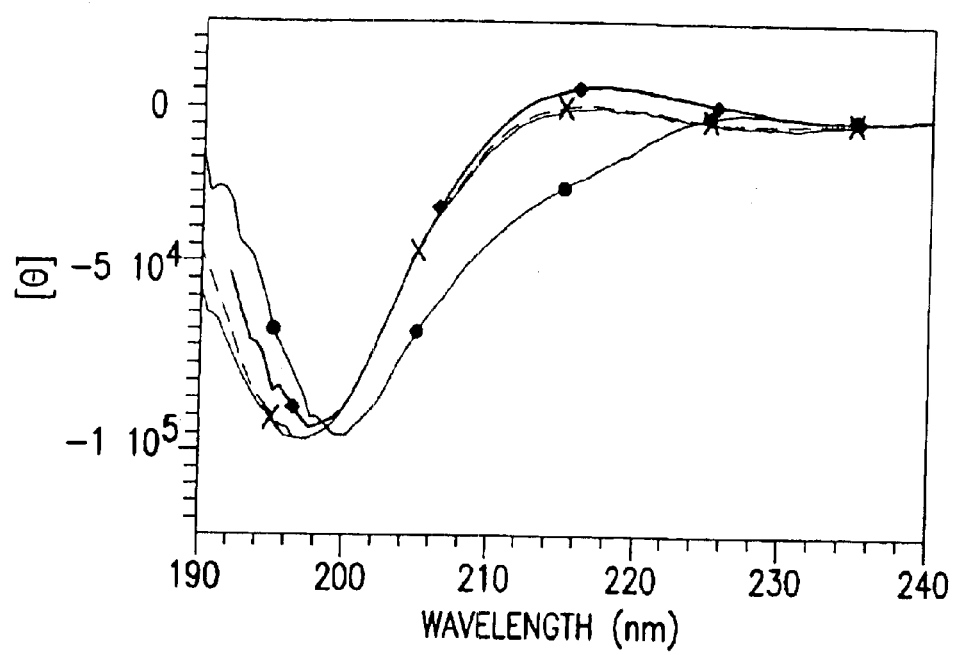
FIGS. 11A & B: (A) Overlay of the CD spectra of peptide 4 (solid line, SEQ ID NO:4), peptide 5 (dashed line, X, SEQ ID NO:5), TAT-PTD (solid line, ♦, SEQ ID NO:21), and antennapedia peptide (solid line, ●, SEQ ID NO:19). (B) Overlay of the CD spectra of peptide 1 (solid line, O, SEQ ID NO:1), peptide 2 (dashed line, ▲, SEQ ID NO:2), peptide 3 (dashed line, ▼, SEQ ID NO:3), peptide 6 (solid line, □, SEQ ID NO:6).
Figure 11B:
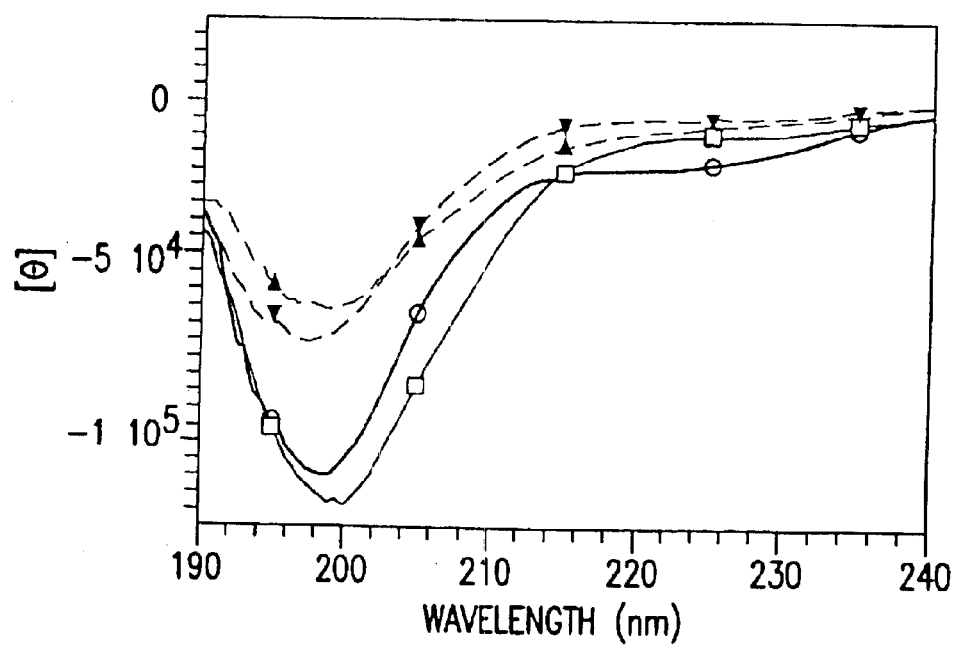

FIG. 11A & B shows that qualitatively, the spectra of peptides 1–6 fall into three general groups. FIG. 11A shows that the spectra of the highly active peptides 4 and 5 (SEQ ID NOs: 4 and 5 respectively) are nearly super-imposable with that of TAT-PTD (SEQ ID NO:21) and somewhat similar to the antennapedia peptide (SEQ ID NO:19). Peptides 2 and 3 (SEQ ID NOs: 2 and 3 respectively), which have an intermediate activity, yield spectra which are similar to each other, but significantly different from peptides 4 and 5. The lower activity peptides 1 and (SEQ ID NOs: 1 and 6 respectively) fall into a third class and share sonic similarity to the random peptide (SEQ ID NO:20) which does not have activity. The peptides do not have a significant helical content, which would give rise to a bilobed minima at ~205 and 220 nm, and a large positive peak at ~195 nm. Rather, the peptides appear to be enriched in a poly-proline-type helix (which does not require the presence of prolines). See Sreerama & Woody, *Biochemistry* 33:10022–10025 (1994). This type of structure is consistent with some of the observations made regarding the antennapedia peptide where the substitution of the prolines into the peptide sequence did not disrupt activity, nor did the substitution of D-amino acids and/or reversal of the chain direction disrupt activity. See Derossi et al., *J. Biochcem.* 217:18188–18193 (1996); Berlose et al., *Eur. J. Biochem.* 242:372 (1996). These substitutions would not affect the charge distribution on a poly-proline-type helix, nor be disruptive to this structure. The amphipathic cationic peptides of the present invention likely interact with the negative charges on the surface of the bilayers.

The CD spectra of the peptides was also analyzed following addition to small unimellar vesicles (SUVs). In the presence of SUVs, which comprise mixed phospholipids that are primarily phosphatidylcholines, no significant changes were obsessed in the CD spectra. However, when the SUVs were composed of dipalmitoyl phosphatidylserine, a large change in the resulting CD spectra was observed which correlated with transfer activity.

Example 7

Delivery of an Apoptotic Peptide to Cells via the Peptides of the Present Invention To demonstrate that the peptides of the present invention could facilitate the uptake of an apoptotic peptide KLAK-LAKKLAKLAK (SEQ ID NO:23) into cells and induce apoptosis therein, a continuous peptide, termed the "death peptide", comprising peptide 5 and the apoptotic peptide was synthesized (RRQRRTSKLMKRGGKLAKLAKKLAKLAK (SEQ ID NO:24)) (Research Genetics, Huntsville, Ala.).

$2 \times 10^5$ cells (HIG82, MCA205 or Jurkatt) were seeded into 24 well plates. Forty-eight hours later, 100 μM, 50 μM, 25 μM, 6.25 μM and 3.1 μM of the either the death peptide (SEQ ID NO:24), peptide 5 alone (SEQ ID NO:5) or the apoptotic peptide alone (SEQ ID NO:23) was added to the cells. To check for cell viability, three hours later, the media was aspirated and 1 ml of scrum-free media containing 0.25 mg of MTT was added to each well and incubated for 4 hours at 37° C. MTT-containing media was then removed and 1 ml of absolute isopropanol containing 0.4N HCl was added. Photographs were taken of the plates, then the cells were harvested and any debris was centrifuged. OD as taken at λ=570 nm. Each sample point was performed in triplicate.

Figure 14:
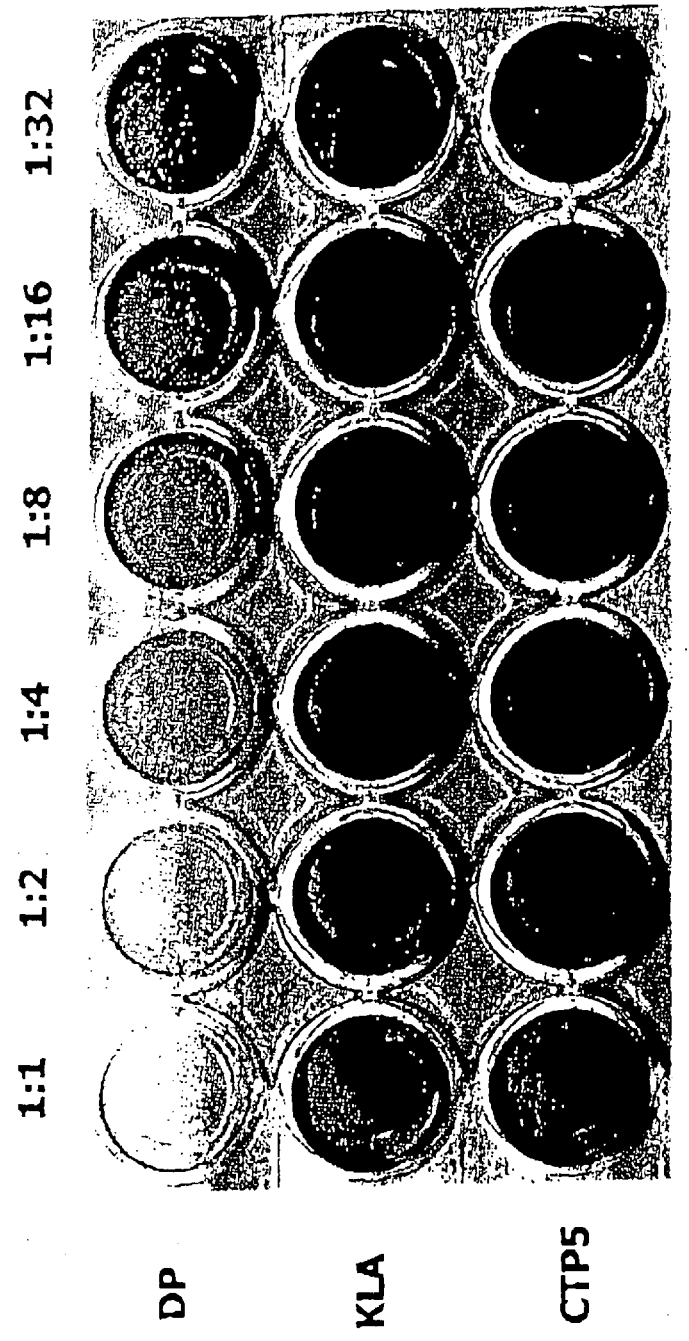
FIG. 14: shows the ability of the death peptide (SEQ ID NO:24), an antimicrobial apoptotic peptide KLAK-LAKKLAKLAK (SEQ ID NO:23) and peptide 5 at various concentrations to impair cell viability in HIG 82 Cells.
Figure 15:
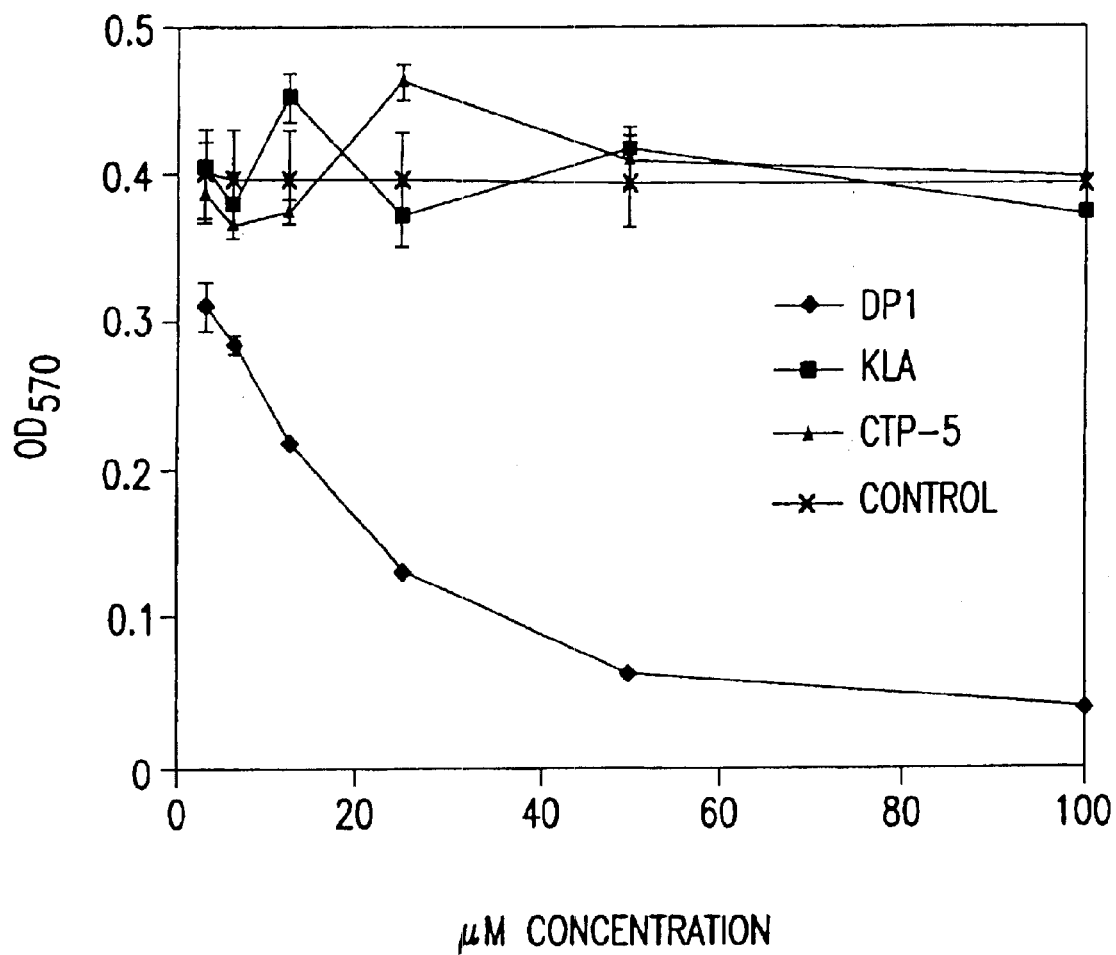
FIG. 15: is a graph showing the ability of the death peptide (SEQ ID NO:24), an antimicrobial apoptotic peptide KLAKLAKKLAKLAK (SEQ ID NO:23) and peptide 5 at various concentrations to impair cell viability in HIG 82 Cells as measured by $OD_{570}$ using an MTT assay.

FIG. 14 and FIG. 15 shows the ability of the "death peptide" to impair HIG-82 cell viability. In contrast, peptide 5 alone and the apoptotic peptide alone did not impair viability.

To determine whether the death peptide could induce apoptosis in tumor cells and inhibit tumor growth in vivo, C57BL/6 mice bearing day 7 tumors in each flask (seeded with $1 \times 10^5$ MCA205 cells) were injected daily for 10 days with a 50 μl volume of 1 mM death peptide (SEQ ID NO:24; DP1) or the apoptotic peptide alone (SEQ ID NO:23; KLA) or a saline mock into both tumors. Five mice were used in each group. Tumor volume was estimated by multiplying maximum length×width$^2$. Separately, C57BL/6 with single, day 12 tumors were injected with 1 mM death peptide (SEQ ID NO:24; DP1), apoptotic peptide alone (SEQ ID NO:23; KLA) or saline for eleven days. Ten mice comprised each group. On the final day, the mice were injected with the appropriate saline or peptide solution and sacrificed 3 hours post-injection. Tumors were paraffin-embedded, sectioned, and stained for TUNEL and counterstained with methyl green or stained with hematoxylin and eosin to reveal histologic architecture.

Figure 16A:
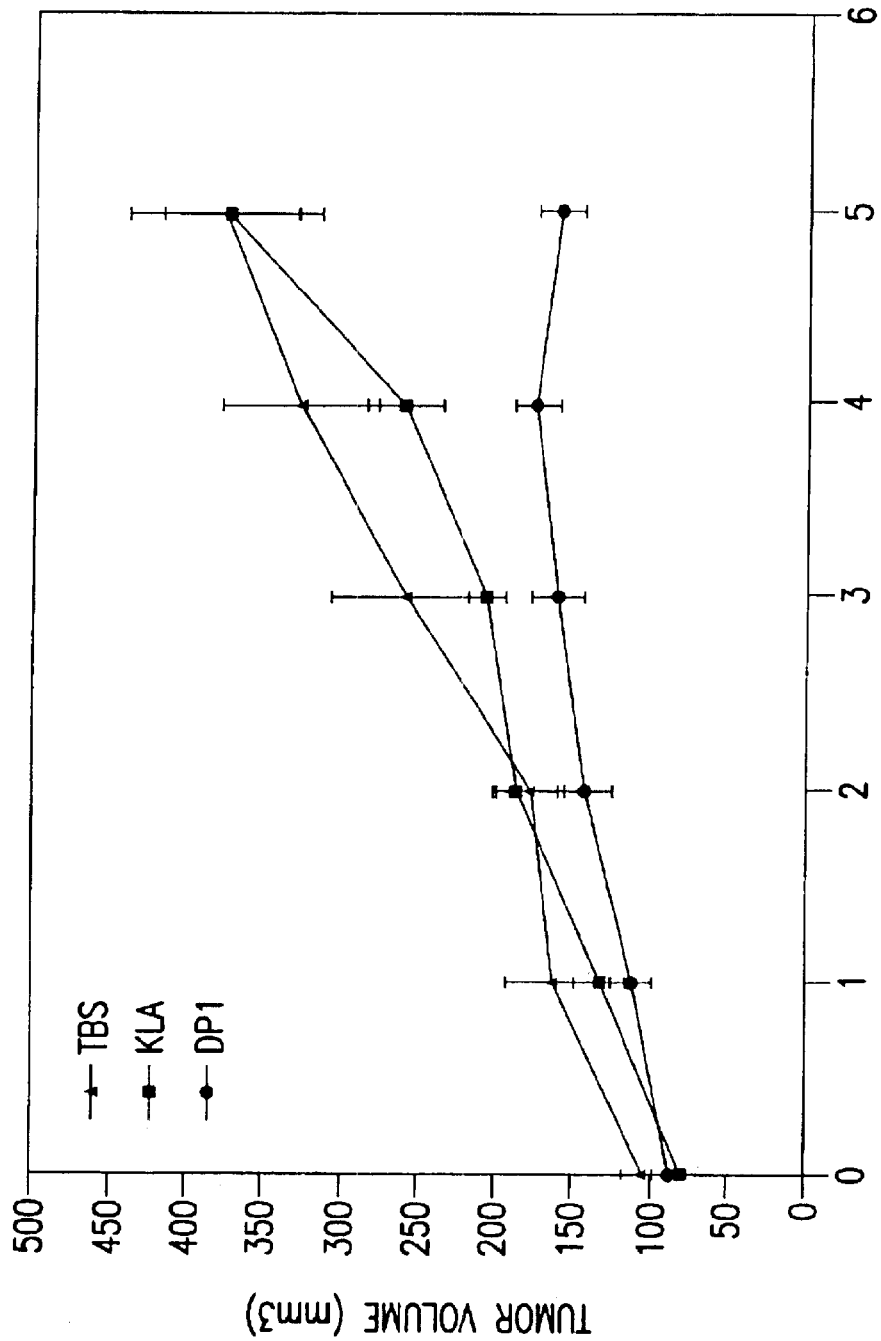
FIG. 16(A) is a graph showing the ability of the death peptide (SEQ ID NO:24) (DP1; ●), antimicrobial peptide (SEQ ID NO:23) (KLA; ■) and peptide 5 (SEQ ID NO:5) (TBS; ▲) to inhibit the growth of MCA205 tumors, (B) shows representative surface morphology of mice with fibrosarcomas when treated with the death peptide (SEQ ID NO:24; DP1) and the antimicrobial peptide (SEQ ID NO:23; KLA) respectively, (C) is hematoxylin and eosin (H&E) staining (left) and TUNEL (right) showing that the death peptide (SEQ ID NO:24; DP1) but not the antimicrobial peptide alone (SEQ ID NO:23; KLA) mediates apoptosis of MCA205 tumors in vivo, and (D) is a scatter plot showing individual tumor sizes.
Figure 16B:
Figure 16B:
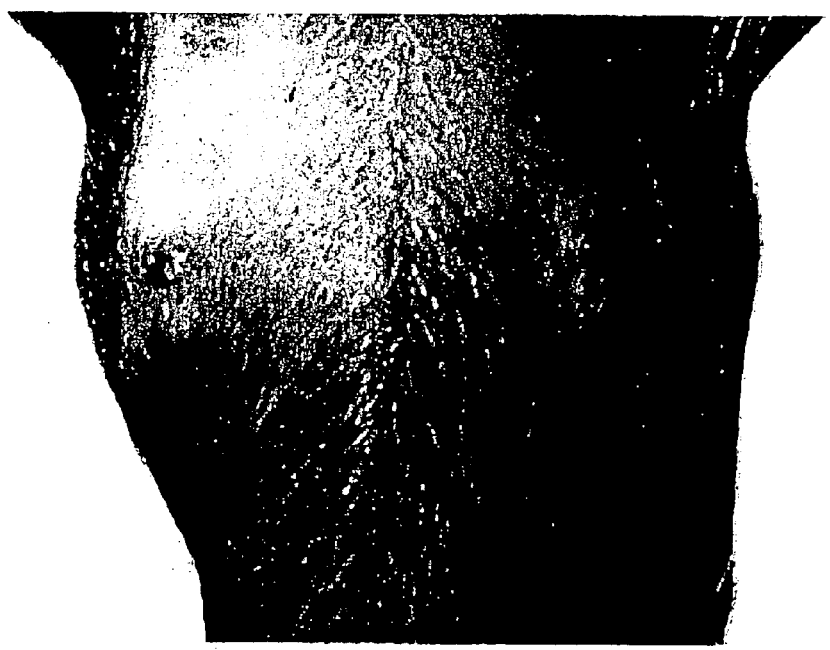

As shown in FIG. 16A, daily administration of 50 μl of 1 mM death peptide (SEQ ID NO:24, DP1) lead to a striking reduction or halt in tumor growth in the fibrosarcomas compared to the apoptotic peptide alone (SEQ ID NO:23; KLA) or tris buffered saline (TBS). By day 6, between the death peptide (DP1) and apoptotic peptide alone (KLA) groups, a p<=0.026 by a two-tailed student's t-test of the means was observed, which became –0.0001 by day 10. As a plot of individual tumor sizes shows (FIG. 16D), both the death peptide (DP1) and the apoptotic peptide alone (KLA) mouse groups begin with comparable tumor sizes. However, by day 9 of treatment, no overlap exists in the tumor sizes of the DP1-treated cohort with KLA-treated cohort. To test whether an immune response against the tumors may have been triggered by the apoptosis, treatment was halted at day 14, however, in the DP1-treated mice. Tumors continued to grow, directly correlating with the cessation of DP1 administration. FIG. 16B shows a comparison of tumor sizes between the DP1 and KLA-treated groups eight days following the initiation of treatment. There is a dramatic reduction in tumor volume in the DP1-treated mice, coincident with reduction in ulceration and bleeding in these mice. In a separate experiment, 3 out of 10 mice with single flank tumors treated with DP1 had undetectable tumors following 11 days of treatment. Importantly, repeated administration of DP1 resulted in no obvious side-effects in treated mice.

Figure 16C:
Figure 16C:
Figure 16C:
Figure 16C:
Figure 16D:
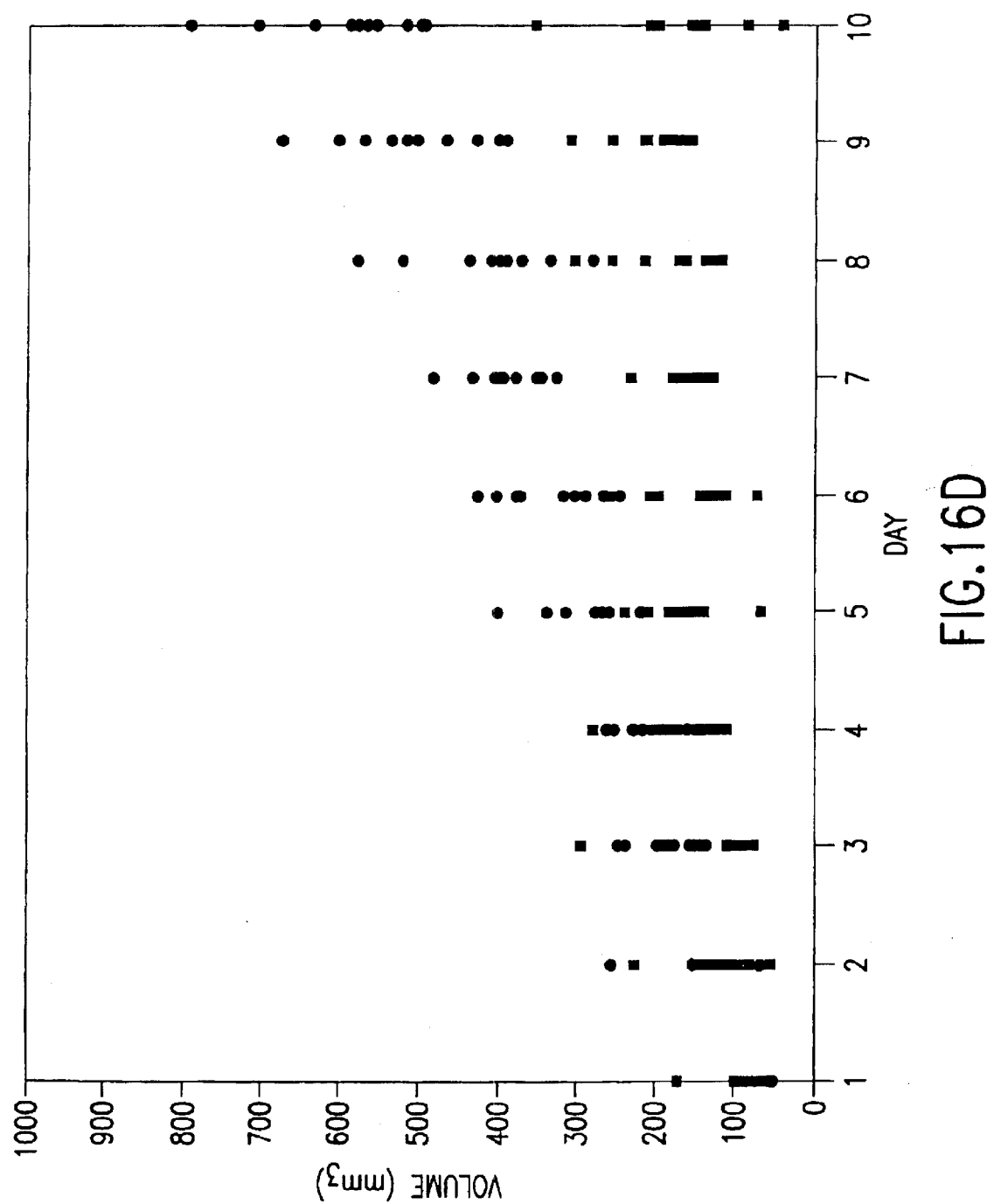

To test whether apoptosis was the mechanism of tumor killing in vivo and to study the effects of death peptide administration on tumor architecture, fibrosarcomas treated daily for 11 days with death peptide (SEQ ID NO:24; DP1), apoptotic peptide alone (SEQ ID NO:23, KLA) or tris buffered saline (TBS) were injected with 50 μl of 1 mM DP1, KLA or TBS on the eleventh day and sacrificed three hours later. Tumors were excised, embedded, sectioned, and stained with either TUNEL or hematoxylin and eosin. As shown in FIG. 16C, treatment with DP1 mediates a potent apoptosis in MCA205 fibrosarcomas in vivo. A broad zone of anuclear and acellular cosinophilic debris is ringed by a zone of tumor cells in the process of undergoing apoptosis, as shown in the bottom right panel (FIG. 16C). The zones of killing are substantial; in some instances, an estimated 10–20% of total tumor volume stained TUNEL-positive following DP1 administration. No TUNEL staining is observed in the KLA-treated tumors, indicating the requirement for linkage to peptide 5 (SEQ ID NO:5) for induction of apoptosis.

In addition, the death peptide was administered to rabbits with IL-1-induced arthritis (see Ghivizzani et al. *J. Immunol.* 159:3604 (1997)). Three arthritic rabbits received the death peptide, three received peptide 5 alone and 3 received the apoptotic protein alone. The rabbits were sacrificed 24 or 72 hours post-injection of the peptides and the rabbit knee capsules were removed for histology analysis and TUNEL staining.

Figure 18:
FIG. 18 shows TUNEL hematoxylin and eosin staining of tissue from arthritic rabbit knee joints indicating that the death peptide (SEQ ID NO:24; DP1) mediates apoptosis in hyperplastic synovium whereas the antimicrobial peptide alone (SEQ ID NO:23, KLA) does not.
Figure 18:
Figure 18:

FIG. 18 shows that the delivery of the death peptide (SEQ ID NO:24; DP1) mediated apoptosis of hyperplastic synovium in vivo whereas the antimicrobial peptide alone (SEQ ID NO:23; KLA) did not. Furthermore, injection of the death peptide (SEQ ID NO:24; DP1) into arthritic rabbit joints caused a great reduction in the number of white blood cells in the lavage fluid if IL-1 inflamed rabbit joints as compared to peptide 5 alone (SEQ ID NO:5; peptide control) (see FIG. 19). These data indicate that the internalizing peptides of the present invention are effective for delivering apoptosis factors to arthritic joints and may be useful for the treatment of arthritis.

To demonstrate that other apoptotic factors could effectively be delivered to cells, the internalizing peptide 5 (SEQ ID NO:5; pep 5) of the present invention was linked to p53. An expression clone was prepared by using PCR to first create an expression cassette having pep5 at the amino terminus and a his tag at the carboxy terminus of the p53 coding sequence. The expression cassette was cloned into the pet3b vector (Stratagene, La Jolla, Calif.). The expression clone was then transformed into BL21 *E. coli* expression strain and induced with 0.5 mM IPTG for fusion protein expression. The fusion protein was purified using a nickel column.

HIG-82 cells were grown as described above and transfected with a reporter plasmid expressing the luciferase gene driven by the p21 promoter. The HIG-82 cells were transfected with p21-luciferase plasmid by calcium phosphate methods. In addition, as positive controls, a CMV promoter driven p53 plasmid and an Adp53 viral vector were transfected into HIG-82 cells together with the reporter plasmid expressing the luciferase gene driven by the p21 promoter. Purified pep5/p53/his was added to the culture 6 hours post addition of the reporter plasmid expressing the luciferase gene driven by the p21 promoter.

The reporter plasmid expresses the luciferase gene when p53 binds to the p21 promoter. Therefore, the presence of p53 in cells transfected with the reporter plasmid may be monitored by the presence of luciferase activity in the cells. To check for the presence of luciferase activity in the cells, the cells were washed 2× with PBS, harvested and lysed. The cellular lysate was used in a luciferase activity assay performed using a luciferase assay kit (Promega, Madison, Wis.).

Figure 20:
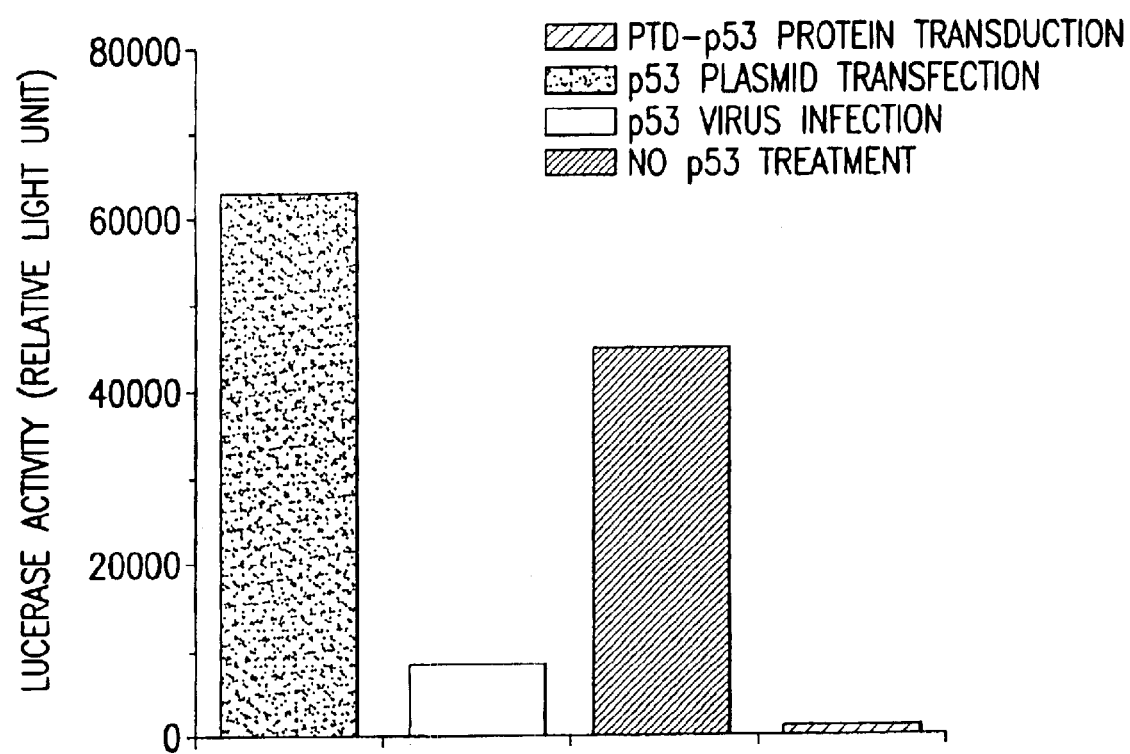
FIG. 20 is a bar graph showing that internalization of p53 into cells via the peptides of the present invention induces p21 promoter driven luciferase expression in a rabbit synovial cell line (Hig-82 cells).

FIG. 20 shows the ability of pep5:p53 to induce p21 promoter driven luciferase expression in HIS-82 cells. Pep5:p53 was able to induce luciferase expression to similar levels as a plasmid expressing p53 and was much more effective than an adenovirus vector expressing p53. These data indicate that the internalizing peptides of the present invention can effectively deliver and internalize p53 to cells.

Example 8

Facilitation of the Delivery of GST Fusion Proteins to Cells Using Glutathione-linked Internalizing Peptides of the Present Invention GST-eGFP (glutathione-S-transferase tagged green flourescent protein), having in addition a histidine tag, as expressed in *E. coli* and purified using conventional techniques using a Nickel column to which the histidine tag binds (See Mi et al., *Mol. Ther.* (2000) in press). The purified GST-eGFP (200 μl of 0.8 mg/ml/total of 0.16 mg in TBS containing 1 mM $CaCl_2$ and 10 mM $MgCl_2$) was incubated together with 50 μl pep5 (SEQ ID NO:5; 2 mg/ml in TBS) in a total volume of 500 μl by rotating overnight at 4° C. The mixture was then dialyzed against TBS at 4° C. for 2 hours with one change of buffer.

Hig-82 cells were grown between 80% to 100% confluency in 12 well plates. The cells were washed 2× with 1 ml of TBS containing 1 mM $CaCl_2$ and 10 mM $MgCl_2$, and 0.1% BSA. After the final wash, various dilutions of the glutathione-pep5-GST-eGFP complex (4×, 10×, 20×) were added to the cells, as well as the negative control (GST-eGFP alone) and "enriched" TBS. The cells were incubated together with the complex or controls at 37° C. for 2 hours. The cells were then washed with "enriched" TBS 3× and examined by flourescent microscopy.

Figure 21A:
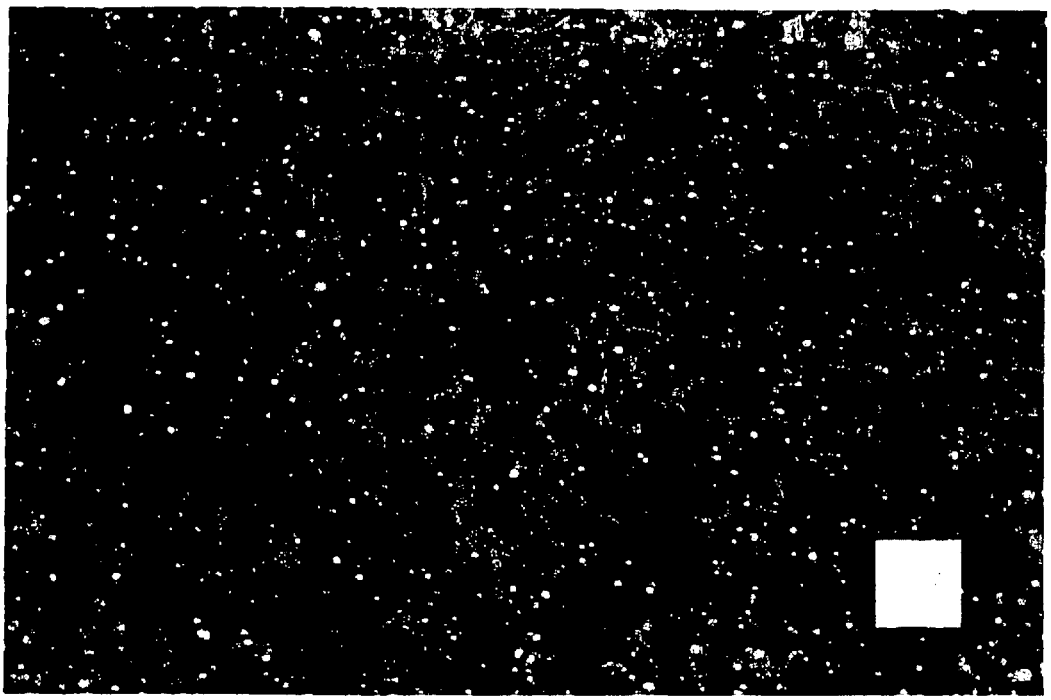
FIG. 21 shows fluorescence microscopy of HIG-82 cells treated with glutathione-pep5 (SEQ ID NO:5) linked to GST-eGFP (Panel A) or GST-eGFP alone (Panel B).
Figure 21B:
Figure 22C:
FIG. 22(A) shows a cross section of cervical mucosa treated with pep5-eGFP, (B) shows an optical orthogonal section through an explant of cervical mucosa, (C) shows a 3D reconstruction of cervical mucosa cells treated with pep5-eGFP viewed from within the tissue, and (D-G) shows flow cytometry analysis of a single cell suspension of cervical mucosa cells transduced with pep5-eGFP.
Figure 22B:
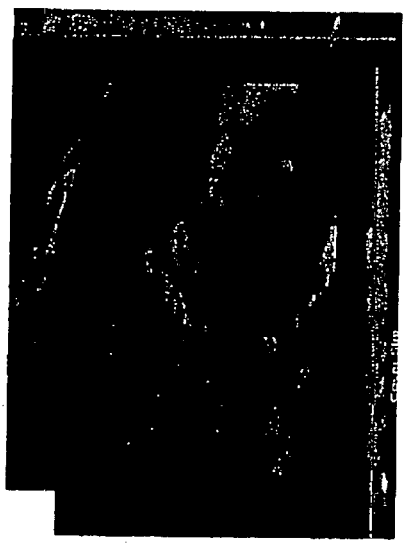
Figure 22A:
Figure 22D:
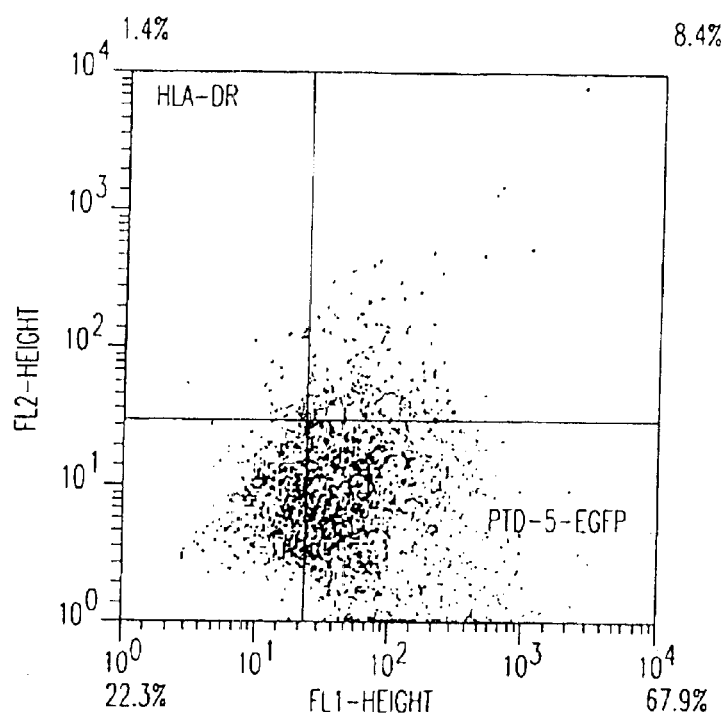
Figure 22E:
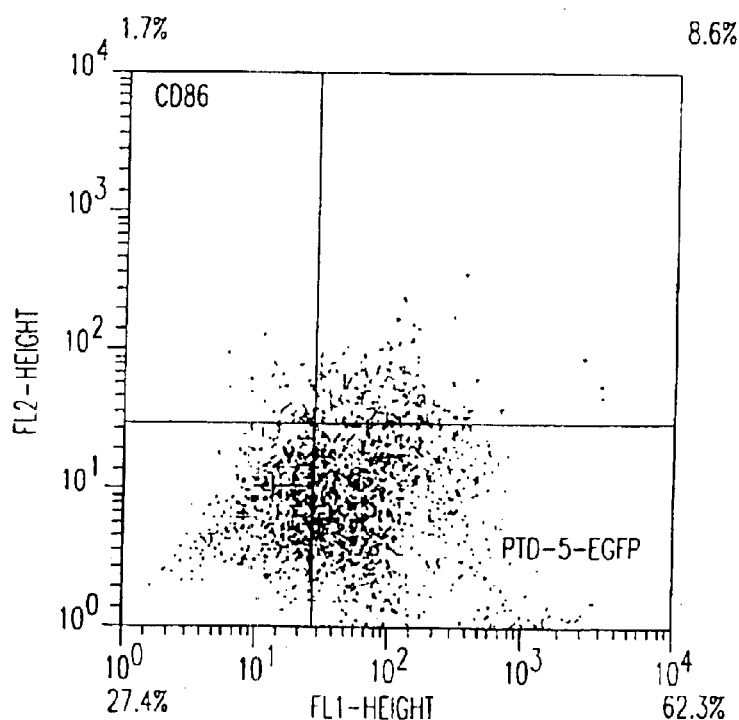
Figure 22F:
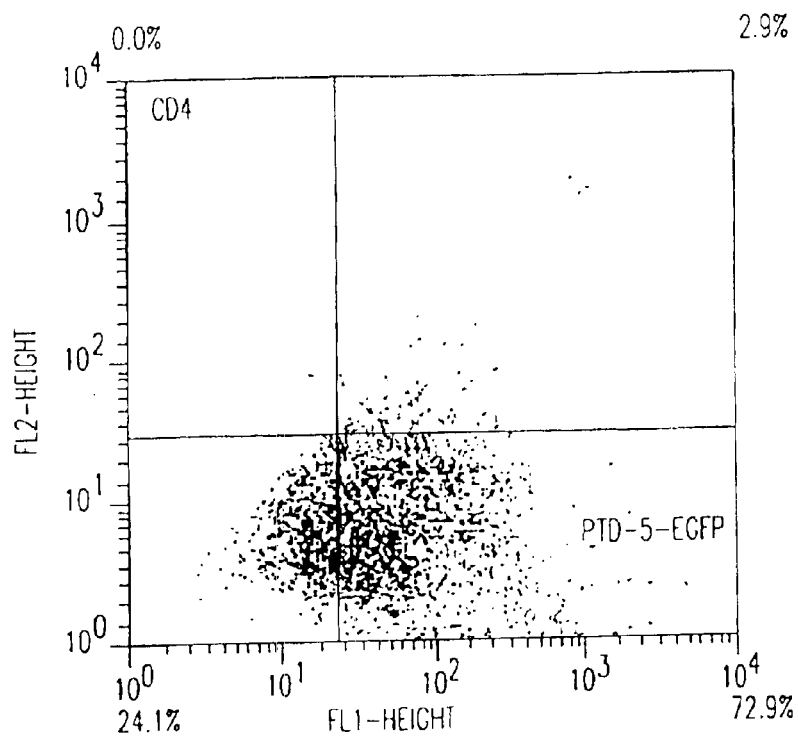
Figure 22G:
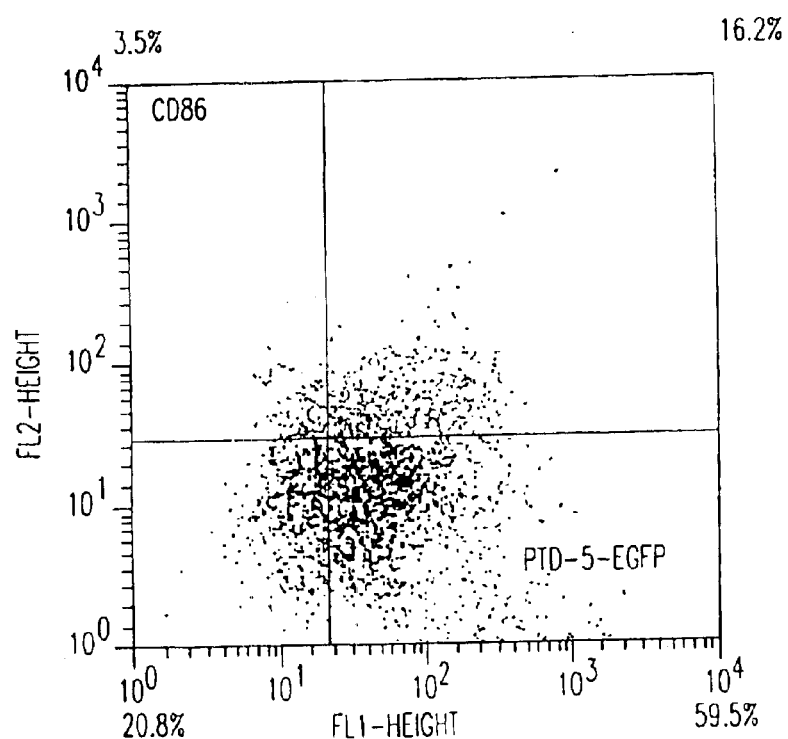

FIG. 21 shows that the glutathione-pep5:GST-eGFP complex was very effectively internalized by HIG-82 cells (panel A) as compared to the GST-eGFP alone (panel B) indicating that glutathione linked internalizing peptides of the present invention are useful for facilitating the uptake of GST proteins to target cells.

We claim:

1. A peptide having a amino acid sequence selected from the group consisting of PIRRRKKLRRLK (SEQ ID NO:4); RRQRRTSKLMKR (SEQ ID NO:5); SRRKRQRSNMRI (SEQ ID NO:9); SFHQFARATLAS (SEQ ID NO:33); DPATNPGPHFPR (SEQ ID NO:58); and TLPSPLALLTVH (SEQ ID NO:59).

2. The peptide of claim 1 wherein said peptide facilitates cellular internalization of a cargo linked thereto.

3. The peptide of claim 2 wherein the peptide is PIRRRKKLRRLK (SEQ ID NO:4).

4. The peptide of claim 2 wherein the peptide is RRQRRTSKLMKR (SEQ ID NO:5).

5. The peptide of claim 2 wherein the peptide is SRRKRQRSNMRI (SEQ ID NO:9).

6. The peptide of claim 2 wherein the peptide is SFHQFARATLAS (SEQ ID NO:33).

7. The peptide of claim 2 wherein the peptide is DPATNPGPHFPR (SEQ ID NO:58).

8. The peptide of claim 2 wherein the peptide is TLPSPLALLTVH (SEQ ID NO:59).

9. The peptide of claim 1 wherein the peptide provides for nuclear translocation in a target cell.

10. A method for inducing synovial cell death comprising administering a peptide-cargo complex to said synovial cell wherein the peptide has an amino acid sequence selected from the group consisting of PIRRRKKLRRLK (SEQ ID NO:4), RRQRRTSKLMKR (SEQ ID NO:5), SRRKRQRSNMRI (SEQ ID NO:9), SFHQFARATLAS (SEQ ID NO:33), DPATNPGPHFPR (SEQ ID NO:58) and TLPSPLALLTVH (SEQ ID NO:59).

11. The method of claim 10 wherein the cargo is an apoptotic protein.

12. The method of claim 10 where the apoptotic protein is selected from the group consisting of p53, caspase-3, HSV thymidine kinase and an antimicrobial peptide.

13. The method of claim 12 wherein the antimicrobial peptide has an amino acid sequence selected from the group consisting of KLAKLAK (SEQ ID NO:22) and KLAKLAKKLAKLAK (SEQ ID NO:23).

14. The method of claim 10 wherein the peptide-cargo complex has an amino acid sequence RRQRRTSKLMKRGGKLAKLAKKLAKLAK (SEQ ID NO:24).

* * * * *

UNITED STATES PATENT AND TRADEMARK OFFICE
CERTIFICATE OF CORRECTION

PATENT NO. : 6,881,825 B1
DATED : April 19, 2005
INVENTOR(S) : Robbins et al.

It is certified that error appears in the above-identified patent and that said Letters Patent is hereby corrected as shown below:

Column 1,
Line 5, insert the following paragraph:
-- This invention was made in part with support from the National Institutes of Health under grant number AR-6-2225. Therefore, the United States Government has certain rights in the invention. --.

Signed and Sealed this

Twenty-second Day of November, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,881,825 B1 |
| APPLICATION NO. | : 09/653182 |
| DATED | : April 19, 2005 |
| INVENTOR(S) | : Paul D. Robbins et al. |

It is certified that error appears in the above-identified patent and that said Letters Patent is hereby corrected as shown below:

On the Title Page, Item (54) and in the Specification, Column 1, Title:

"IDENTICATION OF PEPTIDES THAT FACILITATE UPTAKE AND CYTOPLASMIC AND/OR NUCLEAR TRANSPORT OF PROTEINS, DNA AND VIRUES" should read -- IDENTIFICATION OF PEPTIDES THAT FACILITATE UPTAKE AND CYTOPLASMIC AND/OR NUCLEAR TRANSPORT OF PROTEINS, DNA AND VIRUSES --

IN THE SPECIFICATION:

At column 1, line 5:

"This invention was made in part with support from the National Institutes of Health under grant number AR-6-2225. Therefore, the United States Government has certain rights in the invention." should read -- This invention was made with government support under grant number AR062225 awarded by the National Institutes of Health. The government has certain rights in the invention. Work on this invention was supported by grants from the Cystic Fibrosis Foundation. --

Signed and Sealed this
First Day of October, 2013

Teresa Stanek Rea
*Deputy Director of the United States Patent and Trademark Office*